(12) United States Patent
Golshan

(10) Patent No.: US 11,911,581 B1
(45) Date of Patent: Feb. 27, 2024

(54) CATHETERS AND RELATED METHODS FOR THE ASPIRATION CONTROLLED DELIVERY OF CLOSURE AGENTS

(71) Applicant: Controlled Delivery Systems, Inc., Santa Monica, CA (US)

(72) Inventor: Ali Golshan, Santa Monica, CA (US)

(73) Assignee: Controlled Delivery Systems, Inc., Santa Monica, CA (US)

( * ) Notice: Subject to any disclaimer, the term of this patent is extended or adjusted under 35 U.S.C. 154(b) by 0 days.

(21) Appl. No.: 18/361,757

(22) Filed: Jul. 28, 2023

Related U.S. Application Data

(60) Provisional application No. 63/382,472, filed on Nov. 4, 2022.

(51) Int. Cl.
*A61M 25/10* (2013.01)

(52) U.S. Cl.
CPC .............................. *A61M 25/1018* (2013.01)

(58) Field of Classification Search
CPC ................................................ A61M 25/1018
See application file for complete search history.

(56) References Cited

U.S. PATENT DOCUMENTS

| | | |
|---|---|---|
| 3,625,793 A | 12/1971 | Sheridan et al. |
| 4,728,319 A | 3/1988 | Masch |
| 4,876,109 A | 10/1989 | Mayer et al. |
| 4,895,166 A | 1/1990 | Farr et al. |
| 4,983,166 A | 1/1991 | Yamawaki |
| 4,990,134 A | 2/1991 | Auth |
| 5,011,489 A | 4/1991 | Salem |
| 5,022,399 A | 6/1991 | Biegeleisen |
| 5,058,570 A | 10/1991 | Idemoto et al. |
| 5,074,871 A | 12/1991 | Groshong |
| 5,085,662 A | 2/1992 | Willard |
| 5,087,244 A | 2/1992 | Wolinsky et al. |
| 5,135,517 A | 8/1992 | McCoy |
| 5,226,909 A | 7/1993 | Evans et al. |
| 5,282,484 A | 2/1994 | Reger |
| 5,312,427 A | 5/1994 | Shturman |
| 5,356,418 A | 10/1994 | Shturman |
| 5,361,768 A | 11/1994 | Webler et al. |
| 5,370,653 A | 12/1994 | Cragg |
| 5,372,601 A | 12/1994 | Lary |

(Continued)

FOREIGN PATENT DOCUMENTS

| | | |
|---|---|---|
| EP | 0501081 A1 | 9/1992 |
| EP | 3275498 A1 | 1/2018 |

(Continued)

OTHER PUBLICATIONS

Aetna_ Pelvic congestion syndrome: treatments; 20 pages; retrived from the internet (https://www.aetna.com/cpb/medical/data/400_499/0441.html) on Jul. 28, 2023.

(Continued)

*Primary Examiner* — Amber R Stiles
(74) *Attorney, Agent, or Firm* — Shay Glenn LLP

(57) ABSTRACT

Balloon based therapy devices for treatment of diseased vessels are described. The devices are adapted for active aspiration of a closure zone prior to delivery of a closure agent. The devices may be used for treatment of diseased veins in the lower limbs and pelvis.

30 Claims, 51 Drawing Sheets

(56) References Cited

U.S. PATENT DOCUMENTS

| | | |
|---|---|---|
| 5,383,460 A | 1/1995 | Jang et al. |
| 5,402,790 A | 4/1995 | Jang et al. |
| 5,411,478 A | 5/1995 | Stillabower |
| 5,415,636 A | 5/1995 | Forman |
| 5,549,601 A | 8/1996 | Mcintyre et al. |
| 5,584,843 A | 12/1996 | Wulfman et al. |
| 5,628,746 A | 5/1997 | Clayman |
| 5,676,962 A | 10/1997 | Cabrera Garrido et al. |
| 5,836,905 A | 11/1998 | Lemelson et al. |
| 5,842,993 A | 12/1998 | Eichelberger et al. |
| 5,843,103 A | 12/1998 | Wulfman |
| 5,851,208 A | 12/1998 | Trott |
| 5,882,329 A | 3/1999 | Patterson et al. |
| 5,893,858 A | 4/1999 | Spitz |
| 5,895,400 A | 4/1999 | Abela |
| 5,902,266 A | 5/1999 | Leone et al. |
| 5,908,395 A | 6/1999 | Stalker et al. |
| 5,919,163 A | 7/1999 | Glickman |
| 5,921,963 A | 7/1999 | Erez et al. |
| 6,004,271 A | 12/1999 | Moore |
| 6,048,332 A | 4/2000 | Duffy et al. |
| 6,090,118 A | 7/2000 | McGuckin |
| 6,111,614 A | 8/2000 | Mugura et al. |
| 6,159,196 A | 12/2000 | Ruiz |
| 6,193,735 B1 | 2/2001 | Stevens |
| 6,231,518 B1 | 5/2001 | Grabek et al. |
| 6,258,087 B1 | 7/2001 | Edwards et al. |
| 6,264,633 B1 | 7/2001 | Knorig |
| 6,273,882 B1 | 8/2001 | Whittier et al. |
| 6,290,675 B1 | 9/2001 | Vujanic et al. |
| 6,319,227 B1 | 11/2001 | Mansouri Ruiz |
| 6,402,745 B1 | 6/2002 | Wilk |
| 6,485,482 B1 | 11/2002 | Belef |
| 6,517,528 B1 | 2/2003 | Pantages et al. |
| 6,520,928 B1 | 2/2003 | Junior |
| 6,602,264 B1 | 8/2003 | McGuckin |
| 6,733,473 B1 | 5/2004 | Reifart et al. |
| 6,818,001 B2 | 11/2004 | Wulfman et al. |
| 6,846,412 B2 | 1/2005 | Hogan et al. |
| 6,852,118 B2 | 2/2005 | Shturman et al. |
| 6,926,725 B2 | 8/2005 | Cooke et al. |
| 7,037,316 B2 | 5/2006 | McGuckin et al. |
| 7,077,836 B2 | 7/2006 | Lary et al. |
| 7,083,643 B2 | 8/2006 | Whalen et al. |
| 7,211,073 B2 | 5/2007 | Fitzgerald et al. |
| 7,285,126 B2 | 10/2007 | Sepetka et al. |
| 7,402,155 B2 | 7/2008 | Palasis et al. |
| 7,419,482 B2 | 9/2008 | Nash et al. |
| 7,479,147 B2 | 1/2009 | Honeycutt et al. |
| 7,662,143 B2 | 2/2010 | Carrison et al. |
| 7,670,328 B2 | 3/2010 | Miller |
| 7,713,231 B2 | 5/2010 | Wulfman et al. |
| 7,731,986 B2 | 6/2010 | Wright et al. |
| 7,819,887 B2 | 10/2010 | McGuckin et al. |
| 7,862,575 B2 | 1/2011 | Tal |
| 7,909,836 B2 | 3/2011 | McLean et al. |
| 7,967,834 B2 | 6/2011 | Tal et al. |
| 8,038,664 B2 | 10/2011 | Miller et al. |
| 8,062,316 B2 | 11/2011 | Patel et al. |
| 8,122,917 B2 | 2/2012 | Harman et al. |
| 8,123,770 B2 | 2/2012 | Olsen et al. |
| 8,172,783 B1 | 5/2012 | Ray |
| 8,202,244 B2 | 6/2012 | Cohen et al. |
| 8,460,214 B2 | 6/2013 | Kuban et al. |
| 8,491,539 B2 | 7/2013 | Fojtik |
| 8,632,520 B2 | 1/2014 | Otley |
| 8,657,821 B2 | 2/2014 | Palermo |
| 8,690,833 B2 | 4/2014 | Belson |
| 8,696,645 B2 | 4/2014 | Tal et al. |
| 8,992,482 B2 | 3/2015 | Fojtik |
| 9,022,971 B2 | 5/2015 | Fojtik |
| 9,162,037 B2 | 10/2015 | Belson et al. |
| 9,375,216 B2 | 6/2016 | Tal et al. |
| 9,440,046 B2 | 9/2016 | Hobbs et al. |
| 9,457,153 B2 | 10/2016 | Marano et al. |
| 9,463,304 B2 | 10/2016 | Agah et al. |
| 9,480,467 B2 | 11/2016 | Marano et al. |
| 9,480,652 B2 | 11/2016 | Harman |
| 9,585,667 B2 | 3/2017 | Tal et al. |
| 9,700,347 B2 | 7/2017 | Shiber |
| 9,737,329 B2 | 8/2017 | Shturman |
| 9,924,957 B2 | 3/2018 | McGuckin et al. |
| 10,207,057 B2 | 2/2019 | Fojtik |
| 10,368,902 B2 | 8/2019 | Kessler et al. |
| 10,405,878 B2 | 9/2019 | Wasdyke et al. |
| 10,555,752 B2 | 2/2020 | Robertson et al. |
| 10,561,440 B2 | 2/2020 | Look et al. |
| 10,702,300 B2 | 7/2020 | Higgins et al. |
| 11,006,935 B2 | 5/2021 | Brandeis |
| 11,696,793 B2 | 7/2023 | Anderson et al. |
| 2001/0041909 A1 | 11/2001 | Tsugita et al. |
| 2002/0010418 A1* | 1/2002 | Lary ............... A61M 25/10 604/101.04 |
| 2002/0010487 A1 | 1/2002 | Evans et al. |
| 2002/0188276 A1 | 12/2002 | Evans et al. |
| 2003/0004568 A1 | 1/2003 | Ken et al. |
| 2003/0120256 A1 | 6/2003 | Lary et al. |
| 2003/0225435 A1 | 12/2003 | Huter et al. |
| 2004/0147934 A1 | 7/2004 | Kiester |
| 2004/0219028 A1 | 11/2004 | Demarais et al. |
| 2004/0254566 A1 | 12/2004 | Plicchi et al. |
| 2005/0033227 A1 | 2/2005 | Brodersen |
| 2005/0059931 A1 | 3/2005 | Garrison et al. |
| 2007/0016232 A1 | 1/2007 | St. Martin et al. |
| 2007/0239140 A1 | 10/2007 | Chechelski et al. |
| 2008/0097224 A1 | 4/2008 | Murphy et al. |
| 2008/0183129 A1 | 7/2008 | Silverman et al. |
| 2009/0105645 A1 | 4/2009 | Kidd et al. |
| 2009/0171284 A1 | 7/2009 | Burke et al. |
| 2010/0010521 A1 | 1/2010 | Kurrus |
| 2010/0217313 A1 | 8/2010 | Raabe et al. |
| 2011/0152683 A1 | 6/2011 | Gerrans et al. |
| 2012/0059309 A1 | 3/2012 | di Palma et al. |
| 2013/0030410 A1 | 1/2013 | Drasler et al. |
| 2013/0294189 A1 | 11/2013 | Myrick et al. |
| 2015/0126965 A1 | 5/2015 | Liungman |
| 2015/0190127 A1 | 7/2015 | Madsen et al. |
| 2016/0242790 A1 | 8/2016 | Brandeis |
| 2017/0119428 A1 | 5/2017 | Boyle et al. |
| 2019/0365469 A1 | 12/2019 | Efremkin |
| 2019/0374277 A1 | 12/2019 | Bagwell et al. |
| 2020/0101269 A1 | 4/2020 | Hayes et al. |
| 2020/0113575 A1 | 4/2020 | Wisnosky et al. |
| 2020/0113577 A1 | 4/2020 | Wisnosky et al. |
| 2020/0121280 A1 | 4/2020 | Marshall et al. |
| 2020/0246042 A1 | 8/2020 | Plowiecki et al. |
| 2020/0269019 A1 | 8/2020 | Rollins et al. |
| 2021/0022816 A1 | 1/2021 | DeBuys et al. |
| 2021/0177455 A1 | 6/2021 | Jamous |
| 2022/0211983 A1 | 7/2022 | Giasolli et al. |
| 2022/0296291 A1 | 9/2022 | Anderson |
| 2022/0370715 A1 | 11/2022 | Vatemacher et al. |

FOREIGN PATENT DOCUMENTS

| | | |
|---|---|---|
| JP | 2007301392 A | 11/2007 |
| JP | 2009254874 A | 11/2009 |
| JP | 5622938 B2 | 11/2014 |
| RU | 2699009 C1 | 9/2019 |
| RU | 196638 U1 | 3/2020 |
| WO | WO94/021177 A1 | 9/1994 |
| WO | WO99/004701 A1 | 2/1999 |
| WO | WO99/047056 A1 | 9/1999 |
| WO | WO01/008561 A1 | 2/2001 |

OTHER PUBLICATIONS

American Medical Association: Code change instructions: 5 pages; retrieved from the internet (https://www.ama-assn.org/print/pdf/node/3146) on Jul. 28, 2023.

American Medical Association; CPT code change applications; 5 pages; retrieved from the internet (https://www.ama-assn.org/practice-management/opt/cpt-code-change-applications) on Jul. 28, 2023.

(56) References Cited

OTHER PUBLICATIONS

Centers for Medicare & Medacaid Services; CMS-1751-F; 3 pages; retrieved from the internet (https://www.cms.gov/medicaremedicare-fee-service-paymentphysicianfeeschedpfs-federal-regulation-notices/cms-1751-f) on Jul. 28, 2023.

Centers for Medicare & Medicaid Services; Billing and coding: treatment of chronic venous insufficiency of the lower extremities: 10 pages; retrieved from the internet (https://www.cms.gov/medicare-coverage-database/view/article.aspx?articleID=58250&ver=11) on Jul. 28, 2023.

CV Technologies; Flebogrif; 5 pages; retrieved from the internet (https://cvtechnologies.in/flebogrif/) on Jul. 28, 2023.

Daniels et al.; Effectiveness of embolization or scierotherapy of pelvic veins for reducing chronic pelvic pain; Journal of Vascular and Interventional Radiology: 27(10); pp. 1478-1486;75 pages (Author Manuscript); Oct. 2016.

Janatmakan et al.; Effect of local fibrinogen administratiion on postoperative bleeding in open prostatectomy surgery; Anesthesiology and Pain Medicine; 8(3); e73983; 6 pages; Jun. 2018.

Phlebolymphology; Treatment options for pelvic congestion syndrome; 11 pages; retrieved from the internet (https://www.phlebolymphology.org/treatment-options-pelvic-congestion-syndrome/) on Jul. 28, 2023.

Picel et al.; Endovascular treatment of pelvic congestion syndrome; 5 pages; retrived from the internet (https://assets.bmctoday.net/evtoday/pdfs/et0418_F11_Picel.pdf) on Jul. 28, 2023.

Teleflex; Arrrow-trerotola; 12 pages; retrieved from the internet (https://studylib.net/doc/8350860/arrow-trerotola%E2%84%A2-ptd%C2%AE-p) on Jul. 28, 2023.

U.S. Food & Drug Administration: Center For Drug Evaluation and research: Varithena / Polidocanol Injectable Foam; 34 pages; retrived from the internet (https://www.accessdata.fda.gov/drugsatfda_docs/nda/2013/205098Orig1s000SumR.pdf) on Jul. 23, 2023.

U.S. Food & Drug Administration: 510(k) Premarket Notification: Clarivein Catheter; 3 pages; retrieved from the internet (https://www.accessdata.fda.gov/scripts/cdrh/cfdocs/cfpmn/pmn.cfm?ID=K071468) on Jul. 28, 2023.

U.S. Food & Drug; Organge book: approved drug products with therapeutic equivalence evaluations: Polidocanol (Varithena) Solutin 180MG/18ML (10MG/ML); 2 pages; retrieved from the internet (https://www.accessdata.fda.gov/scripts/cder/ob/patent_info.cfm?Product_No=001&Appl_No=205098&Appl_type=N) on Jul. 28, 2023.

U.S.Food & Drug Administration; Drug approval package:Varithena; 2 pages; retrieved from (https://www.accessdata.fda.gov/drugsatfda_docs/nda/2013/205098orig1s000toc.cfm) on Jul. 28, 2023.

Varithena; How varithena works; 5 pages; retrieved from the internet (https://www.varithena.com/en-us-hcp/how-it-works.html) on Jul. 23, 2023.

Varithena_Reimbursement Alert; 3 pages; Available as of Apr. 21, 2022—Wayback Machine Archive; retrived from the internet (https://web.archive.org/web/20220421190800/https://www.varithena.com/content/dam/varithena/hcp/4-3-reimbursement/varithena-2022-medicare-physician-fee-schedule-final-rule.pdf) on Jul. 28, 2023.

Golshan; U.S. Appl. No. 18/361,732 entitled "Catheters for the aspiration controlled delivery of closure agents," filed Jul. 28, 2023.

* cited by examiner

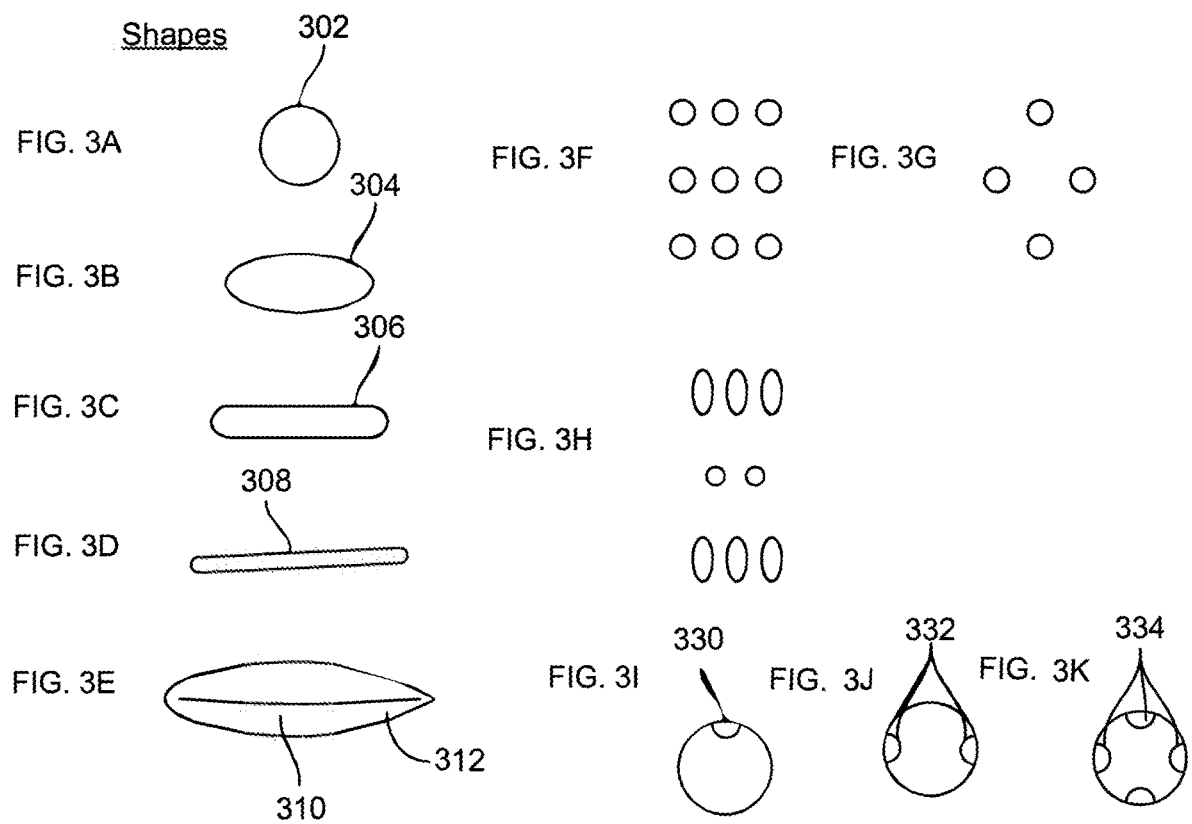

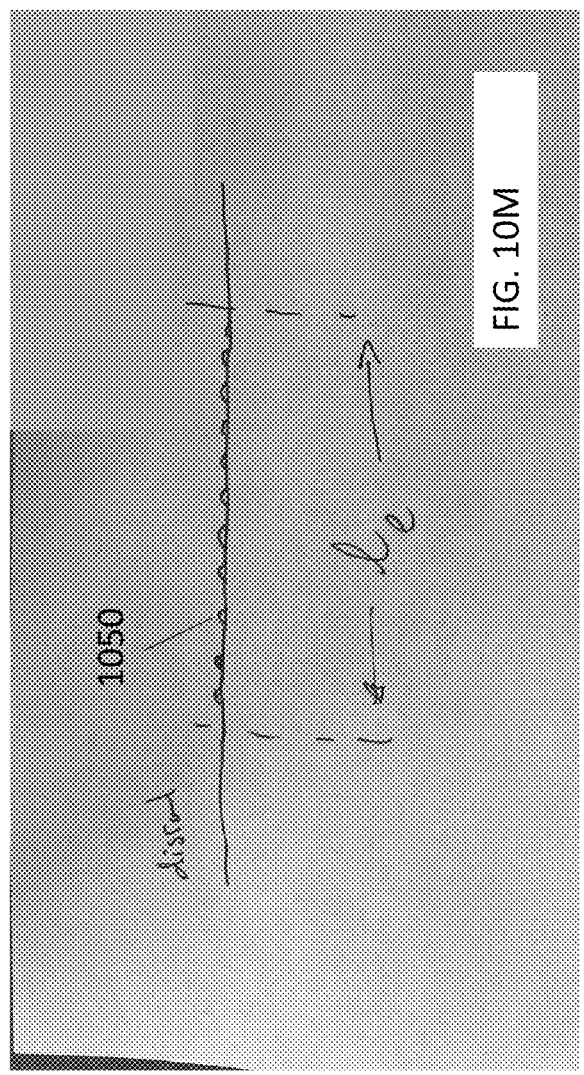

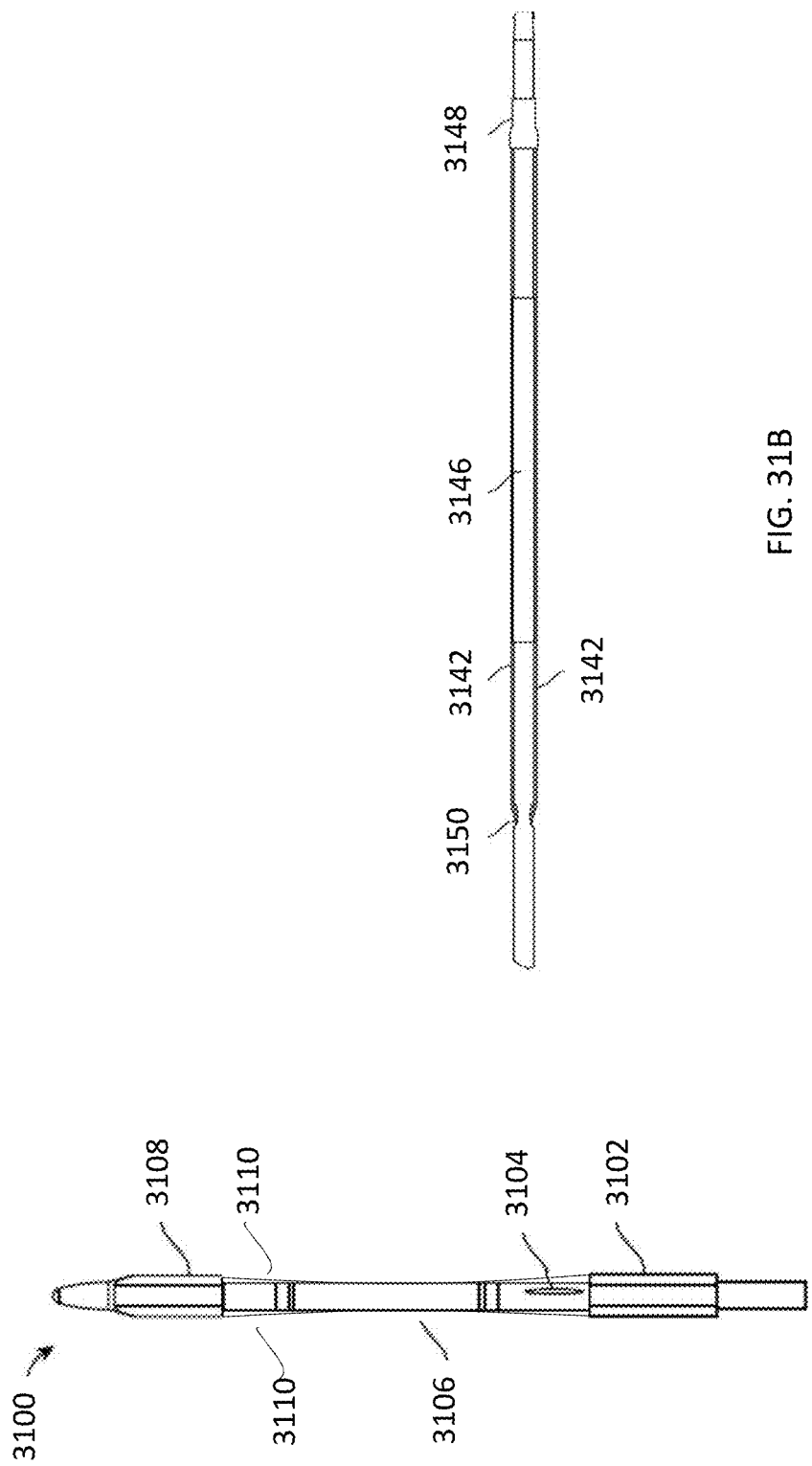

CATHETERS AND RELATED METHODS FOR THE ASPIRATION CONTROLLED DELIVERY OF CLOSURE AGENTS

RELATED APPLICATIONS

This application claims the benefit of U.S. Provisional Application No. 63/382,472, filed Nov. 4, 2022, the entire disclosure of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The subject matter disclosed herein generally relates to catheters for the controlled delivery of treatments within the venous vasculature of a mammal.

BACKGROUND

Circulatory issues may be addressed via invasive and non-invasive procedures. For example, currently superficial venous insufficiency (incompetent great saphenous veins) is treated with surgery or radiofrequency ablation (thermal ablation). This requires anesthesia, causes patient pain, and can cause nerve and skin injury. Alternatively, catheters are used to deliver diagnostic and therapeutic agents to internal sites that are typically accessed through the circulatory system in lieu of invasive procedures. For example, foam sclerotherapy (physician compounded) or other physician determined substance can be injected into the vein to cause it to scar shut. However, the injection of foam can lead to delivery of medication to unwanted areas (e.g., healthy veins) leading to injury of healthy veins, such as deep venous thrombosis (DVT) and thrombophlebitis (trapped blood in the treated diseased vein), which can lead to pain and skin injury.

Additionally, because of the distorted shape of the vessel to receive treatment, including distended portions, it is believed that conventional preparatory steps such as elevating the limb or massage of the limb do not sufficiently empty blood and fluids from the treatment zone. The result is that the effectiveness of any injected substance is at least questionable and most likely diminished because of an unknown dilution that occurs because of fluids retained in the limb to be treated.

For these and other reasons improvement in the treatment and delivery of material into diseased blood vessels is needed.

SUMMARY OF THE DISCLOSURE

In general in one embodiment, a method for closing a portion of a diseased vein in a patient, includes: accessing a portion of a venous vasculature of the patient with a balloon therapy device, advancing the balloon therapy device into a portion of the diseased vein, forming a proximal end of a closure zone in the diseased vein by inflating the balloon to a mechanical treatment pressure for engagement with an inner wall of the diseased vein, while maintaining the balloon at the mechanical treatment pressure, advancing the balloon therapy device along the diseased vein to a distal end of the closure zone, inflating the balloon to an occlusion pressure, while maintaining the balloon at the occlusion pressure, aspirating a portion of fluid from within the closure zone, injecting a closure agent into the closure zone, maintaining the balloon at the occlusion pressure until a closure agent dwell time has elapsed, deflating the balloon, and withdrawing the balloon therapy device from the patient.

In general in one embodiment, a method for closing a portion of a diseased vein in a patient, includes: accessing a portion of a venous vasculature of the patient with a balloon therapy device, advancing the balloon therapy device into a portion of the diseased vein, inflating the balloon to a vasospasm inducing/endothelium engaging pressure to form a proximal end of a closure zone in the diseased vein while maintaining the balloon at the vasospasm inducing pressure, advancing the balloon therapy device along the diseased vein to a distal end of the closure zone, inflating the balloon to an occlusion pressure, while maintaining the balloon at the occlusion pressure, aspirating a portion of fluid from within the closure zone using an aperture in fluid communication with the closure zone, injecting a closure agent into the closure zone using the aperture while maintaining the balloon at an occlusion pressure, maintaining the balloon at the occlusion pressure until a closure agent dwell time has elapsed; deflating the balloon, and withdrawing the balloon therapy device from the patient.

In general in one embodiment, a method for closing a portion of a diseased vein in a patient, includes: accessing a portion of a venous vasculature of the patient with a balloon therapy device, advancing the balloon therapy device into a portion of the diseased vein, inflating the balloon to transition a mechanical abrasion structure from a stowed configuration into a partially deployed configuration in contact with a wall of the diseased vein, while maintaining the mechanical abrasion structure in the partially deployed configuration, advancing the balloon therapy device along the diseased vein to a distal end of a closure zone, inflating the balloon to an occlusion pressure, while maintaining the balloon at the occlusion pressure, aspirating a portion of fluid from within the closure zone, injecting a closure agent into the closure zone, maintaining the balloon at the occlusion pressure until a closure agent dwell time has elapsed, and deflating the balloon to return the mechanical abrasion structure to a stowed configuration; and withdrawing the balloon therapy device from the patient. The mechanical abrasion structure in the partially deployed configuration forms a proximal end of the closure zone in the diseased vein. The partially deployed configuration one or more tissue engagement structures contact a wall the diseased vein.

In general, in one embodiment, a method for closing a portion of a diseased vein in a patient, includes: accessing a portion of a venous vasculature of the patient with a mechanical abrasion structure having one or more tissue engagement elements, advancing the mechanical abrasion structure into a proximal end of a closure zone of a diseased vein, transitioning the mechanical abrasion structure into a partially deployed configuration wherein one or more of the tissue engagement elements contact a wall of the diseased vein, advancing the mechanical abrasion structure along the diseased vein while maintaining the mechanical abrasion structure in the partially deployed configuration.

In still another variation, there is the step of stopping the advancing the mechanical abrasion structure step at a distal end of the closure zone and transitioning the mechanical abrasion structure into an occlusion configuration. Next, while maintaining the mechanical abrasion structure in an occlusion configuration, there is a step of aspirating a portion of fluid from within the closure zone, injecting a closure agent into the closure zone. There is also a step of maintaining the mechanical abrasion structure in an occlusion configuration until a closure agent dwell time has elapsed. Next, there is a step of transitioning the mechanical abrasion structure out of the occlusion configuration and withdrawing the mechanical abrasion structure from the patient.

In general, in one embodiment, a method for closing a portion of a diseased vein in a patient, incudes: advancing a guidewire into a portion of the diseased vein, advancing a dual balloon therapy device having a first balloon and a second balloon over the guidewire until the distal end of the distal balloon is positioned at a proximal end of a closure zone of the diseased vein. Partially inflating the first balloon and the second balloon to a mechanical treatment pressure in contact with an interior wall of the diseased vein, advancing the first and the second balloon along the diseased vein until the distal end of the close zone is reached.

In yet another embodiment, there is a step of inflating the first and the second balloons to an occlusion pressure and aspirating a fluid from the closure zone while maintaining the first and the second balloons at an occlusion pressure. Next, there is a step of injecting a closure agent into the closure zone in a space between the proximal end of the first balloon and the distal end of the second balloon. Thereafter, there is a step of maintaining the first balloon and the second balloon at the occlusion pressure until a closure agent dwell time has elapsed, and then, deflating the first balloon and the second balloon. At this point there is a step of withdrawing the dual balloon therapy device from the patient.

This and other embodiments can include one or more of the following features, the method can further include the step of aspirating a portion of fluid from within the closure zone is performed using an aperture proximal to the balloon, and the step of injecting a closure agent into the closure zone can be performed using the aperture. The method can further include coupling a syringe to a connector at a proximal end of the balloon therapy device outside of the patient vasculature before performing the aspiration step. The method can further include performing the injecting a closure agent step using the connector, the closure zone can be within a vein in a leg of the patient. The patient can be treated for pelvic congestion syndrome and at least a portion of the closure zone can be within a right ovarian vein or a left ovarian vein.

The patient can be treated for pelvic congestion syndrome and at least a portion of the closure zone can be within a right pelvic vein or a left pelvic vein. An aperture in a catheter shaft proximal to the treatment balloon is communication with a lumen that extends to the proximal end of the treatment device, further wherein the aspiration step and the injection step are performed using the aperture and the lumen. The method can further include a mechanical abrasion structure that moves from a stowed condition when the balloon is inflated and moves back to a stowed condition with the balloon is deflated. The method can further include: using an imaging modality to confirm the position of a distal portion of the device before a step of inflating the balloon, a step of advancing the device along a treatment zone, a step of aspirating a fluid from an orifice proximal to the balloon or a step of injecting. The step of using an imaging modality is one or a combination of ultrasound and x-ray.

In general, in one embodiment, an intravascular device, includes: a catheter shaft having a proximal end and a distal end, a hub coupled to the catheter shaft proximal end, a balloon on the catheter shaft adjacent to the distal end, an aperture in the catheter shaft at a spacing from a proximal end of the balloon, an inflation lumen within the catheter shaft in fluid communication with an interior volume of the balloon and an inflation port on the hub; and an fluid lumen within the catheter shaft in fluid communication with the aperture and a fluid port on the hub, wherein the spacing is less than a length of a closure zone of a diseased vessel.

This and other embodiments can include one or more of the following features. The length of a closure zone ranges from 5 cm to 50 cm in the legs and from 5 cm to 50 cm in the pelvis. The balloon inflates from a partially inflated diameter of from 3 mm to 14 mm and an occlusion diameter from 4 mm to 16 mm. The aperture has a largest dimension of from 1 mm to 10 mm. The aperture has a regular shape such as a circle, an oval, or an ellipse or an irregular or complex shape based on the based on optimization of aspiration and injection characteristics during use. More than one aperture arranged along or around the catheter shaft, wherein the apertures on a device have the same or different shapes or characteristics or are arranged in an ordered array. The device aperture can further include a covering with a slit to provide a valve like action to further adjust the characteristics during aspiration and injection. The device balloon can further include a wall engagement portion near area of largest expansion forming a localized area with a roughed surface, an array of raised features such as ribs, one or more dimples, spikes or other protrusions sized, shaped and arranged to engage the vessel wall for some level of damage that prompts the healing response or contact sufficient to cause vasospasm response and constriction along substantially all of the closure zone.

In general, in one embodiment, an intravascular device, includes: a catheter shaft having a proximal end and a distal end, a hub coupled to the catheter shaft proximal end, a balloon on the catheter shaft adjacent to the distal end, an atraumatic tip on catheter shaft distal end, an aperture in the catheter shaft proximal to the balloon, a collar at least partially encircling the catheter shaft, the collar positioned proximal to the aperture, a mechanical abrasion element having a tissue contacting surface, a balloon contacting surface, a distal end coupled to the atraumatic tip and a proximal end coupled to the collar, an inflation lumen within the catheter shaft in fluid communication with an interior volume of the balloon and an inflation port on the hub; and a fluid lumen within the catheter shaft in fluid communication with the aperture and a fluid port on the hub.

This and other embodiments can include one or more of the following features the device collar can fully encircle the catheter shaft, the tissue contacting surface can have a rough surface finish, the tissue contact surface can include one or more features to enhance tissue contact or engagement when the balloon is in a partially inflated condition, an external surface of the balloon can have a rough surface finish, a portion of the balloon external surface can have a rough surface finish that only contacts a vessel wall only after the balloon is at least partially inflated, the mechanical abrasion element is a first mechanical abrasion element, can further include: a second mechanical abrasion element having a tissue contacting surface, a balloon contacting surface, a distal end coupled to the catheter shaft distal end, and a proximal end coupled to the slide element wherein the first and the second abrasion elements are arranged in a circumferentially spaced apart orientation around the balloon.

The device can further include a circumferential arrangement of 2, 3, 4, 5, 6, 7, or 8 mechanical abrasion elements evenly spaced or irregularly spaced about the balloon, each one connected at a distal end to the atraumatic tip and at a proximal end to the collar. The device hub can further include a standard medical connector on the inflation port and a standard medical connector on the fluid port. The standard medical connector can be a Luer connector, a screw on connector or a locking valve. The hub is Y-shaped with the base coupled to the proximal end of the catheter shaft and an aperture in the first leg is the fluid port and an aperture in the second leg is the inflation port. At least a portion of the atraumatic tip, the mechanical abrasion element, the slider or the balloon can be visible using an imaging modality. The imaging modality can be ultrasound or x-ray or any other suitable medical imaging modality suited to the clinical situation.

The device can further include a second balloon on the catheter shaft proximal to the aperture and distal to the slider wherein the interior of the second balloon is in communication with the inflation port and the inflation lumen, the collar slides distally along the catheter shaft in response to inflation of the balloon against a portion of the mechanical abrasion element. In one aspect, the collar slides proximally along the catheter shaft in response to deflation of the balloon against a portion of the mechanical abrasion element.

In general, in one embodiment, an intravascular device, includes: a catheter shaft having a proximal end and a distal end, a hub coupled to the catheter shaft proximal end, a balloon on the catheter shaft adjacent to the distal end, an atraumatic tip on catheter shaft distal end, an aperture in the catheter shaft proximal to the balloon, a collar on the catheter shaft, the collar positioned proximal to the aperture, the collar having one or more sockets extending partially along the length of the collar, a mechanical abrasion element having a distal end coupled to the atraumatic tip and a proximal end in sliding arrangement within a socket, an inflation lumen within the catheter shaft in fluid communication with an interior volume of the balloon and an inflation port on the hub; and a fluid lumen within the catheter shaft in fluid communication with the aperture and a fluid port on the hub.

This and other embodiments can include one or more of the following features, the mechanical abrasion element can further include one or more of a tissue contacting surface and a balloon contacting surface. In still other aspects, there may be provided a collar that fully encircles the catheter shaft. In other aspects, the tissue contacting surface can have a rough surface finish, or the tissue contact surface includes one or more features to enhance tissue contact or engagement when the balloon is in a partially inflated condition. In another alternative, an external surface of the balloon has a rough surface finish. In another variation, a portion of the balloon external surface has a rough surface finish that only contacts a vessel wall only after the balloon is at least partially inflated. In still further implementations, the mechanical abrasion element is a first mechanical abrasion element and includes a second mechanical abrasion element having a tissue contacting surface, a balloon contacting surface, a distal end coupled to the catheter shaft distal end, and a proximal end coupled to the slide element wherein the first and the second abrasion elements are arranged in a circumferentially spaced apart orientation around the balloon.

The device can further include a circumferential arrangement of 2, 3, 4, 5, 6, 7, or 8 mechanical abrasion elements evenly spaced or irregularly spaced about the balloon, each one connected at a distal end to the atraumatic tip and at a proximal end to a correspondingly arranged socket formed in the collar. The device hub can further include a standard medical connector on the inflation port and a standard medical connector on the fluid port. In one aspect, the standard medical connector can be a Luer connector, a screw on connector or a locking valve. In other aspects, the hub is Y-shaped with the base coupled to the proximal end of the catheter shaft and an aperture in the first leg is the fluid port and an aperture in the second leg is the inflation port. In some aspects, at least a portion of the atraumatic tip, the mechanical abrasion element, the collar or the balloon is visible using an imaging modality. The imaging modality can be ultrasound or x-ray or any other suitable medical imaging modality suited to the clinical situation.

The device can further include a second balloon on the catheter shaft proximal to the aperture and distal to the slider wherein the interior of the second balloon is in communication with the inflation port and the inflation lumen and further wherein the length of the mechanical abrasion element is adjusted to extend from the atraumatic tip to a correspondingly positioned socket in the collar. In one aspect, the length of a collar socket can be longer than the amount of lateral movement of the mechanical abrasion element caused by the deflection of one or two balloons during inflation. In other aspects, the cross-section shape and size of the socket corresponds to the mechanical abrasion element cross section shape and size and is dimensioned to allow sliding movement of the mechanical abrasion element in response to the inflation and deflation of the one or two balloons of the device.

In general, in one embodiment, an intravascular device, includes: a catheter shaft having a proximal end and a distal end, a hub coupled to the catheter shaft proximal end, a first balloon on the catheter shaft adjacent to the catheter shaft distal end, and an aperture in the catheter shaft proximal to the first balloon, a second balloon on the catheter shaft proximal to the aperture wherein a distance between a proximal end of the first balloon and a distal end of the second balloon is a closure length, an atraumatic tip on catheter shaft distal end; and a collar on the catheter shaft, the collar positioned proximal to the second balloon, the collar having one or more sockets extending partially along the length of the collar. There is also one or more mechanical abrasion elements having a distal end coupled to the atraumatic tip and a proximal end in sliding arrangement within a corresponding socket in the collar; an inflation lumen within the catheter shaft in fluid communication with an interior volume of the first balloon, an interior volume of the second balloon and an inflation port on the hub; a fluid lumen within the catheter shaft in fluid communication with the aperture and a fluid port on the hub; and a guide wire lumen within the catheter shaft extending from the proximal end through the atraumatic tip.

This and other embodiments can include one or more of the following features, closure length is selected based on a closure procedure performed in the truncal veins, pelvic congestion, truncal venous insufficiency or a pelvic vein, the closure length is within a range from 5 cm to 50 cm; the first balloon and the second balloon may be inflated into a diameter from 3 mm to 14 mm for a partial inflation to contact a vein wall and a diameter ranging from 4 mm to 16 mm to act as an occlusion to a vein and, the catheter is 5 Fr or 6 Fr or 7 Fr having a length of 60 cm, 90 cm or 120 cm.

In general, in some embodiments, a method for closing a portion of a diseased vein in a patient is provided. The method comprises accessing a portion of a venous vasculature of the patient with a balloon therapy device; advancing the balloon therapy device into a portion of the diseased vein; forming a proximal end of a closure zone in the diseased vein by partially inflating the balloon to a mechanical treatment volume for engagement with an inner wall of the diseased vein; while maintaining the balloon at the mechanical treatment volume, advancing the balloon therapy device along the diseased vein to a distal end of a closure zone; inflating the balloon to occlude the diseased vein; while occluding the diseased vein, aspirating a portion of fluid from within the closure zone; injecting a closure agent into the closure zone; and maintaining occlusion in the diseased vein until a closure agent dwell time has elapsed.

These and other embodiments can include one or more of the following features. The method can further comprise deflating the balloon; and withdrawing the balloon therapy device from the patient. In some embodiments, advancing the balloon therapy device along the diseased vein to a distal end of the closure zone comprises injuring the endothelial layer and/or loss of endothelial cells of the diseased vein along the closure zone.

The method can comprise visualizing the balloon therapy device using an ultrasound probe. In some embodiments, the method comprises after the step of injecting a closure agent into the closure zone performing a step of applying a force from outside of the treatment zone to distribute the closure agent along the treatment zone. The step of applying force from outside of the treatment zone can be performed using an ultrasound probe and under ultrasound imaging. In some embodiments, the step of applying a force from outside of the treatment zone distributes the closure agent towards the proximal end of the closure zone and across at least one incompetent vein.

After the step of inflating the balloon to a mechanical treatment volume at least one mechanical abrasion element can be positioned between a surface of the balloon and a surface of the diseased vein. In some embodiments, injuring the endothelial layer is substantially performed by at least one mechanical abrasion element of a mechanical abrasion assembly.

In general, in some embodiments, a method for closing a portion of a diseased vein in a patient is provided. The method comprises accessing a portion of a venous vasculature of the patient with a balloon therapy device; advancing the balloon therapy device into a portion of the diseased vein; forming a proximal end of a closure zone in the diseased vein by partially inflating the balloon to a mechanical treatment volume for engagement with an inner wall of the diseased vein, wherein when the balloon is filled to the mechanical treatment volume within the diseased vein a length of the balloon along the diseased vein is greater than the width of the balloon across the diseased vein; while maintaining the balloon at the mechanical treatment volume, advancing the balloon therapy device along the diseased vein to a distal end of the closure zone; inflating the balloon to an occlusion volume causing the balloon to occlude the diseased vein at a distal end of a closure zone; while maintaining the balloon at the occlusion volume, aspirating a portion of fluid from within the closure zone; injecting a closure agent into the closure zone; and maintaining the balloon at the occlusion volume until a closure agent dwell time has elapsed.

These and other embodiments can comprise one or more of the following features. The method can further comprise deflating the balloon; and withdrawing the balloon therapy device from the patient. The method can comprise advancing the balloon therapy device along the diseased vein to a distal end of the closure zone comprises injuring only a portion of an endothelium of the diseased vein along the closure zone. In some embodiments, the method comprises visualizing the balloon therapy device using ultrasound while applying a force outside of the diseased vein to distribute the closure agent along the closure zone.

In general, in some embodiments, a method for closing a portion of a diseased vein in a patient is provided. The method comprises accessing a portion of a venous vasculature of the patient with a balloon therapy device, wherein the balloon is compliant; advancing the balloon therapy device into a portion of the diseased vein; inflating the balloon into a cylindrical shape at a proximal end of a closure zone to transition a mechanical abrasion structure from a stowed configuration into a partially deployed configuration in contact with a wall of the diseased vein; while maintaining the mechanical abrasion structure in the partially deployed configuration, advancing the balloon therapy device along the diseased vein to a distal end of a closure zone; inflating the balloon to occlude the diseased vein while aspirating a portion of fluid from within the closure zone; injecting a closure agent into the closure zone after aspirating a portion of the fluid within the closure zone; and continuing to occlude the diseased vein with the balloon until a closure agent dwell time has elapsed.

These and other embodiments can comprise one or more of the following features. The method can comprise deflating the balloon to return the mechanical abrasion structure to a stowed configuration; and withdrawing the balloon therapy device from the patient.

In some embodiments, the method further comprises visualizing a portion of the mechanical abrasion structures using ultrasound. The method can comprise visualizing the balloon therapy device using ultrasound while inflating the balloon the transition a mechanical abrasion structure from a stowed configuration into a partially deployed configuration in contact with a wall of the diseased vein.

In some embodiments, when the mechanical abrasion structure is in the partially deployed configuration one or more tissue engagement elements contact a wall of the diseased vein. The closure agent dwell time can be from 2-5 minutes. In some embodiments, the elapsed time from performing the step of advancing the balloon therapy device into a portion of the diseased vein to completing the step of withdrawing the balloon therapy device from the patient is less than 10 minutes.

The method can comprise advancing the balloon therapy device along the diseased vein to a distal end of a closure zone comprises injuring the endothelial layer and/or loss of endothelial cells of the diseased vein along the closure zone.

In some embodiments, the step of aspirating a portion of fluid from within the closure zone is performed using an aperture proximal to the balloon. The step of injecting a closure agent into the closure zone can be performed using the aperture. In some embodiments, the method comprises coupling a syringe to a connector at a proximal end of the balloon therapy device outside of the patient vasculature before performing the aspiration step. The method can comprise performing the injecting a closure agent step using the connector.

In some embodiments, the closure zone is within a vein in a leg of the patient.

The method can comprise using an imaging modality to confirm the position of a distal portion of the device before a step of inflating the balloon, a step of advancing the device along a treatment zone, a step of aspirating a fluid from an orifice proximal to the balloon or a step of injecting.

In some embodiments, an aperture in a catheter shaft proximal to the treatment balloon can be in communication with a lumen that extends to the proximal end of the treatment device, further wherein the aspiration step and the injection step are performed using the aperture and the lumen.

Inflating the balloon to transition a mechanical abrasion structure from a stowed configuration into a partially deployed configuration can comprise moving a portion of at least one mechanical abrasion element of the mechanical abrasion structure proximally along a dedicated mechanical abrasion element lumen of the balloon therapy device.

In some embodiments, advancing the balloon therapy device along the diseased vein to a distal end of a closure zone comprises advancing the balloon therapy device past at least one incompetent valve in the diseased vein.

In general, in some embodiments, an intravascular device is provided. The device comprises a catheter shaft having a proximal end and a distal end; a hub coupled to the catheter shaft proximal end; a balloon on the catheter shaft adjacent to the distal end, wherein the balloon is a compliant balloon; an atraumatic tip on catheter shaft distal end; an aperture in the catheter shaft proximal to the balloon; an inflation lumen within the catheter shaft in fluid communication with an interior volume of the balloon and an inflation port on the hub; a fluid lumen within the catheter shaft in fluid communication with the aperture and a fluid port on the hub; and a pair of mechanical abrasion elements extending along the catheter shaft and over the balloon, each of the pair of the mechanical abrasion elements having a tissue contacting surface and a balloon contacting surface, wherein at least a first section of each of the pair of the mechanical abrasion elements is configured to translate axially relative to the catheter shaft, and wherein inflation of the balloon causes at least a second section of each of the pair of the mechanical abrasion elements to extend away from the catheter shaft.

These and other embodiments can comprise one or more of the following features. The first section can be proximal to the balloon and each mechanical abrasion element of the pair of mechanical abrasion elements can comprise a distal end coupled to the catheter shaft at a location distal to the balloon. In some embodiments, the first section is distal to the balloon and each of the mechanical abrasion elements in the pair of mechanical abrasion elements comprises a proximal end coupled to the catheter shaft at a location proximal to the balloon. The catheter shaft can comprise a pair of mechanical abrasion element lumens, each one of the pair of mechanical abrasion element lumens formed in a sidewall of the catheter shaft positioned and sized to receive and guide axial movement of the first section of each of the mechanical abrasion elements relative to the catheter shaft. In some embodiments, the device comprises a pair of apertures in the catheter shaft in communication with each of the mechanical abrasion element lumens wherein in use the second section of each one of the pair of the mechanical abrasion elements extends from the balloon along the catheter shaft and into the respective aperture of each one of the pair of the mechanical abrasion element lumens.

In some embodiments, inflation of the balloon causes the first section of each of the mechanical abrasion elements positioned within the catheter shaft to slide distally and move through the aperture and outside the catheter shaft. Deflation of the balloon can cause the first section of each of the mechanical abrasion elements positioned outside the catheter shaft to slide proximally and move through the aperture and along the respective mechanical abrasion element lumen in the catheter shaft.

In some embodiments, the catheter shaft further comprises a pair of mechanical abrasion element lumens, each one of the lumens is sized to allow a mechanical abrasion element within the lumen to translate axially relative to the catheter shaft.

The device can comprise a collar fixing a distal most end of each one of the pair of the mechanical abrasion elements to the catheter shaft at a location distal to the balloon.

In some embodiments, the tissue contacting surface of each one of the pair of mechanical abrasion elements includes one or more features to enhance tissue contact or engagement when the balloon is in a partially inflated condition. An external surface of the balloon can have a rough surface finish.

In some embodiments, inflation and deflation of the balloon causes the first section of each of the pair of the mechanical abrasion elements to translate axially relative to the catheter shaft.

The hub can comprise a standard medical connector on the inflation port and a standard medical connector on the fluid port, wherein each of the standard medical connectors is one of a Luer connector, a screw on connector or a locking valve.

In general, in some embodiments, an intravascular device is provided. The device comprises a catheter shaft having a proximal end and a distal end; a hub coupled to the catheter shaft proximal end; a compliant balloon on the catheter shaft adjacent to the distal end; an atraumatic tip on catheter shaft distal end; an aperture in the catheter shaft proximal to the balloon; an inflation lumen within the catheter shaft in fluid communication with an interior volume of the balloon and an inflation port on the hub; a fluid lumen within the catheter shaft in fluid communication with the aperture and a fluid port on the hub; and a mechanical abrasion element assembly consisting of two wires extending along the catheter shaft and over the balloon, wherein at least a section of the two wires is configured to deflect radially outwardly alongside the balloon when the balloon is inflated and to deflect radially inwardly alongside the balloon when the balloon is deflated.

These and other embodiments can comprise one or more of the following features. The device can comprise the two wires positioned on opposite sides of the catheter shaft or a first wire of the two wires is positioned around the catheter shaft at a circumferential position of between 45-135° and a second wire of the two wires is positioned around the catheter shaft at a circumferential position between 225-315°. In some embodiments, the two wires comprise stainless steel, nitinol or a biocompatible metal. The two wires can comprise a length of about 70-180 mm and a diameter of about 0.1-0.6 mm. In some embodiments, the two wires comprise a cross-sectional shape that is generally circular, ovular, or rectangular.

The fluid lumen cam comprise a cross sectional area of about 0.2-0.32 mm and the inflation lumen can comprise a cross sectional area of about 0.2-0.32 mm.

In some embodiments, a proximal end of the two wires is configured to translate axially along the catheter outer surface or axially along a lumen within the catheter sidewall and the distal end of the two wires is fixed to an outer surface of the catheter shaft distal to the balloon; or a distal end of the two wires is configured to translate axially along the catheter outer surface or axially along a lumen within the catheter sidewall and the proximal end of the two wires is fixed to an outer surface of the catheter shaft proximal to the balloon.

At least a section of the two wires can be configured to deflect radially outwardly alongside the balloon has a length of at least 20 mm.

In some embodiments, a distal end of each of the two wires is coupled to the catheter shaft at a distance from 7 mm to 20 mm from a distal end of the balloon and a proximal end of each of the two wires is coupled to the catheter shaft at a distance from 12 mm to 25 mm from a proximal end of the balloon.

In general, in some embodiments, an intravascular device is provided. The device comprises a catheter shaft having a proximal end and a distal end; a hub coupled to the catheter shaft proximal end; a balloon on the catheter shaft adjacent to the distal end; an atraumatic tip on catheter shaft distal end; an opening in the atraumatic tip in communication with a guide wire lumen that extends from the opening to the hub; an aperture in the catheter shaft proximal to the balloon; an inflation lumen within the catheter shaft in fluid communication with an interior volume of the balloon and an inflation port on the hub; a fluid lumen within the catheter shaft in fluid communication with the aperture and a fluid port on the hub; a first mechanical abrasion element having a distal end, a tissue engagement portion and a proximal end; a second mechanical abrasion element having a distal end, a tissue engagement portion and a proximal end; a first mechanical abrasion element lumen within and extending along a sidewall of the catheter shaft and in communication with a first aperture formed in a sidewall of the catheter shaft; a second mechanical abrasion element lumen within and extending along a sidewall of the catheter shaft and in communication with a second aperture formed in a sidewall of the catheter shaft; and wherein a transition of the balloon from a deflated condition to a partially inflated condition causes an increase in the radial spacing between the tissue engagement element of the first mechanical abrasion element relative to the catheter shaft and the second mechanical abrasion element relative to the catheter shaft.

These and other embodiments can comprise one or more of the following features. In these and other embodiments, the transition of the balloon from a deflated condition to a partially inflated condition can cause translation along the catheter shaft of the distal end or the proximal end of the first mechanical abrasion element and translation along the catheter shaft of the distal end or the proximal end of the second mechanical abrasion element. Translation along the catheter shaft can be within and along the first mechanical abrasion element lumen and the second mechanical abrasion element lumen.

In some embodiments, one of the proximal end or the distal end of the first mechanical abrasion element has a cross section that conforms to a cross section of the first mechanical abrasion element lumen and the other of the proximal end or the distal end of the first mechanical abrasion element has at least one surface shaped to correspond to an outer radius of the catheter shaft and wherein one of the proximal end or the distal end of the second mechanical abrasion element has a cross section that conforms to a cross section of the second mechanical abrasion element lumen and the other of the proximal end or the distal end of the second mechanical abrasion element has at least one surface shaped to correspond to an outer radius of the catheter shaft. The tissue engagement portion of the first mechanical abrasion element can have an inner surface with a radius of curvature adapted to correspond to a radius of the balloon in a partially inflated condition or a fully inflated condition and the tissue engagement portion of the second mechanical abrasion element can have an inner surface with a radius of curvature adapted to correspond to a radius of the balloon in a partially inflated condition or a fully inflated condition. In some embodiments, the tissue engagement portion of the first mechanical abrasion element has an outer surface configured for controllable engagement with a vessel wall and the tissue engagement portion of the second mechanical abrasion element has an outer surface configured for controllable engagement with a vessel wall. The outer surface of the tissue engagement portion of the first mechanical abrasion element and the outer surface of the tissue engagement portion of the second mechanical abrasion element can further comprise one or more features to enhance tissue contact or engagement when the balloon is in a partially inflated condition.

In some embodiments, an angle between the first mechanical abrasion element lumen within and extending along a sidewall of the catheter shaft and the first aperture formed in a sidewall of the catheter shaft or an angle between the second mechanical abrasion element lumen within and extending along a sidewall of the catheter shaft and the second aperture formed in a sidewall of the catheter shaft is 90 degrees or between 10 degrees and 50 degrees.

In general, in some embodiments, a method for closing a portion of a diseased vein in a patient is provided. The method comprises accessing a portion of a venous vasculature of the patient with a balloon therapy device; advancing the balloon therapy device into a portion of the diseased vein; forming a proximal end of a closure zone in the diseased vein by inflating the balloon to a mechanical treatment pressure for engagement with an inner wall of the diseased vein; while maintaining the balloon at the mechanical treatment pressure, advancing the balloon therapy device along the diseased vein to a distal end of the closure zone; inflating the balloon to an occlusion pressure; while maintaining the balloon at the occlusion pressure, aspirating a portion of fluid from within the closure zone; injecting a closure agent into the closure zone; and maintaining the balloon at the occlusion pressure until a closure agent dwell time has elapsed.

These and other embodiments can comprise deflating the balloon; and withdrawing the balloon therapy device from the patient.

In general, in some embodiments, a method for closing a portion of a diseased vein in a patient is provided. The method comprises accessing a portion of a venous vasculature of the patient with a balloon therapy device; advancing the balloon therapy device into a portion of the diseased vein; inflating the balloon to transition a mechanical abrasion structure from a stowed configuration into a partially deployed configuration in contact with a wall of the diseased vein at a proximal end of a treatment zone; while maintaining the mechanical abrasion structure in the partially deployed configuration, advancing the balloon therapy device along the diseased vein to a distal end of a closure zone; inflating the balloon to an occlusion pressure; while maintaining the balloon at the occlusion pressure, aspirating a portion of fluid from within the closure zone; injecting a closure agent into the closure zone; and maintaining the balloon at the occlusion pressure until a closure agent dwell time has elapsed.

These and other embodiments can comprise one or more of the following features. These and other embodiments can comprise deflating the balloon to return the mechanical abrasion structure to a stowed configuration; and withdrawing the balloon therapy device from the patient. In some embodiments, the method comprises visualizing a portion of the balloon therapy device using ultrasound. The method can comprise visualizing the balloon therapy device using ultrasound while inflating the balloon the transition a mechanical abrasion structure from a stowed configuration into a partially deployed configuration in contact with a wall of the diseased vein. In some embodiments, the method comprises confirming contact between the mechanical abrasion structure and the wall of the diseased vein. The method can comprise the mechanical abrasion structure in the partially deployed configuration forming a proximal end of the closure zone in the diseased vein. In some embodiments, in the partially deployed configuration one or more tissue engagement structures contact a wall the diseased vein. The closure agent dwell time can be about 2-5 minutes. In some embodiments, the elapsed time from partial inflation to removal of the balloon therapy device from the patient is less than 10 minutes. Advancing the balloon therapy device along the diseased vein to a distal end of a closure zone can comprise partially injuring the endothelium. In some embodiments, the method comprises the step of aspirating a portion of fluid from within the closure zone is performed using an aperture proximal to the balloon. In some embodiments, the step of injecting a closure agent into the closure zone is performed using the aperture. The method can comprise coupling a syringe to a connector at a proximal end of the balloon therapy device outside of the patient vasculature before performing the aspiration step. In some embodiments, the method comprises performing the injecting a closure agent step using the connector. The closure zone can be within a vein in a leg of the patient. In some embodiments, an aperture in a catheter shaft proximal to the treatment balloon is communication with a lumen that extends to the proximal end of the treatment device, further wherein the aspiration step and the injection step are performed using the aperture and the lumen. The mechanical abrasion structure can move from a stowed condition when the balloon is inflated and moves back to a stowed condition with the balloon is deflated. In some embodiments, the method comprises using an imaging modality to confirm the position of a distal portion of the device before a step of inflating the balloon, a step of advancing the device along a treatment zone, a step of aspirating a fluid from an orifice proximal to the balloon or a step of injecting. The step of using an imaging modality can comprise using ultrasound. In some embodiments, inflating the balloon to transition a mechanical abrasion structure from a stowed configuration into a partially deployed configuration comprises moving a proximal portion of the mechanical abrasion element distally. In some embodiments, inflating the balloon to transition a mechanical abrasion structure from a stowed configuration into a partially deployed configuration comprises moving a portion of the mechanical abrasion element proximally along a lumen of the balloon therapy device. Inflating the balloon to transition a mechanical abrasion structure from a stowed configuration into a partially deployed configuration can comprise moving a proximal portion of the mechanical abrasion element from inside the catheter to outside the catheter through an abrasion element aperture. In some embodiments, inflating the balloon to transition a mechanical abrasion structure from a stowed configuration into a partially deployed configuration comprises moving a pair of wires in a proximal portion of the mechanical abrasion element distally within a pair of recesses of the balloon therapy device.

In general, in some embodiments, an intravascular device is provided. The device comprises a catheter shaft having a proximal end and a distal end; a hub coupled to the catheter shaft proximal end; a balloon on the catheter shaft adjacent to the distal end; an atraumatic tip on catheter shaft distal end; an aperture in the catheter shaft proximal to the balloon; an inflation lumen within the catheter shaft in fluid communication with an a fluid lumen within the catheter shaft in fluid communication with the aperture and a fluid port on the hub; a mechanical abrasion element extending along the catheter shaft and over the balloon, the mechanical abrasion element having a tissue contacting surface, a balloon contacting surface, wherein at least a section of the mechanical abrasion element is configured to translate axially relative to the catheter shaft, and wherein inflation of the balloon causes at least a portion of the mechanical abrasion element to extend away from the catheter shaft.

These and other embodiments can comprise one or more of the following features. The mechanical abrasion element can comprise a distal end coupled to the catheter shaft at a location distal to the balloon and a proximal end configured to move relative to the catheter shaft. In some embodiments, the mechanical abrasion element comprises a proximal end coupled to the catheter shaft at a location proximal to the balloon and a distal end configured to move relative to the catheter shaft. The mechanical abrasion element can comprise a distal end and a proximal end configured to float or move freely within their respective mechanical abrasion element lumens. In some embodiments, the device comprise an aperture on the catheter shaft proximal to the balloon, wherein the mechanical abrasion element extends from the balloon proximally along the catheter shaft and into the aperture. Inflation of the balloon can cause a portion of the mechanical abrasion element positioned within the catheter shaft to slide distally and move through the aperture and outside the catheter shaft. Deflation of the balloon can cause a portion of the mechanical abrasion element positioned outside the catheter shaft to slide proximally and move through the aperture and into the catheter shaft. In some embodiments, the catheter shaft further comprises a mechanical abrasion element lumen within which the mechanical abrasion element can translate axially relative to the catheter shaft. The device can comprise a collar fixing the mechanical abrasion element to the catheter shaft at a location distal to the balloon. In some embodiments, the device comprises a collar at least partially encircling the catheter shaft, the collar positioned proximal to the aperture, the collar configured to translate axially relative to the catheter shaft, and wherein a proximal portion of the mechanical abrasion element is fixed to the collar. In some embodiments, the collar fully encircles the catheter shaft. The device can comprise a second balloon on the catheter shaft proximal to the aperture and distal to the collar wherein the interior of the second balloon is in communication with the inflation port and the inflation lumen. In some embodiments, the collar slides distally along the catheter shaft in response to inflation of the balloon against a portion of the mechanical abrasion element. The collar can slide proximally along the catheter shaft in response to deflation of the balloon against a portion of the mechanical abrasion element. In some embodiments, the collar slides proximally along the catheter shaft in response to deflation of the balloon against a portion of the mechanical abrasion element. The device can comprise a collar at least partially encircling the catheter shaft, the collar having at least one or more sockets extending partially along the length of the collar, the one or more sockets configured to receive a proximal end of the mechanical abrasion element. In some embodiments, the mechanical abrasion element is configured to slide within the one or more sockets. The tissue contacting surface can have a rough surface finish. In some embodiments, the tissue contact surface includes one or more features to enhance tissue contact or engagement when the balloon is in a partially inflated condition. An external surface of the balloon can have a rough surface finish. In some embodiments, a portion of the balloon external surface has a rough surface finish that only contacts a vessel wall only after the balloon is at least partially inflated. Inflation and deflation of the balloon can cause the section of the mechanical abrasion element to translate axially relative to the catheter shaft. In some embodiments, the mechanical abrasion element is a first mechanical abrasion element, further comprising: a second mechanical abrasion element having a tissue contacting surface, a balloon contacting surface, and a distal end coupled to the location distal to the balloon, wherein the first and the second abrasion elements are arranged in a circumferentially spaced apart orientation around the balloon. The device can comprise a circumferential arrangement of 2, 3, 4, 5, 6, 7, or 8 mechanical abrasion elements evenly spaced or irregularly spaced about the balloon, each one connected at the location distal to the balloon. In some embodiments, the hub comprises a standard medical connector on the inflation port and a standard medical connector on the fluid port. The standard medical connector can be a Luer connector, a screw on connector or a locking valve. In some embodiments, the hub is Y-shaped with the base coupled to the proximal end of the catheter shaft and an aperture in the first leg is the fluid port and an aperture in the second leg is the inflation port. At least a portion of the atraumatic tip, the mechanical abrasion element, or the balloon can be visible using an imaging modality. In some embodiments, the imaging modality is ultrasound or x-ray.

In general, in some embodiments, an intravascular device is provided. The device comprises a catheter shaft having a proximal end and a distal end; a hub coupled to the catheter shaft proximal end; a balloon on the catheter shaft adjacent to the distal end; an atraumatic tip on catheter shaft distal end; an aperture in the catheter shaft proximal to the balloon; an inflation lumen within the catheter shaft in fluid communication with an interior volume of the balloon and an inflation port on the hub; a fluid lumen within the catheter shaft in fluid communication with the aperture and a fluid port on the hub; and a mechanical abrasion element consisting of two wires extending along the catheter shaft and over the balloon, wherein at least a section of the two wires is configured to deflect radially outwardly alongside the balloon when the balloon is inflated and to deflect radially inwardly alongside the balloon when the balloon is deflated.

These and other embodiments can comprise one or more of the following features. The two wires can be positioned on opposite sides of the catheter shaft. In some embodiments, a first wire of the two wires is positioned around the catheter shaft at a circumferential position of between 45-135° and a second wire of the two wires is positioned around the catheter shaft at a circumferential position between 225-315°. The two wires can comprise stainless steel or nitinol. The wires can comprise a generally round cross-sectional shape.

In general, in some embodiments, an intravascular device is provided. The device comprises a catheter shaft having a proximal end and a distal end; a catheter shaft having a proximal end and a distal end; a balloon on the catheter shaft adjacent to the distal end; an atraumatic tip on catheter shaft distal end; an aperture in the catheter shaft proximal to the balloon; an inflation lumen within the catheter shaft in fluid communication with an interior volume of the balloon and an inflation port on the hub; a fluid lumen within the catheter shaft in fluid communication with the aperture and a fluid port on the hub; and a mechanical abrasion element extending along the catheter shaft within a mechanical abrasion element lumen within the catheter shaft and exiting the catheter shaft through a mechanical abrasion element aperture to extend over the balloon, the mechanical abrasion element fixed to the catheter shaft at its distal end, wherein at least a section of the mechanical abrasion element is configured to translate axially relative to the catheter shaft, and wherein inflation of the balloon causes at least a portion of the mechanical abrasion element to extend away from the catheter shaft.

These and other embodiments can comprise one or more of the following features. The distal end of the mechanical abrasion element can be fixed to the catheter shaft with a collar.

In general, in some embodiments, an intravascular device is provided. The device comprises a catheter shaft having a proximal end and a distal end; a hub coupled to the catheter shaft proximal end; a balloon on the catheter shaft adjacent to the distal end; an atraumatic tip on catheter shaft distal end; an aperture in the catheter shaft proximal to the balloon; a collar on the catheter shaft, the collar positioned proximal to the aperture, the collar having one or more sockets extending partially along the length of the collar; a mechanical abrasion element having a distal end coupled to the atraumatic tip and a proximal end in sliding arrangement within a socket; an inflation lumen within the catheter shaft in fluid communication with an interior volume of the balloon and an inflation port on the hub; and a fluid lumen within the catheter shaft in fluid communication with the aperture and a fluid port on the hub.

These and other embodiments can comprise one or more of the following features. The mechanical abrasion element can comprise one or more of a tissue contacting surface and a balloon contacting surface. The collar can fully encircle the catheter shaft. In some embodiments, the tissue contacting surface has a rough surface finish. The tissue contact surface can include one or more features to enhance tissue contact or engagement when the balloon is in a partially inflated condition. An external surface of the balloon can have a rough surface finish. In some embodiments, a portion of the balloon external surface has a rough surface finish that only contacts a vessel wall only after the balloon is at least partially inflated. The mechanical abrasion element can be a first mechanical abrasion element, and the device can further comprise: a second mechanical abrasion element having a tissue contacting surface, a balloon contacting surface, a distal end coupled to the catheter shaft distal end, and a proximal end coupled to the slide element wherein the first and the second abrasion elements are arranged in a circumferentially spaced apart orientation around the balloon. The device can comprise a circumferential arrangement of 2, 3, 4, 5, 6, 7, or 8 mechanical abrasion elements evenly spaced or irregularly spaced about the balloon, each one connected at a distal end to the atraumatic tip and at a proximal end to a correspondingly arranged socket formed in the collar. In some embodiments, the hub comprises a standard medical connector on the inflation port and a standard medical connector on the fluid port. The standard medical connector can comprise a Luer connector, a screw on connector or a locking valve. In some embodiments, the hub is Y-shaped with the base coupled to the proximal end of the catheter shaft and an aperture in the first leg is the fluid port and an aperture in the second leg is the inflation port. At least a portion of the atraumatic tip, the mechanical abrasion element, the collar or the balloon can be visible using an imaging modality. The imaging modality can be ultrasound or x-ray. In some embodiments, the device comprises a second balloon on the catheter shaft proximal to the aperture and distal to the slider wherein the interior of the second balloon is in communication with the inflation port and the inflation lumen and further wherein the length of the mechanical abrasion element is adjusted to extend from the atraumatic tip to a correspondingly positioned socket in the collar.

BRIEF DESCRIPTION OF THE DRAWINGS

FIGS. 3A-3K illustrate various alternative aperture shapes, arrangements and circumferential positions.

FIG. 4A illustrates the balloon in a stowed condition and FIG. 4B illustrates the balloon in either a partially tissue engaged pressure or, alternatively, a full occlusion pressure depending upon application.

FIG. 6A shows the balloon therapy device in a stowed configuration with sliding collar spaced a distance x from the aperture used for aspiration and closure agent injection.

FIG. 11A is a perspective view. FIG. 11B illustrates a pair of sockets in a collar (mechanical abrasion elements removed). FIG. 11C illustrates a cross section view of the collar of FIG. 11B showing a pair of mechanical abrasion elements moving between a stowed and a deployed position along each respective socket.

FIG. 15B makes clear how the distended and damaged walls of varicose veins likely form difficult to drain pockets of blood and fluid. Advantageously, the active aspiration step removes this blood and other fluids to prevent dilution of closure agent when injected.

FIGS. 31A and 31B show embodiments of balloon therapy devices.

DETAILED DESCRIPTION

Figure 1:
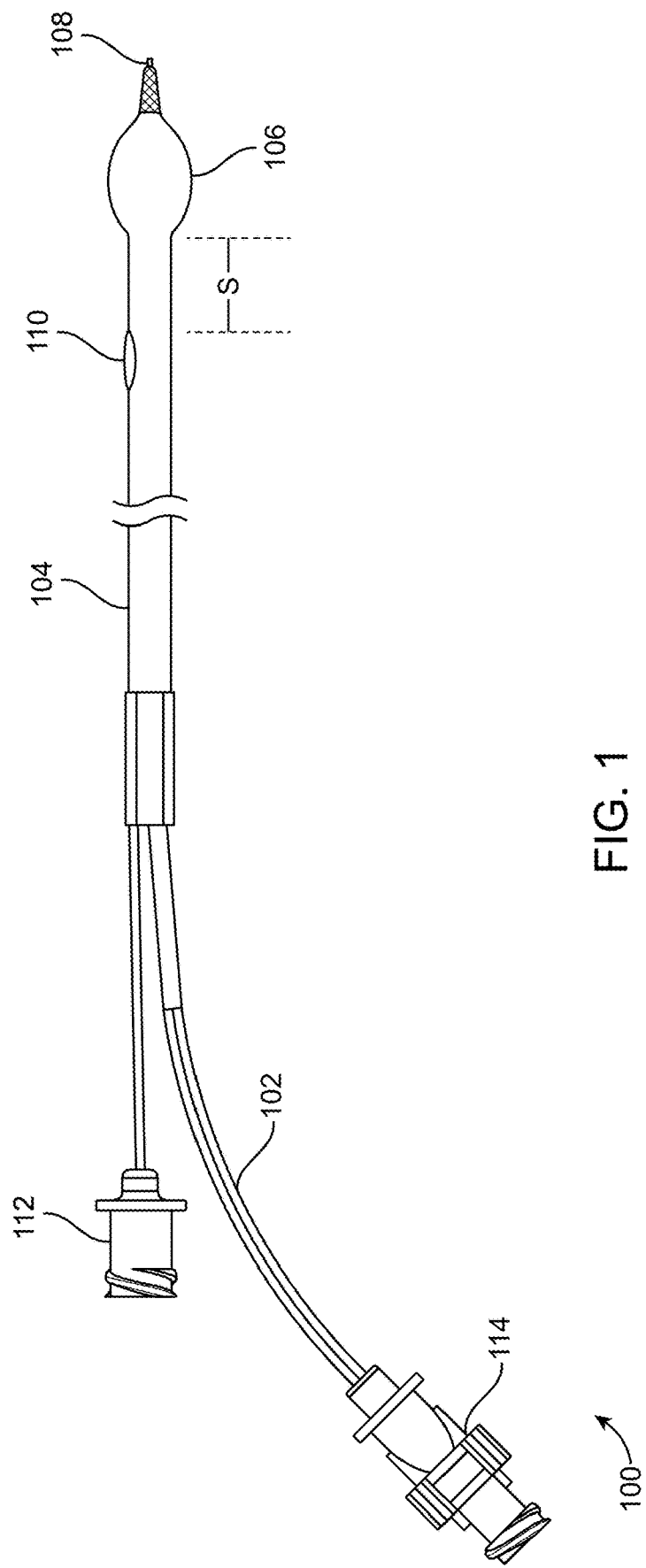
FIG. 1 is a perspective view of a balloon therapy device and hub according to one embodiment.

Briefly, and in general terms, various devices and related methods are directed to mechanical interaction with and/or irritation of a vessel wall to create a treatment zone, actively aspirating fluid from the treatment zone and thereafter injecting a pharmacologically active substance, closure agent, medicament, or other substance into the treatment zone for the desired pharmacological or physiological effect. Even minimal interaction with or irritation of the vessel wall can lead to venospasm or collapsing of the vein. Venospasm in combination with active aspiration allows for evacuation of blood from within the treatment zone. Evacuation of blood from the treatment zone can enhance the therapeutic effect of the closure agent. Such devices and methods can be used to treat, for example, varicose veins. Closure agent and closure zone include any of a wide variety of materials either formulated by a physician or as a prescribed agent. For example, foam sclerotherapy (physician compounded) or other physician determined sclerosant can be used as a closure agent. A wide range of closure agents are available and may be injected into the closure zone segment of the vessel to provide targeted delivery of medication.

The devices and methods disclosed herein provide significant advantages over current treatment for varicose veins. A first advantage is the increased control over the delivery of the medicament and reduced non-target delivery of medication, sclerosant, or chemotherapy agent. Currently, a clinician injecting a treatment agent into a vein needs to visualize the vein and the treatment agent extending along the vein during injection. If the treatment agent moves out of the treatment zone, the patient is at risk for blood clots, such as deep vein thrombosis. To prevent the treatment agent from traveling too far, the clinician needs to perform ultrasound guided external compression. The devices and methods described herein obviate this step as they create an isolated treatment zone, providing increased convenience and safety.

Another advantage provided by the current devices and methods is increased efficacy of the treatment agent allowed by the vein wall interaction and/or irritation and active aspiration. Treatment agents such as polidocanol are deactivated by blood. Currently, the clinician needs to elevate and massage the area to be treated in an effort to evacuate blood from the area. This step is both time consuming and ineffective. Actively aspirating the blood from the treatment area is a reliable and simple step to effectively evacuate blood from the area, which allows the polidocanol to more reliably and effectively treat the vein.

As described above, current treatment methods ineffectively evacuate blood from the area. When the treatment agent, such as polidocanol mixes with the remaining blood, it leads to clotted blood being trapped in the treated vein. Clinicians refer to this as trapped blood. The trapped blood can lead to thrombophlebitis, which is painful inflammation of a clotted vein. To treat, a clinician must perform an additional procedure called trapped blood aspiration, which involves numbing the skin and aspirating the trapped blood with an 18G needle and compressing the blood out of the vein. This procedure is very painful, but failure to perform this procedure can lead to permanent skin discoloration and staining. Devices and methods described herein significantly minimize the chance of needing this procedure.

As made clear above, the procedures using the devices and methods described herein are simpler from a technical perspective which means lower chance of complications and easier performance of the procedure. If a larger number of physicians can perform the procedure with the catheter, more patients may benefit from the treatment.

FIG. 1 is a perspective view of a balloon therapy device 100 and hub 102 according to one embodiment. The balloon therapy device comprises a catheter shaft 104. A balloon 106 is positioned near the distal end, proximal to the distal tip 108. The catheter shaft 104 comprises an aperture 110 positioned a spacing S proximal to the balloon 106. The spacing S can be from 5 mm to 10 mm or 15 mm-20 mm. The placement of the aperture 110 is to ensure coverage and aspiration of the closure zone most directly adjacent to the balloon 106.

Moving proximally, the device 100 comprises a hub 102 coupling a fluid port 112 and inflation port 114 to the device 100. The fluid port 112 and inflation port 114 can be connected to fluid and inflation lumens (not shown) extending through the catheter shaft 104. The fluid port 112 and inflation port 114 can comprise connectors configured for connection to a fluid and inflation source, respectively.

Figure 2:
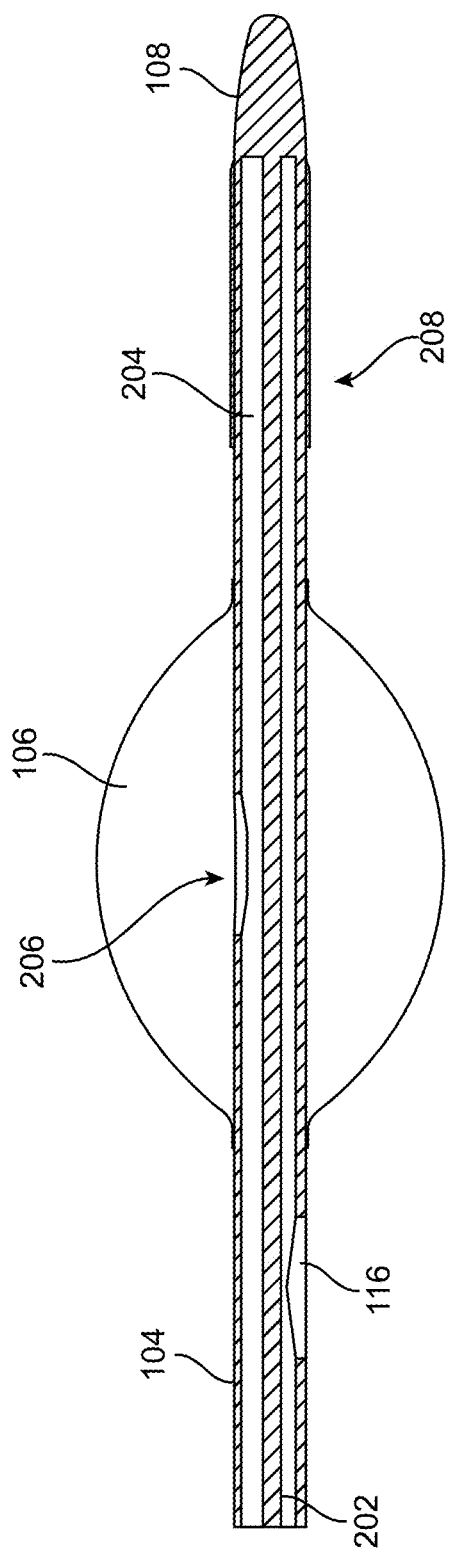
FIG. 2 is an enlarged section view of the distal end of the balloon therapy device of FIG. 1.

FIG. 2 is an enlarged section view of the distal end of the balloon therapy device of FIG. 1. In this view the fluid lumen 202 and inflation lumen 204 are shown extending along the catheter shaft 104. The fluid lumen is in communication with the aperture 110. The fluid lumen 202 is shown extending distal to the aperture 110, but it will be appreciated that, in some embodiments, it does not extend distal to the aperture 110. The balloon inflation lumen 204 is in communication with the balloon through an aperture 206 between the catheter shaft 104 and inflation lumen 204 at a location within the balloon 106. The inflation lumen is shown extending distal to the aperture 206, but it will be appreciated that, in some embodiments, it does not extend distal to the aperture 206.

The device 100 comprises an atraumatic distal tip portion 208. Distal to portion 208, the distal tip 108 tapers towards its end, providing a rounded, atraumatic leading end of the device 100. The distal tip 108 also seals off the fluid lumen 202 and the inflation lumen 204.

FIGS. 3A-3K illustrate various alternative aperture shapes, arrangements and circumferential positions. Alternative shapes of aperture 110 include a circle 302 (FIG. 3A), an oval 304 (FIG. 3B), a rounded rectangle 306 (e.g., rectangle with rounded corners) (FIG. 3C), a narrow slot 308 (FIG. 3D), a slit 310 in the covering 312, etc). It is to be appreciated that the aperture viewed in cross section may have walls that are the same diameter at the inner surface of the lumen and the outer surface of the catheter. Optionally, the width of the aperture at the inner surface of the lumen may be smaller than the width of the aperture at the outer surface of the catheter. In another alternative, the width of the aperture at the outer surface of the catheter may be smaller than the width of the aperture at the inner surface of the lumen.

FIGS. 3F-3H show additional variations 314, 316, 318 of the multiple holes or apertures along the length for delivery and aspiration. As shown in FIG. 3F, there can be multiple rows of the same type of aperture. In some embodiments, there can be a diamond pattern of the same type of aperture, as shown in FIG. 3G. In some embodiments, as shown in FIG. 3H, there can be a combination of different types of apertures.

Optionally or additionally, one or more apertures 110 may be provided with multiple holes that could be arranged around the perimeter. FIGS. 3I-3K show different embodiments of circumferential positioning of multiple holes. As shown in FIG. 3I, there may be a single hole 330 around the circumference of the catheter shaft. In some embodiments, as shown in FIG. 3J, there may be two holes 332 positioned around the circumference of the catheter shaft (e.g., generally equally spaced around the circumference of the catheter shaft). In some embodiments, as shown in FIG. 3K, there can be more than two holes 334 (e.g., four holes) positioned around the circumference of the catheter shaft (e.g., generally equally spaced around the circumference of the catheter shaft. Other configurations are also contemplated. There could also be only a single hole used for both aspiration and injection. The aspiration and injection holes may be provided in any combination of the above in any combination of FIGS. 3A-3K.

Figure 4A:
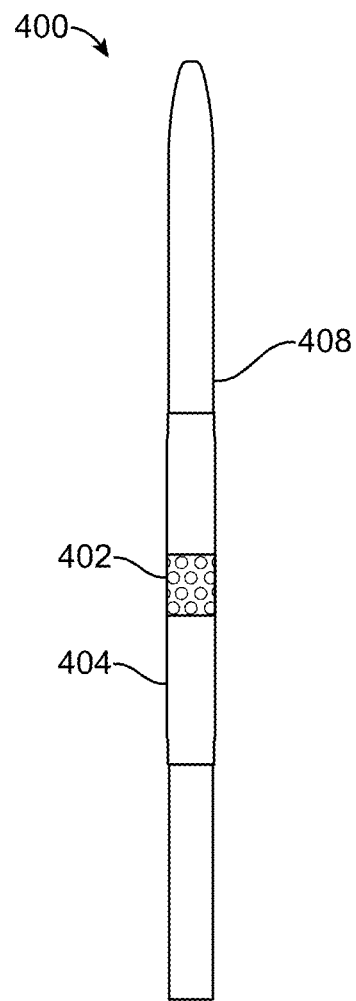
FIGS. 4A and 4B are side views of a distal portion of a balloon therapy device having a surface treatment in a tissue engagement section of an external surface of the balloon.
Figure 4B:
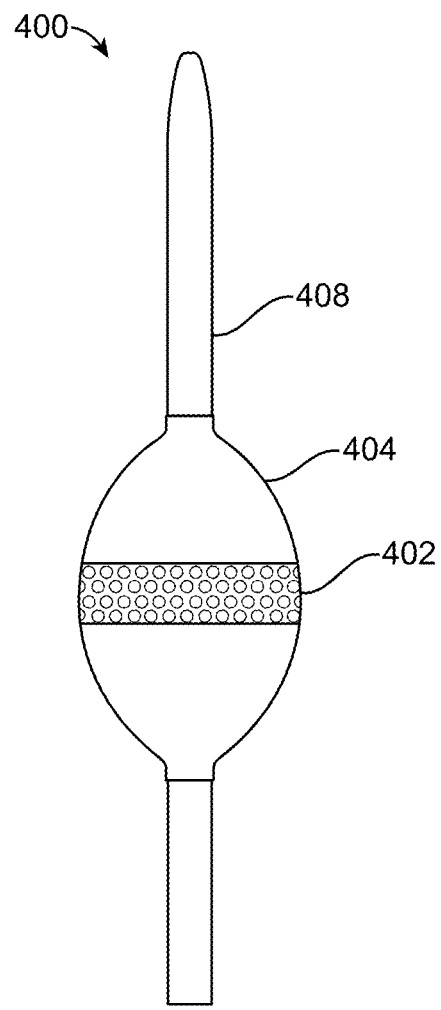

FIGS. 4A and 4B are side views of a distal portion of a balloon therapy device 400 comprising a catheter shaft 408 and a balloon 404 having a surface treatment. The surface treatment may be a zone of raised individual features like those shown in FIGS. 10A-F or of any suitable shape and size for desired level of engagement with the tissue wall. Additionally or optionally, the surface treatment may be a continuous or intermittent raised feature such as helical or spiral wrap, one or more or a series of continues or intermittent rings or hoops, portions of the surface that are roughened or bead blasted or otherwise treated to cause desired level of mechanical abrasion of the tissue, or combinations and modifications thereof. In one alternative, the tissue engagement section 402 is along an external surface of the balloon 404. FIG. 4A illustrates the balloon 404 in a stowed condition and FIG. 4B illustrates the balloon 404 in either a partially tissue engaged pressure or, alternatively, a full occlusion pressure depending upon application.

Figure 5B:
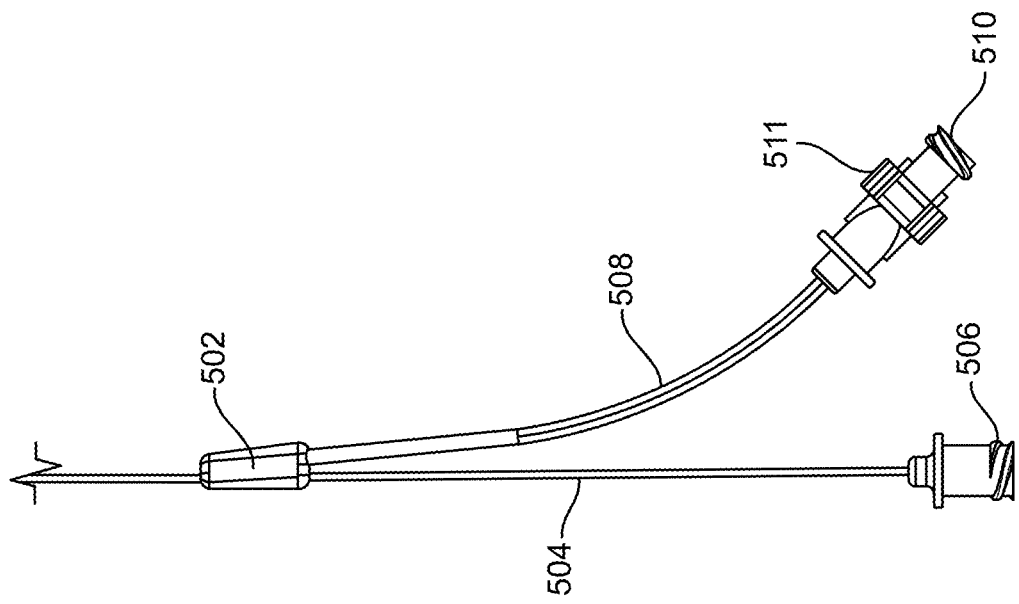
FIGS. 5A and 5B are alternative views of the proximal end of the balloon therapy device showing details of the connector hub.
Figure 5A:
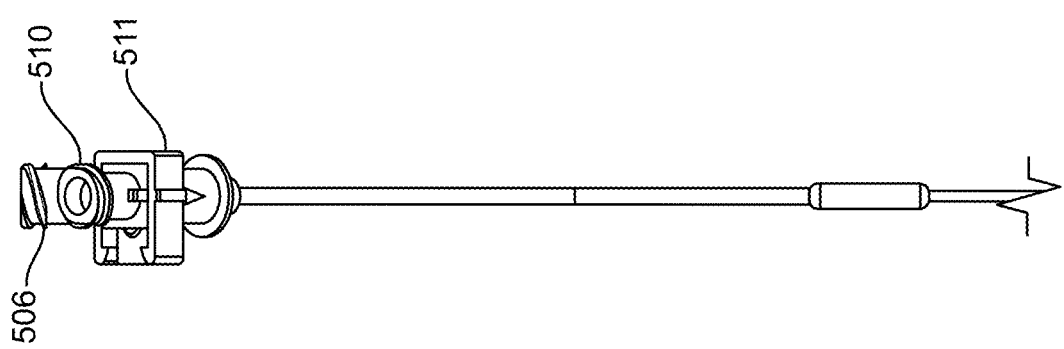

FIGS. 5A and 5B are top perspective and side views, respectively, of the proximal end of the balloon therapy device 500 showing details of the connector hub 502. Extending proximally from the connector hub 502 is a tube 504 connecting to a fluid port 506. This port 506 can be used, for example, for infusion of a closure agent or other treatment substance. In some embodiments, the port 506 comprises a Luer style connector. Also extending proximally from the connector hub 502 is a tube 508 connecting to an inflation port 510. The port 510 can comprise a Luer style connector. In some embodiments, the port 510 comprises a locking valve 511 to seal the inflation port at a desired inflation level of the balloon.

Figure 6B:
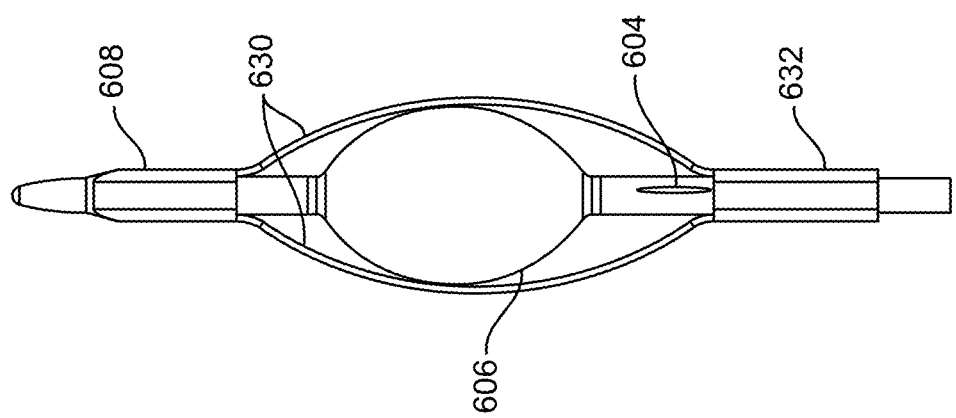
FIG. 6B is the balloon therapy device of FIG. 6A with the balloon inflated and the collar advanced distally along the catheter by about the distance x.
Figure 6A:
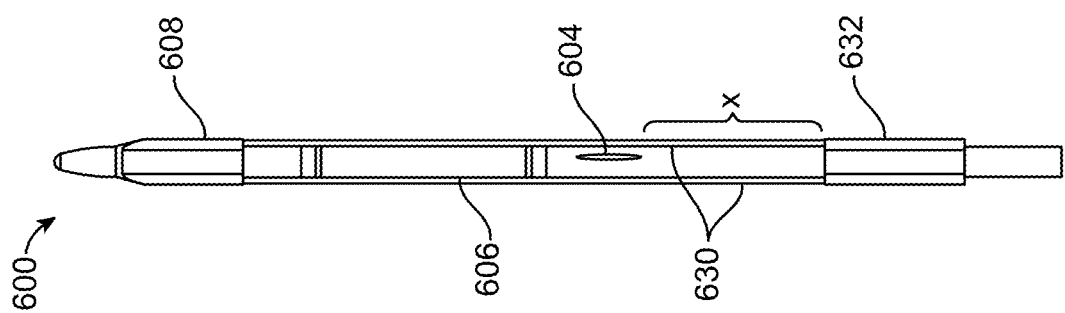
FIG. 6A is a side view of a balloon therapy device having mechanical engagement elements coupled to the atraumatic tip and a sliding collar.

FIG. 6A is a side view of a balloon therapy device 600 having mechanical abrasion elements coupled to the atraumatic tip 608 and a sliding collar 632. The device 600 comprises a catheter shaft 602, an aperture 604 (e.g., for aspiration and injection of closure agent), a balloon 606, and an atraumatic distal tip region 608. FIG. 6A shows the balloon therapy device 600 in a stowed configuration with sliding collar 632 spaced a distance x from the aperture 604 used for aspiration and closure agent injection, in this configuration. The distance x will vary based on the size of the balloon and the axial deflection of the sliding collar in use. The distance x is selected so that when the sliding collar is in the maximum distal position, the aperture 604 remains unobstructed.

FIG. 6B is the balloon therapy device 600 of FIG. 6A with the balloon 606 inflated and the collar 632 advanced distally along the catheter by about the distance x. Inflation of the balloon 606 causes the mechanical abrasion elements 630 to bow radially outward and shorten in an axial direction. This deflection pushes the mechanical abrasion elements 630 into the vessel wall.

In some embodiments, the sliding collar 632 is configured to be positioned proximally to the aperture 604 when the balloon is fully inflated to prevent blocking of the aperture. Other configurations (e.g., the collar being positioned distal to the aperture) are also contemplated.

Figure 7A:
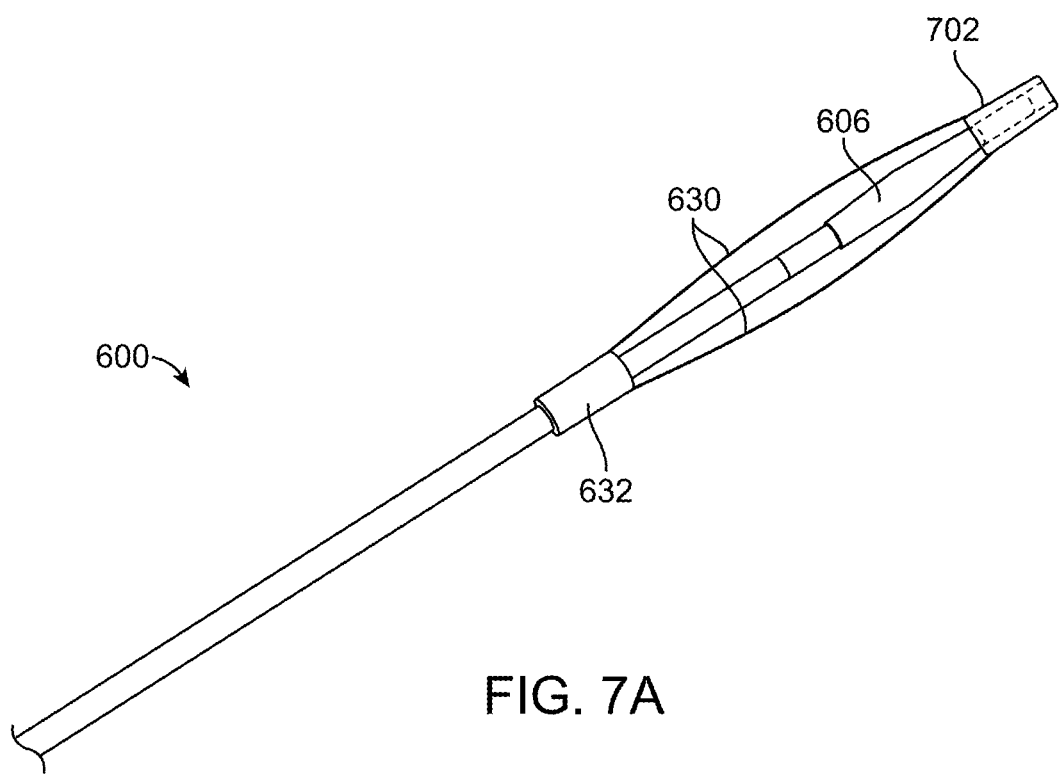
FIGS. 7A and 7B illustrate an alternative embodiment of the balloon therapy device of FIGS. 6A and 6B also in a stowed configuration (FIG. 7A) and a balloon inflated configuration (FIG. 7B).
Figure 7B:
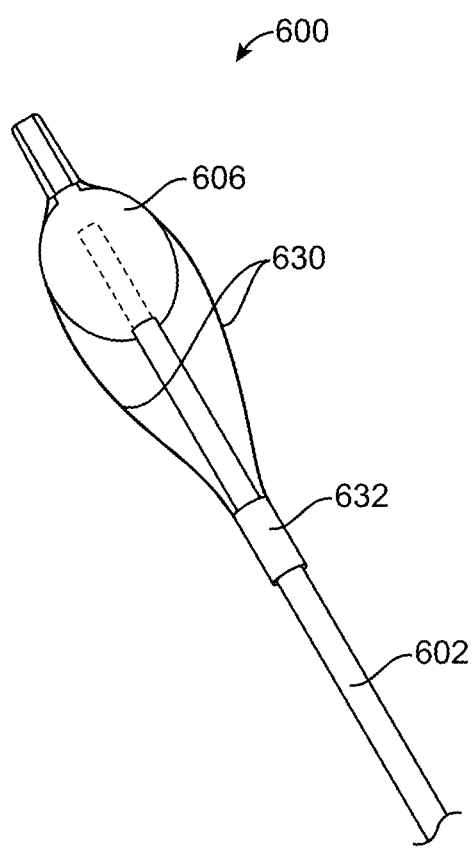

FIGS. 7A and 7B illustrate an alternative embodiment of the balloon therapy device 600 of FIGS. 6A and 6B. The device 600 comprises mechanical engagement elements 630 coupled to a sliding collar 632 positioned on the catheter shaft 602 and to the distal tip 702 of the device 600. The device is shown in a stowed configuration (FIG. 7A) and a balloon inflated configuration (FIG. 7B). As shown in the balloon inflated configuration of FIG. 7B, in some embodiments, the catheter shaft terminates in the balloon, proximal to the distal tip 702 when the balloon 606 is inflated.

Figure 8A:
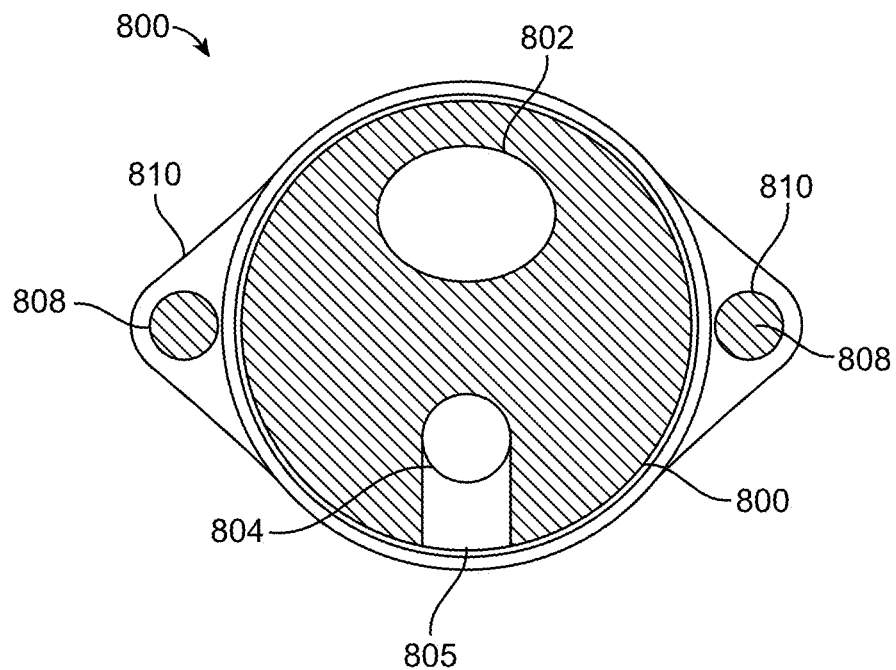
FIGS. 8A, 8B and 8C are various cross section views of the balloon therapy device and catheter providing additional details of the balloon inflation lumen and the aspiration and closure agent injection lumen.
Figure 8B:
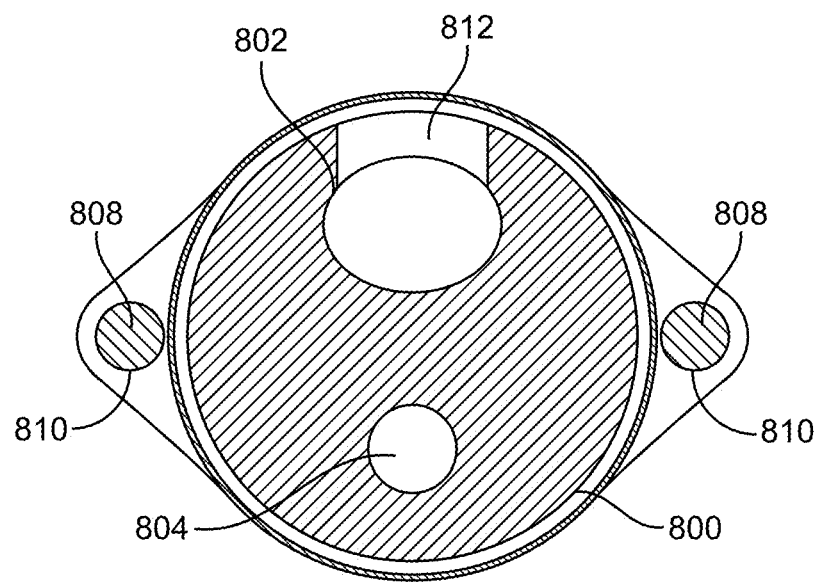
Figure 8C:
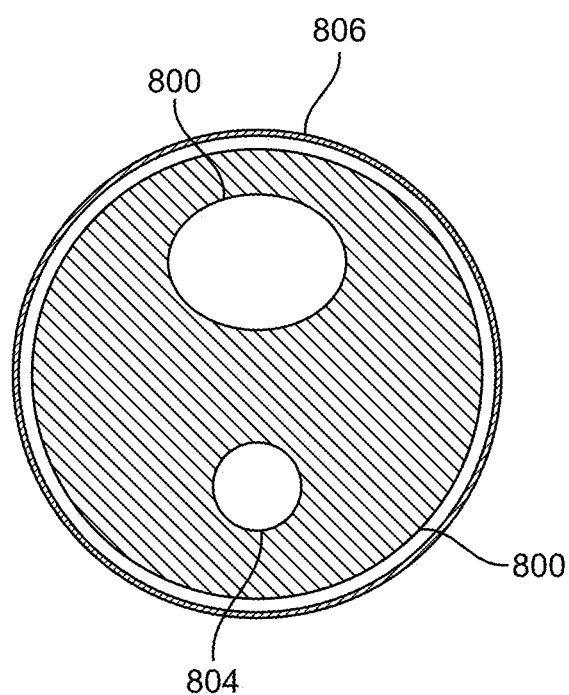

FIGS. 8A, 8B and 8C are various cross section views of the balloon therapy device and catheter 800 providing additional details of the catheter shaft, including the balloon inflation lumen and the aspiration and closure agent injection lumen.

Referring to FIG. 8A, a section view of the catheter shaft 800 is shown. Shown in this figure are the catheter shaft 800, a balloon inflation channel 802 and aspiration and injection channel 804 positioned within the catheter shaft 800. An aspiration and injection port 805 connects to the aspiration and injection channel 804. A balloon 806 surrounds the catheter shaft 800. Mechanical abrasion elements 808 are positioned along the catheter shaft. The abrasion elements 808 extend through adapters 810 connected to the catheter shaft 800.

FIG. 8B shows another embodiment of a section view of a catheter shaft 800. In this view, the balloon inflation port 812 is shown connected to the balloon inflation channel 802.

FIG. 8C shows yet another embodiment of a section view of a catheter shaft 800. This figure shows the balloon inflation channel 800 and aspiration and injection channel 804 positioned within the shaft 800. The balloon 806 is shown surrounding the shaft.

FIGS. 9A-9F provide exemplary steps of a method of forming a treatment zone and occluding a vessel and delivering a treatment agent. As will be discussed further below, additional details are provided below with respect to the methods 1800, 1900, 2000 shown in FIGS. 18, 19, and 20. These methods illustrate how a two step engagement with the diseased vein wall is used along with active aspiration of a closure section prior to injection of a closure agent. The diseased vessel has been illustrated as a cylinder so that the operation of the partial and occlusion deployment pressures and movement of the balloon therapy device may be more clearly presented. It is to be appreciated that the term mechanical treatment pressure refers to a level of contact between an inflated balloon in order to provide the desired level of engagement between a balloon therapy device and a wall of a vessel within a treatment zone. In many cases, this desired amount of contact is provided by controlling the volume of fluid injected into the balloon volume. It is also to be appreciated that, while the walls of the vein are shown as patent throughout the method of FIGS. 9A-9F, they may be subject to venospasm and collapse during the method.

Figure 9A:
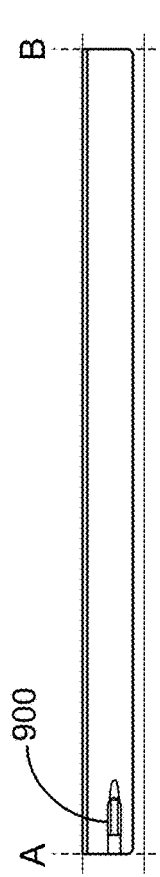
FIGS. 9A-9F provide exemplary steps of the method 1800 in FIG. 18 how a two step engagement with the diseased vein wall is used along with active aspiration of a closure section prior to injection of a closure agent. The diseased vessel has been illustrated as a cylinder so that the operation of the partial and occlusion deployment pressures and movement of the balloon therapy device may be more clearly presented.
Figure 9B:
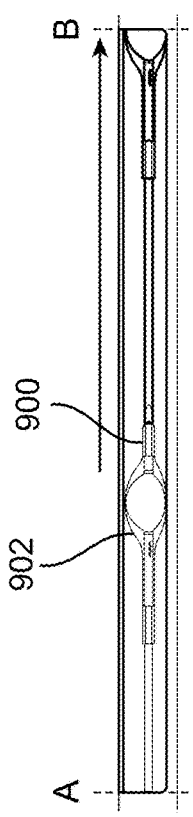

In FIG. 9A, the device 900 is inserted, in a stowed position, within the vein to a point A, the beginning point of vein segment A-B. In FIG. 9B, the device 900 is advanced in a direction indicated by the arrow toward point B, an ending point of the segment A-B. The mechanical abrasion elements 902 of the device engage the wall as the device advances towards point B.

During advancement of the device 900 from point A to point B, the balloon 904 may be at least partially inflated to engage the mechanical abrasion elements with the wall, in some embodiments.

In some embodiments, the balloon 904 is inflated, under ultrasonographic guidance, until the balloon makes contact with the vein wall. Once the clinician visualizes vein wall contact, the clinician may either stop inflation or inflate an additional small volume (e.g., about 0.25-0.50 cc). Such small additional inflation volumes may be needed to accommodate vessel wall elasticity or increases in vessel size.

It will be appreciated that, in some embodiments, engagement of the vessel wall with the mechanical abrasion elements may cause venospasm.

Figure 9C:
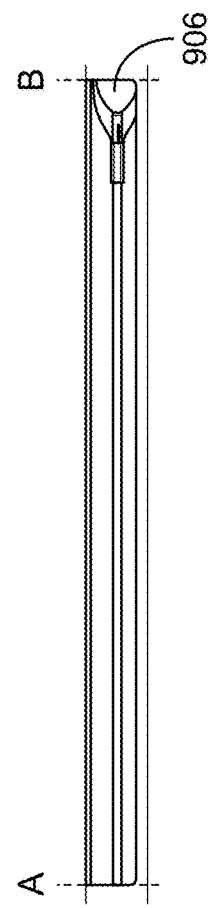

As shown in FIG. 9C, once the device has reached point B, the balloon 904 may be fully expanded, isolating the treatment area.

Expanding the balloon to its full volume can comprise inflating the balloon to about 2-3 cc.

Figure 9D:
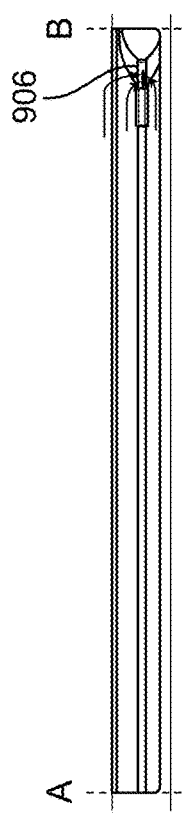

As shown in FIG. 9D, after isolation, blood and fluids can be aspirated from the treatment area (e.g., using aspiration and injection port 906 and lumen connected to a syringe).

Figure 9E:
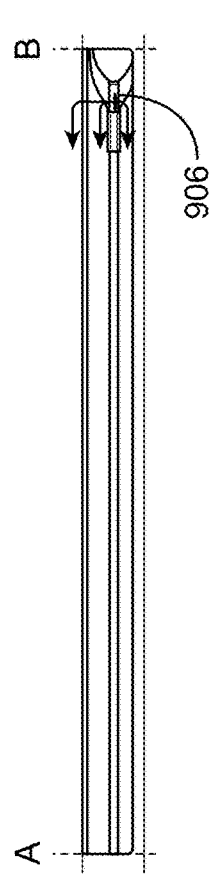

Moving to FIG. 9E, after aspiration, injection of a closure agent (e.g., foam) can be performed. The closure agent can be injected to the treatment area through, for example, the aspiration and injection port 906 and lumen.

In some embodiments, the closure agent is allowed to dwell at the treatment area for a period of time (e.g., 2-5 minutes).

Figure 9F:
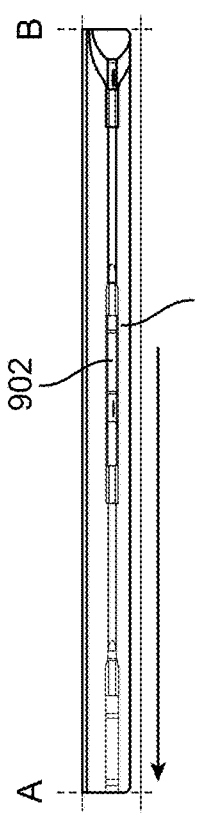

Once treatment is finished, the device is removed after deflating the balloon 904, thereby collapsing the abrasion elements 902, and next withdrawing the device as indicated by the arrow in FIG. 9F.

FIGS. 10A-H illustrate a variety of different cross section shapes of various alternative mechanical abrasion element embodiments and exemplary tissue engagement zone. A wide range of different features, textures or protrusions may be added to or formed in or provided on the abrasion elements. Such features may help facilitate vessel irritation, controlled or limited vessel wall damage, and facilitate venospasm. In one aspect, barbs may be formed in a layer placed over a portion of an abrasion element. FIGS. 10A-H show embodiments of features that can be arranged circumferentially about the balloon.

Figure 10A:
FIGS. 10A-10O illustrate a variety of different cross section shapes of various alternative mechanical abrasion element embodiments and exemplary tissue engagement zones.

Referring to FIG. 10A, one or more partial or whole rings or coils (or spiral(s) or helix(ces), etc.) can be arranged around the balloon.

Figure 10B:
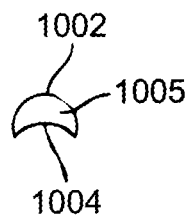

As shown in FIG. 10B, a crescent feature 1005 can be arranged on the balloon (e.g., conform to, sit on, be connected to, etc.). The tissue side 1002 can be configured to engage tissue while the balloon side 1004 can be configured to be arranged on the balloon.

Figure 10C:
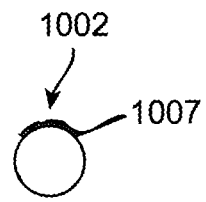

FIG. 10C shows a roughened surface 1007 on a tissue facing side 1002 of a balloon or feature configured to connect to a balloon.

Figure 10D:
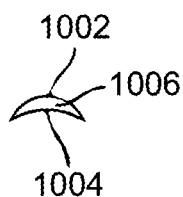

As shown in FIG. 10D, one or more fins or slats 1006 can be arranged around the balloon. The portion 1002 is configured to extend into the tissue, while the portion 1004 is configured to be arranged on (e.g., conform to, sit on, be connected to, etc.) the balloon.

Figure 10H:
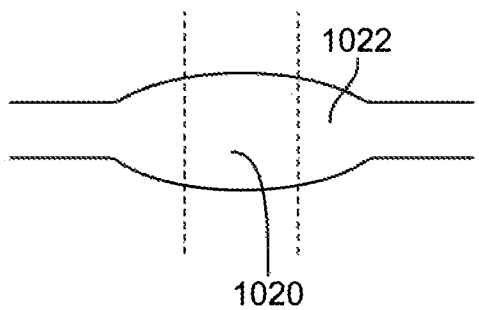
Figure 10E:
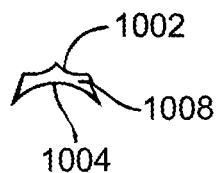
Figure 10I:
Figure 10J:

FIG. 10E shows pointed, barb like features 1008 that can be arranged about the balloon. In some embodiments, the features 1008 (and the other abrasion features described herein) are extruded. The barb features 1008 on the tissue side 1002 are configured to extend into the tissue while the side 1004 is configured to be arranged on the balloon.

Figure 10F:
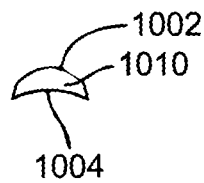
Figure 10K:
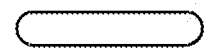
Figure 10L:
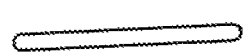

FIG. 10F shows a faceted feature 1010 that can be arranged about the balloon. The edge 1002 configured to extend into tissue can comprise two or more facets. The edge 1004 is configured to be arranged on the balloon.

Figure 10G:

FIG. 10G shows an embodiment of a raised spine 1012 that can be arranged around the balloon.

More than one circumferential abrasion element or an array of abrasion elements may be arranged about the balloon based on the desired level and pattern of engagement with tissue in the closure zone.

Figure 22:
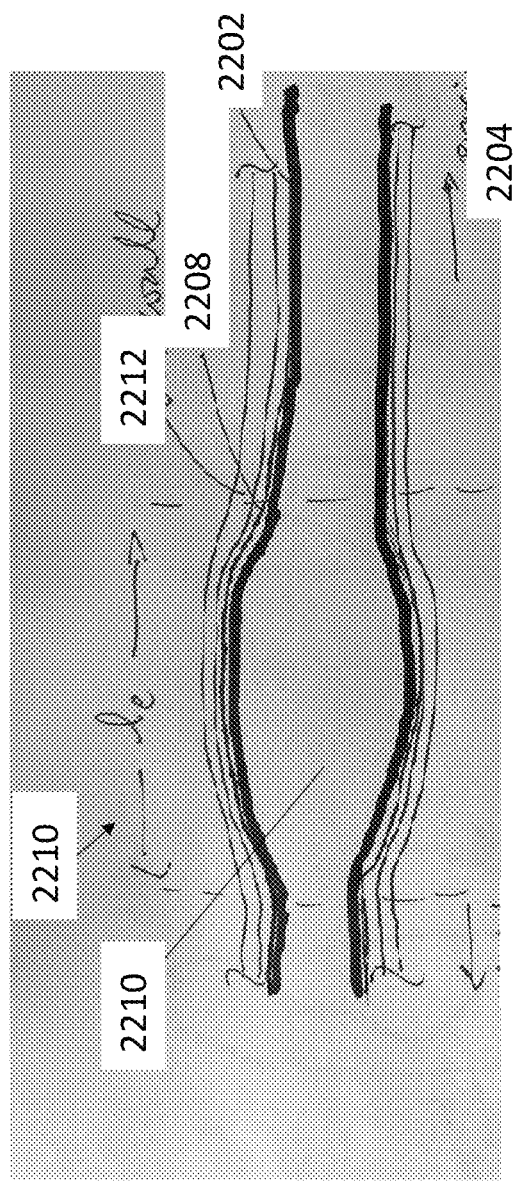
FIG. 22 shows another embodiment of a balloon therapy device 2200.

Additionally or optionally, the abrasion elements may also be arranged circumferentially around the balloon similar to the zone illustrated in FIGS. 4A and 4B. FIG. 10H shows a tissue engagement zone 1020 of a balloon 1022. When the balloon is inflated, because the zone 1020 inflates to the greatest diameter, it is this zone 1020 that comes into contact with the vessel wall. This zone can be the portion of the balloon comprising abrasion features configured to increase interaction and/or damage to the vessel wall, in some embodiments. Additionally or optionally, a compliant balloon embodiment may elongate within the vessel, for example as shown in FIG. 22, thereby forming a larger potential tissue engagement zone that would be larger than the engagement zones illustrated in FIGS. 4A and 4B.

FIGS. 10I-10L illustrate various embodiments of cross-sectional shapes for the mechanical abrasion elements. As shown in FIGS. 10I-10L, the mechanical abrasion element can comprise a circular shape (10I), an oblong shape (10J), a rounded rectangular shape (10K), a thinner rounded rectangular or ribbon like shape (10L). Other shapes are also contemplated (e.g., rectangular, etc.).

Referring now to FIG. 10M, the mechanical abrasion element can comprise a plurality of protrusions 1050 (e.g., hemispherical or other shaped bumps or barbs) along a portion of its length. The protrusions can be arranged along an engagement length $l_e$, a portion of the mechanical abrasion element configured to engage with the vein wall.

Figures 10N, 10O:
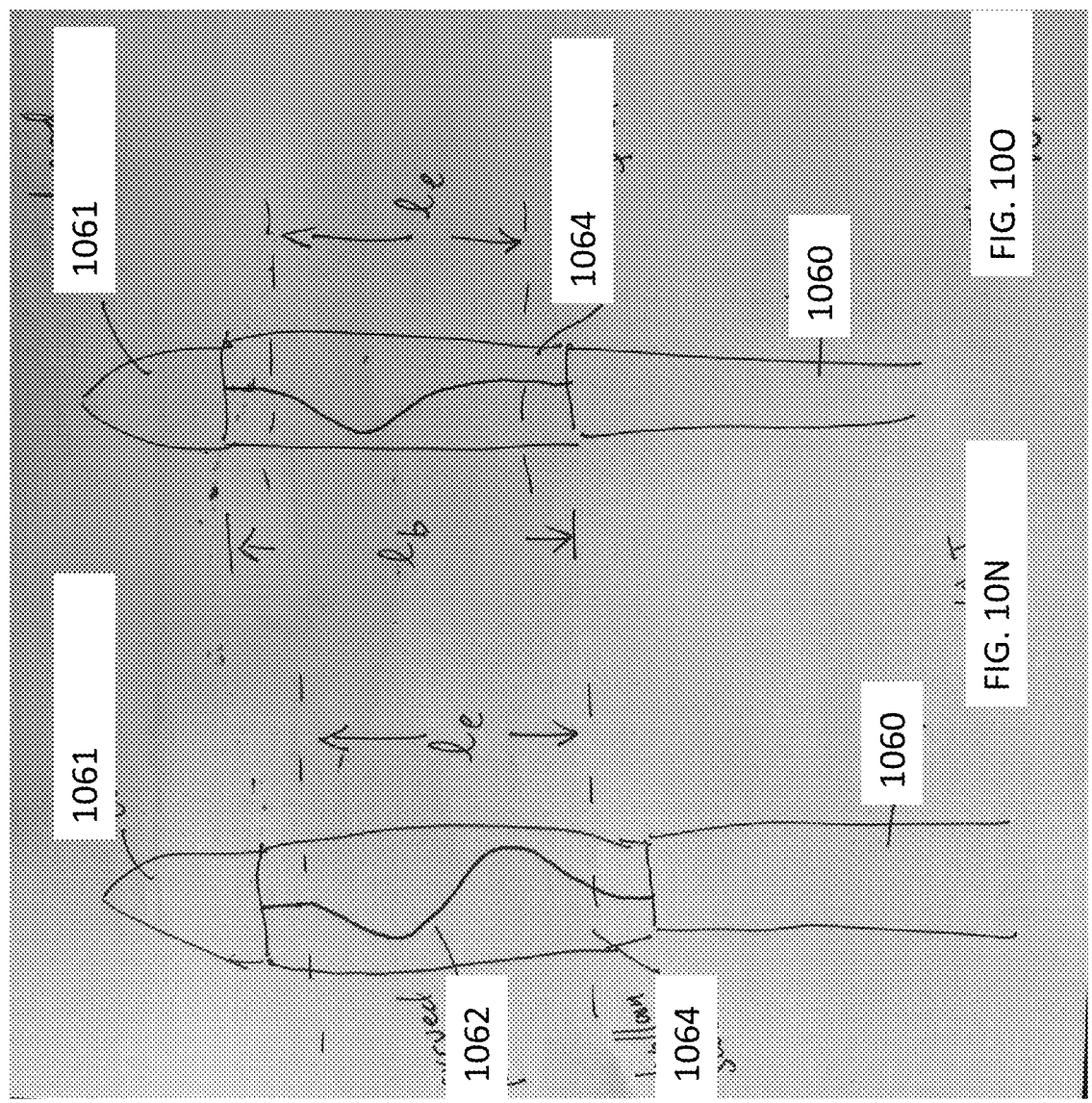

Moving to FIGS. 10N and O, the mechanical abrasion element can have a curved, undulating, or otherwise non-straight section 1062 along an engagement zone $l_e$ of the mechanical abrasion element. FIGS. 10N and 10O show the catheter shaft 1060, catheter shaft distal end 1061, and the balloon 1064. In comparison to a mechanical abrasion element that extends axially along the balloon, the mechanical abrasion element with the undulations or other non-axially extending portions has a greater effective abrasion zone since the non-axially extending portions have a greater area of contact between abrasion element and the vessel wall than the axially extending abrasion element. When the balloon expands, the undulations may stretch out, but maintain a non-linear shape to increase a surface area of engagement with the vein wall.

In one aspect, in order to minimize vessel wall interaction when navigating to the closure zone, the balloon outer surface may contain appropriately sized and spaced recesses to pocket the mechanical abrasion elements. Then, during inflation, the mechanical abrasion elements are urged out of the recess at the inflation of the balloon flattens the wall about the recessed portion thereby urging the mechanical abrasion element into contact with the vessel wall.

Figure 11A:
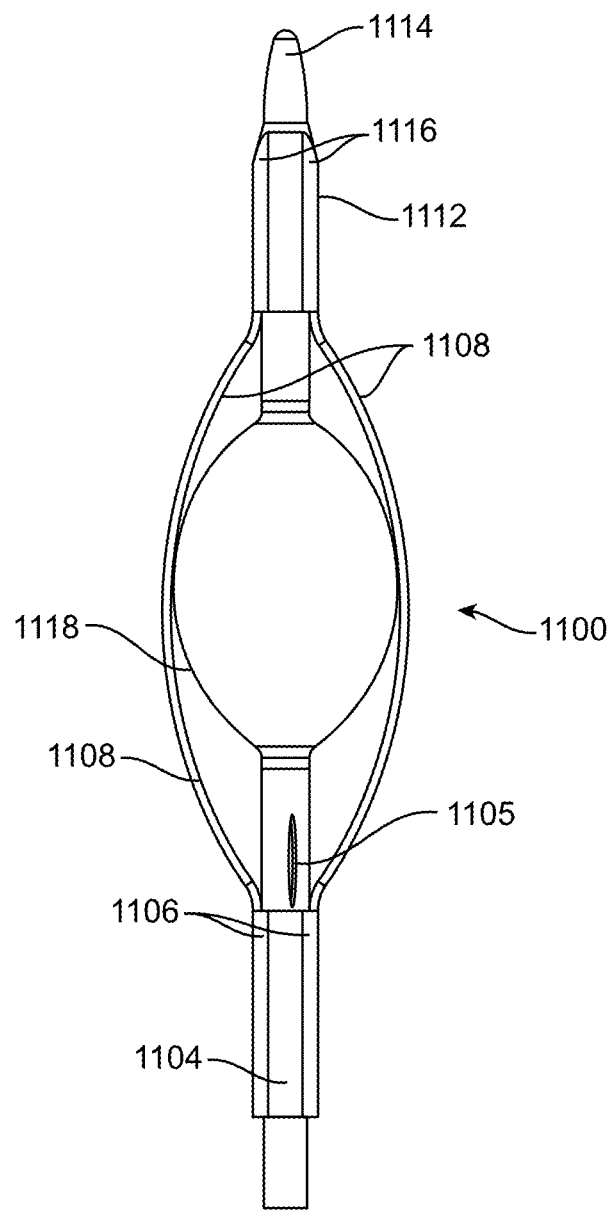
FIGS. 11A-11C are various views of a balloon therapy device having a fixed proximal collar with sockets to receive the proximal end of one or more mechanical abrasion elements.
Figure 11B:
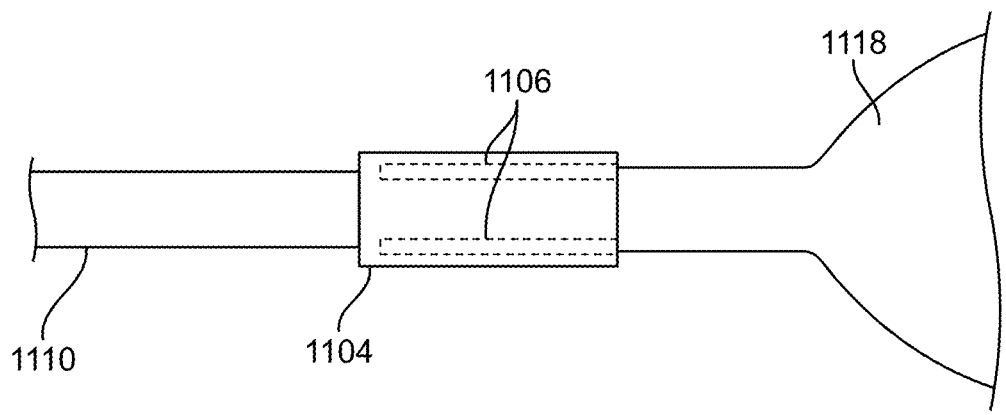
Figure 11C:
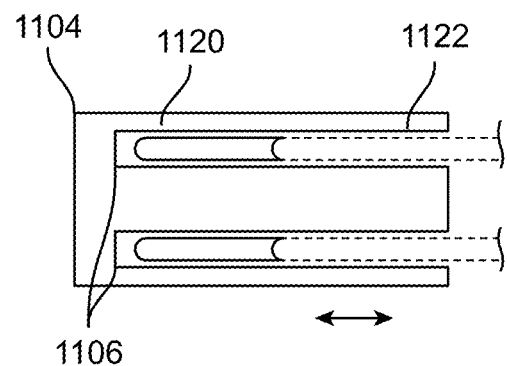

FIGS. 11A-11C are various views of a balloon therapy device 1100 having a fixed proximal collar 1104 with sockets 1106 to receive the proximal end of one or more mechanical abrasion elements 1108 (e.g., wire). FIG. 11A is a perspective view. Shown also in FIG. 11A are the catheter shaft 1110, around which the collar 1104 is arranged. A fluid aperture 1105 is positioned proximal to the balloon 1118. An atraumatic distal tip region 1112 is shown at the distal end 1114 of the device. The mechanical abrasion elements 1108 can be fixed at or near the distal tip region 1112, which can comprise sockets 1116 for receiving the mechanical abrasion elements 1108.

FIG. 11B illustrates a pair of sockets 1106 in a collar 1104 (mechanical abrasion elements removed), the collar positioned around a catheter shaft 1110. The sockets 1106 can comprise an elongated recess configured to receive a mechanical abrasion element. FIG. 11C illustrates a cross section view of the collar of FIG. 11B showing a pair of mechanical abrasion elements moving between a stowed and a deployed position along each respective socket. When the balloon 1118 is not inflated the mechanical abrasion elements are positioned in a stowed configuration 1120 at a proximal portion of the socket 1106. As the balloon 1118 inflates and the mechanical abrasion elements are pushed outwardly from the catheter shaft by the balloon, the proximal portion of the mechanical abrasion elements are pulled distally and move to a deployed configuration 1122 in a more distal portion of the socket, shown in dotted lines in FIG. 11C. The movement of the mechanical abrasion elements within the socket will vary based on the inflation volume of the balloon. Accordingly, the socket length is greater than the maximum expected deflection of the mechanical abrasion element so that, at all balloon diameters, the mechanical abrasion element remains within the socket.

Figure 12A:
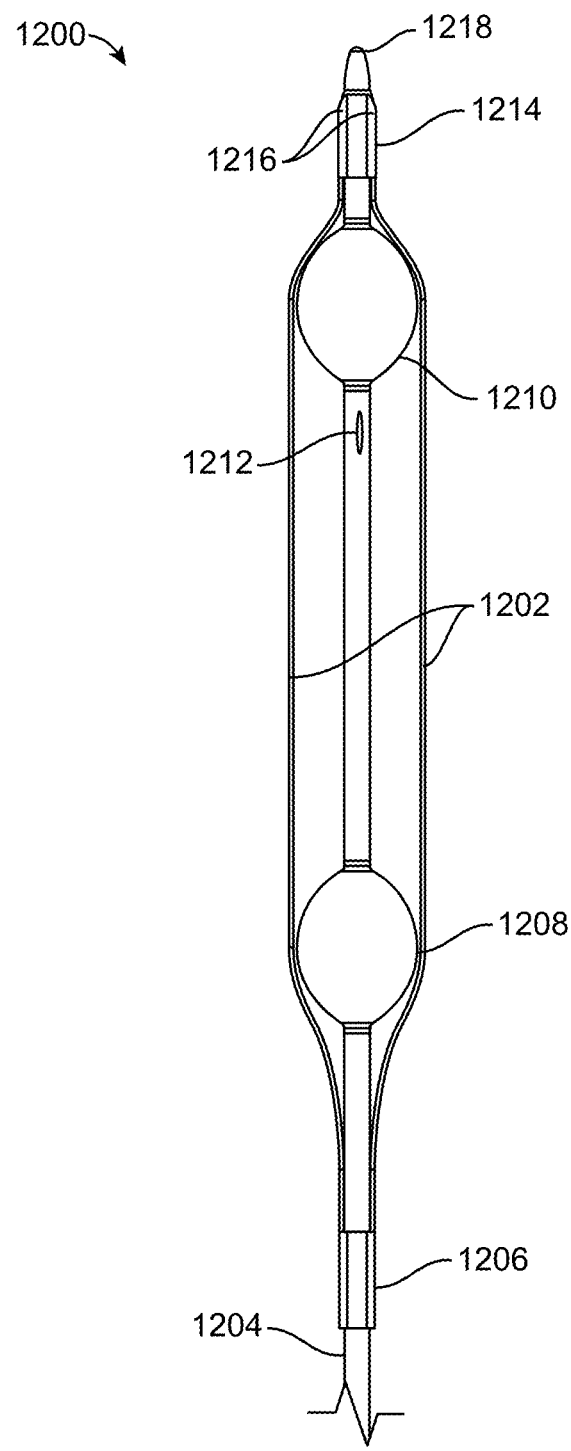
FIGS. 12A and 12C show an exemplary two balloon treatment device having mechanical abrasion elements. The socket may be of the moveable or the fixed configuration type. Use of a two-balloon treatment device is detailed in method 2000 in FIG. 20.
Figure 12B:
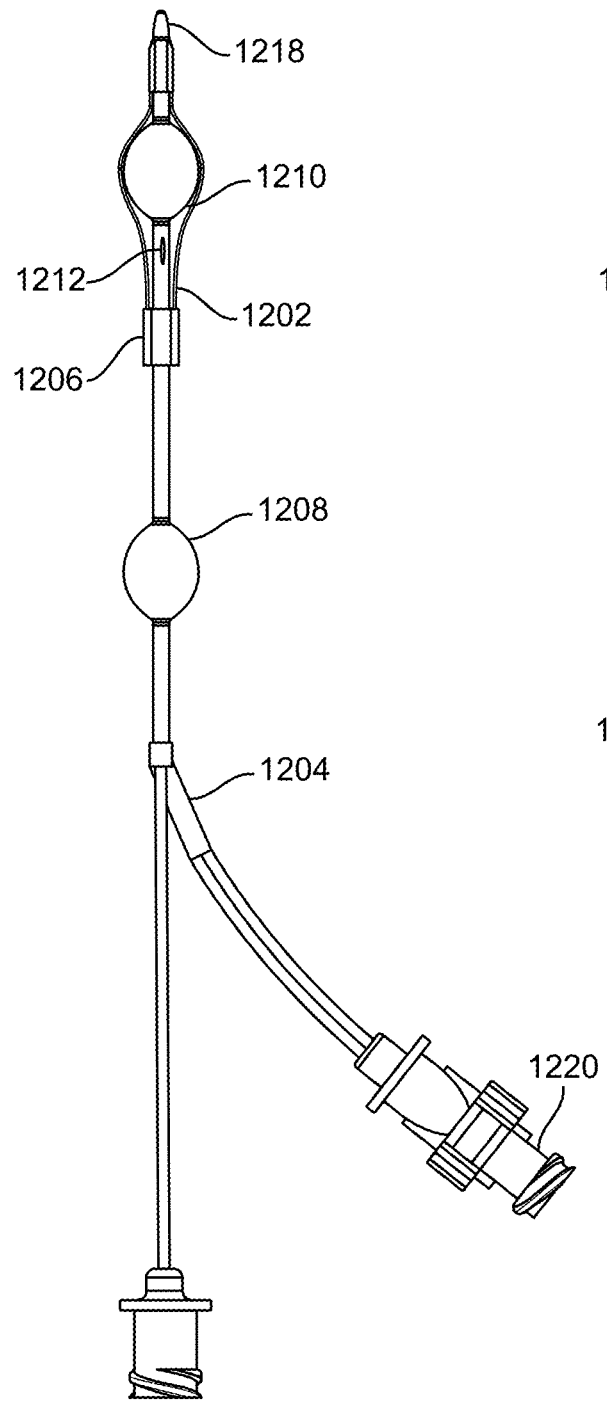
FIG. 12B is an exemplary two balloon treatment device having mechanical abrasion elements only on the distal balloon. This embodiment also includes a modified connector hub having separate inflation ports, one for the distal balloon and one for the proximal balloon. One or more of the steps of FIG. 20 method 2000 may be modified to accommodate advantageous use of this embodiment.
Figure 12C:
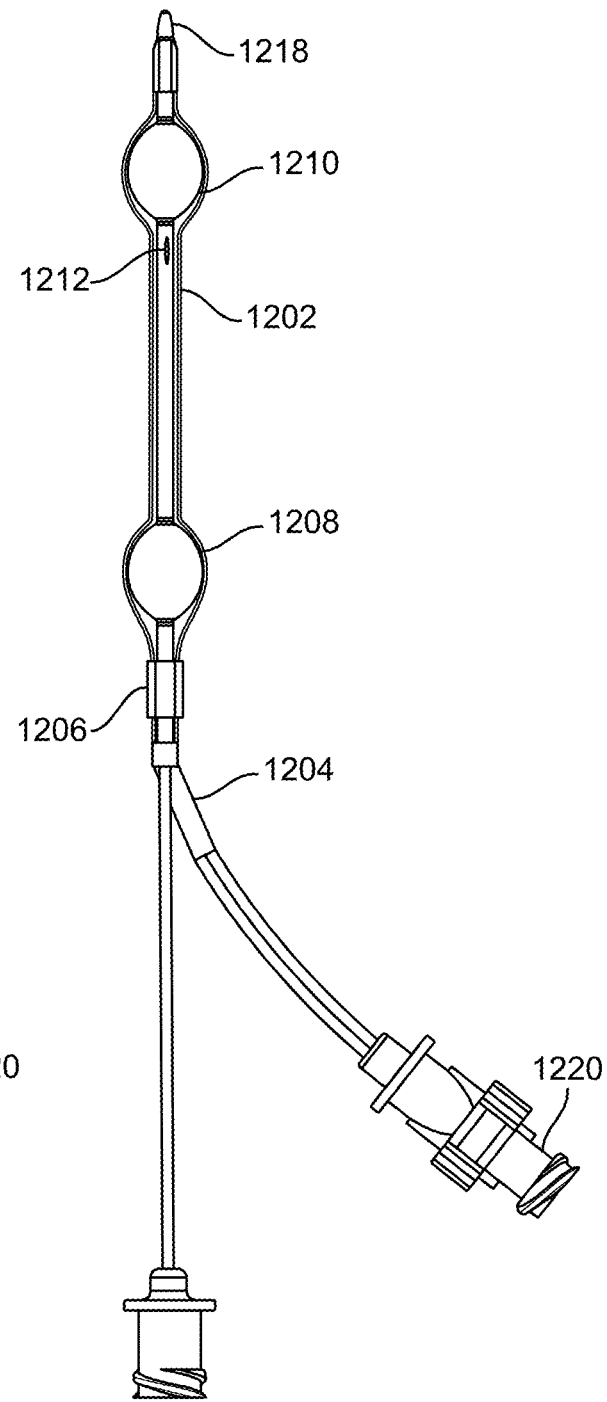

FIGS. 12A and 12C show an exemplary two balloon treatment device 1200 having mechanical abrasion elements 1202. The device 1200 comprises a catheter shaft 1204. An adapter or collar 1206 is positioned around the catheter shaft 1204. The collar 1206 comprises sockets 1207 for receiving mechanical abrasion elements 1202 (e.g., wires). The socket may be of the moveable or the fixed configuration type. The device comprises a first or proximal balloon 1208. The catheter shaft comprises an aspiration and injection port 1212, which can be in communication with an aspiration and injection lumen extending through the catheter shaft 1204. The device further comprises a second or distal balloon 1210. The mechanical abrasion elements 1202 extend along the catheter shaft and balloons, such that inflation of the balloons causes the mechanical abrasion elements to move radially outwardly from the catheter shaft. The mechanical abrasion elements 1202 are received by an adapter 1214 comprising sockets 1216 at a distal region of the device, proximal to the atraumatic distal tip 1218. A distal end of the sockets 1216 can taper towards the distal tip to minimize vessel wall trauma caused by the sockets. An atraumatic distal tip Use of a two-balloon treatment device is detailed in method 2000 in FIG. 20.

Figure 20:
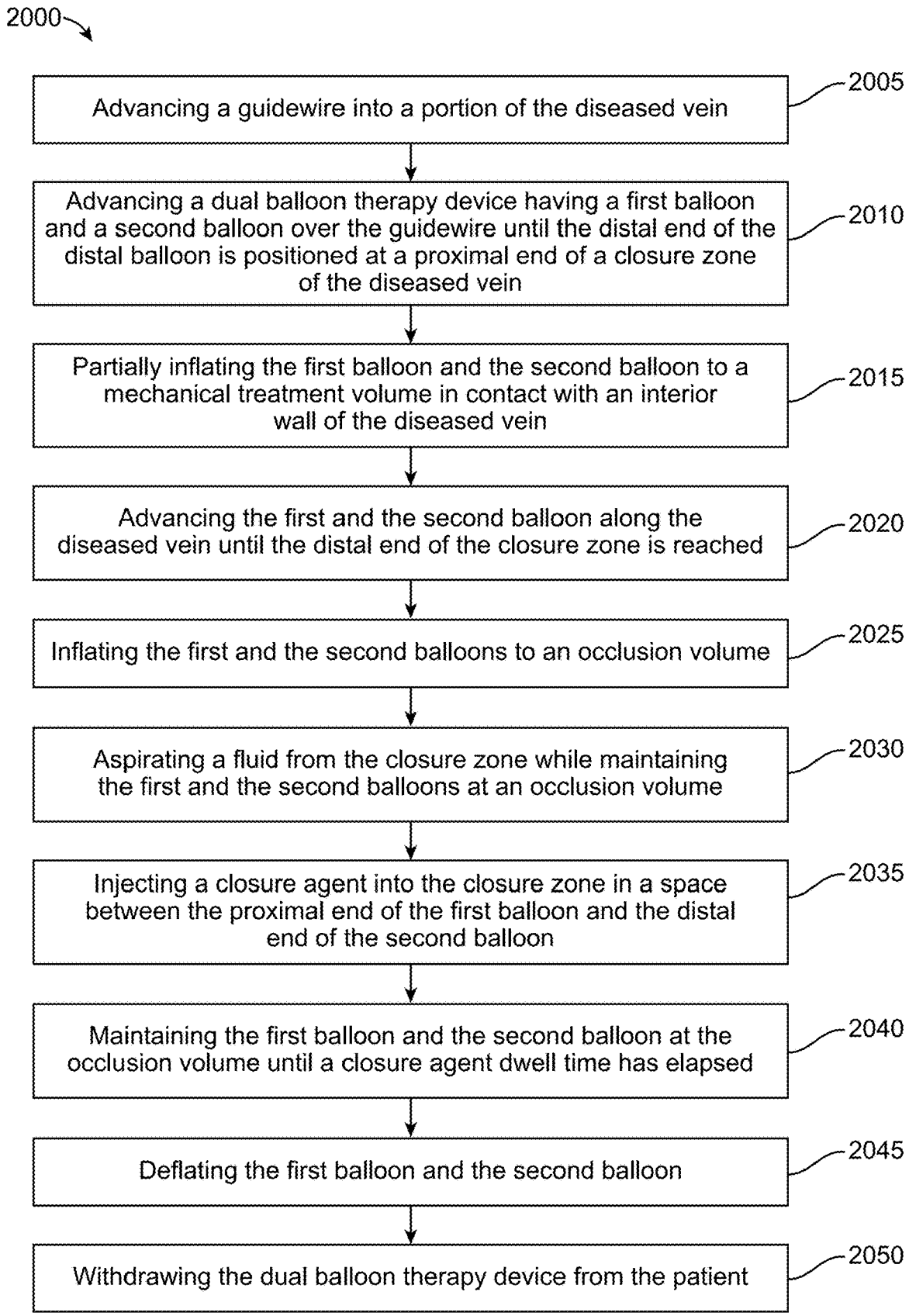
FIG. 20 is a flow chart of an exemplary two balloon therapy treatment method 2000 carried out in steps 2005-2050.

FIG. 12B is another exemplary two balloon treatment device 1200. In contrast to the embodiment of FIG. 12A, the mechanical abrasion elements 1202 extend only over the distal balloon 1210 and connect to a collar 1206 positioned between the proximal balloon 1208 and the distal balloon 1210. The abrasion elements may be of the sliding collar or fixed collar variations or any of the other variants described herein. In still additional aspects, there is provided another inflation port for the proximal balloon in addition to the inflation port 1220 for the distal balloon. As a result, the proximal balloon may be inflated separately from the distal balloon. Variations to the method 2000 in FIG. 20 are possible as a result of embodiments having independent operation of the distal and proximal balloons from stowed, deflated, partially inflated, and fully inflated conditions.

Figure 21A:
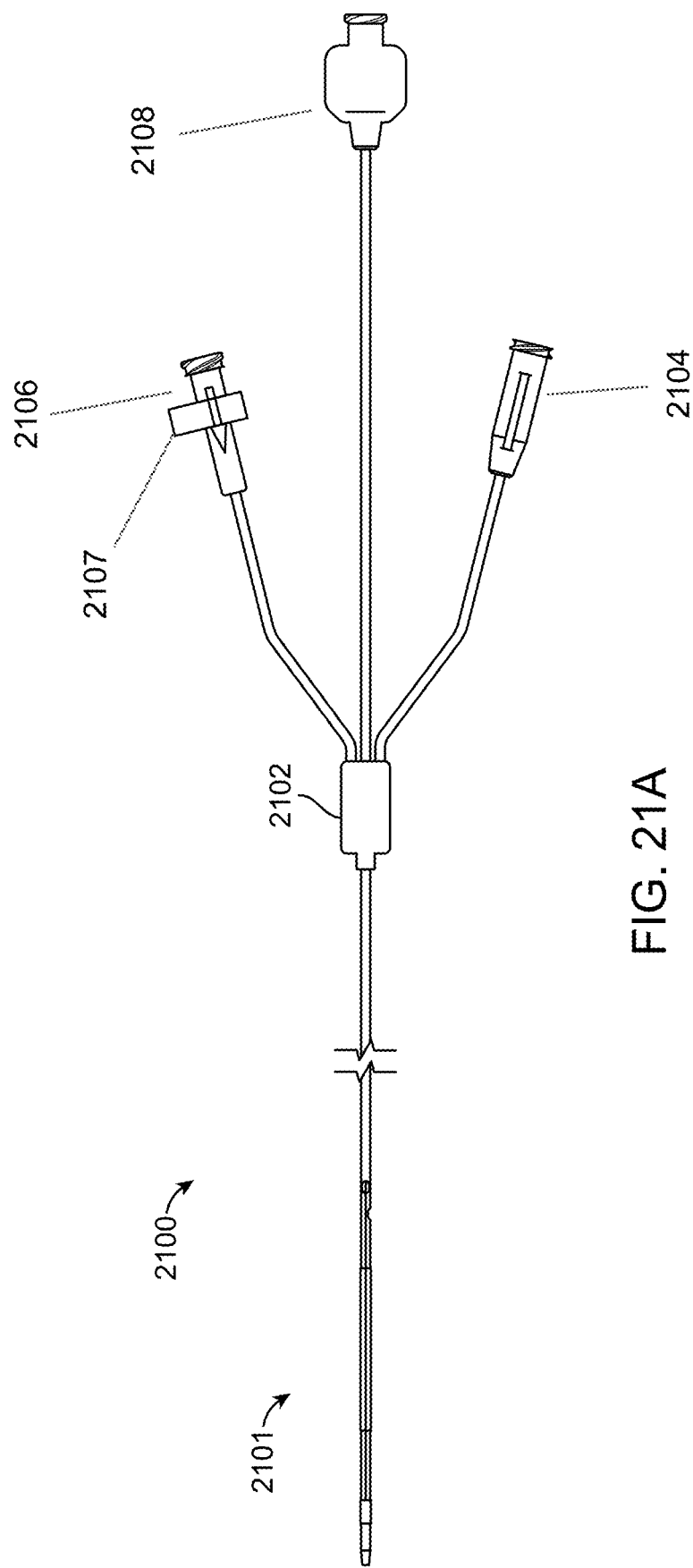
FIGS. 21A-21K illustrate various views of another embodiment of a balloon therapy device 2100.

Referring now to FIGS. 21A-21L, another embodiment of a balloon treatment device 2100 is shown. Unless otherwise described, the device comprises features similar to those described and illustrated with respect to other embodiments herein. FIG. 21A shows a top view of the overall device 2100, showing both the hub 2102 positioned at a proximal end of the device and the distal portion 2101 of the device.

Figure 21B:
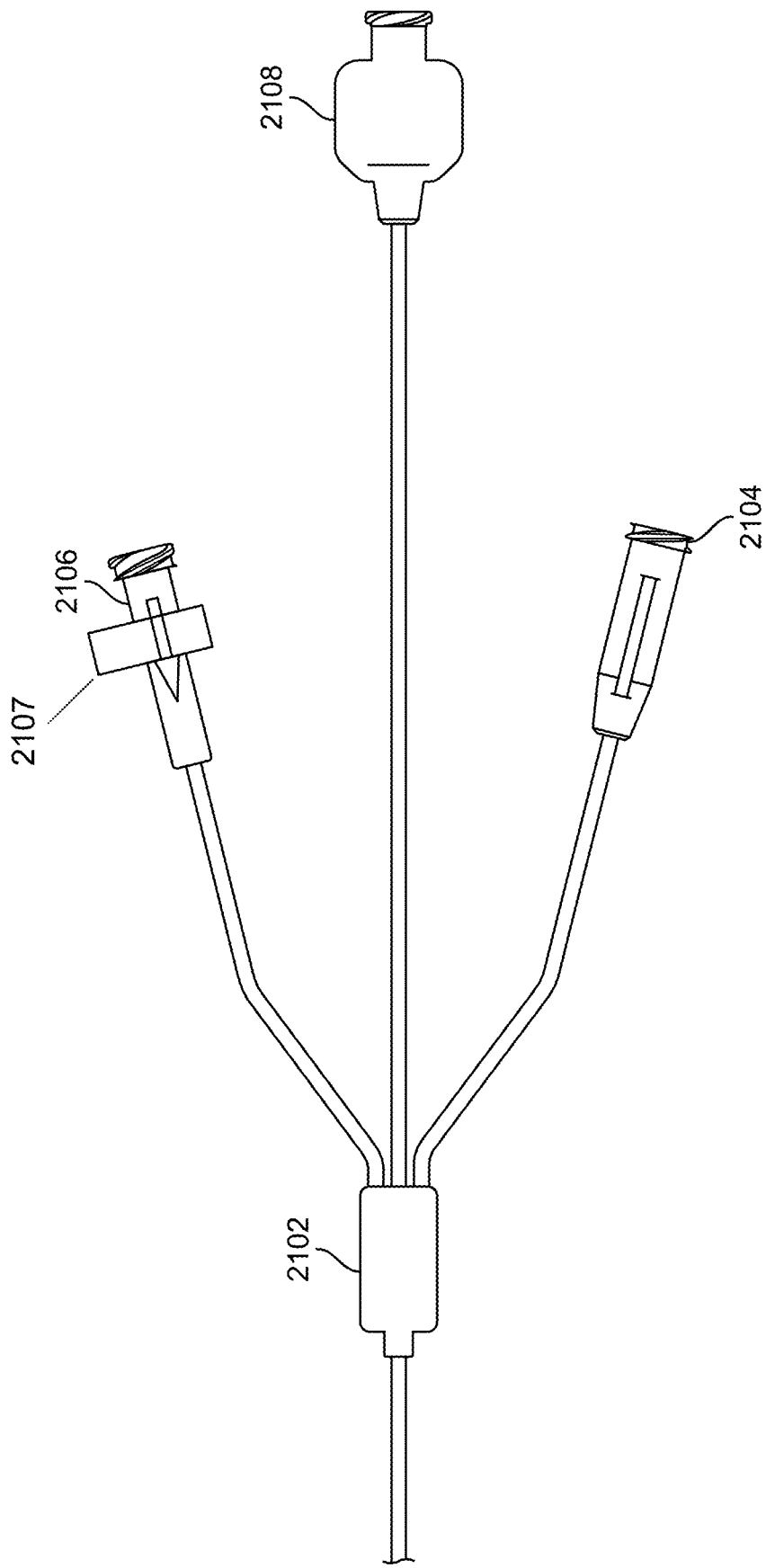
Figure 21C:
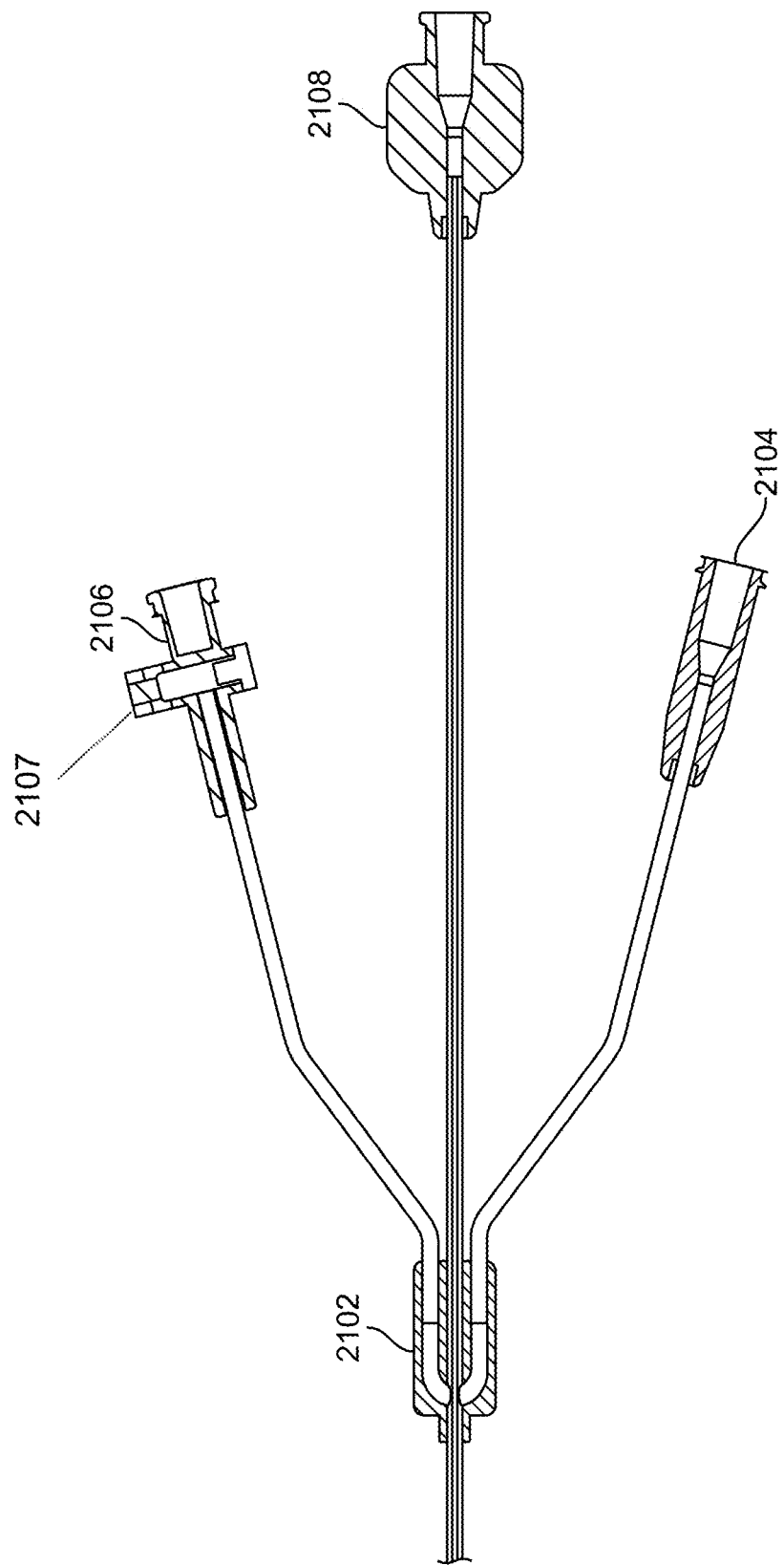

Moving to FIGS. 21B and 21C, an enlarged top and section view of the hub 2102 are shown. The hub 2102 couples a fluid port 2104, an inflation port 2106, and an access port 2108 for a catheter lumen (e.g., central lumen) to the corresponding lumens within the catheter. The inflation port 2106 can comprise a locking valve 2107. In some embodiments, the catheter lumen is sized to accommodate a guidewire.

Figure 21D:
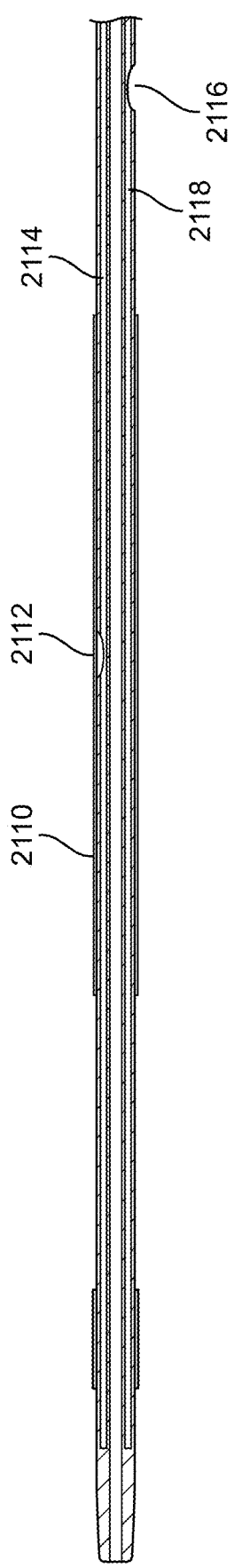

Moving to FIG. 21D, a section view of the distal portion 2101 of the device is shown with the balloon 2110 in an unexpanded configuration. The balloon inflation hole 2112 is shown in fluid communication with the balloon 2110 and the inflation lumen 2114. The inflation lumen is also in fluid communication with the inflation port (not shown). The inflation lumen 2114 is shown as extending past the balloon inflation hole 2112 in FIG. 21D. In some embodiments, the inflation lumen does not extend past the balloon inflation hole.

Also shown is the fluid aperture 2116. The fluid aperture can be used for aspiration and injection. The fluid aperture 2116 is in fluid communication with the fluid lumen 2118. The fluid lumen 2118 is also in fluid communication with the fluid port (not shown). The fluid lumen is shown extending past the fluid aperture 2116. In some embodiments, the fluid lumen 2118 does not extend past the fluid aperture 2116.

Figure 21E:
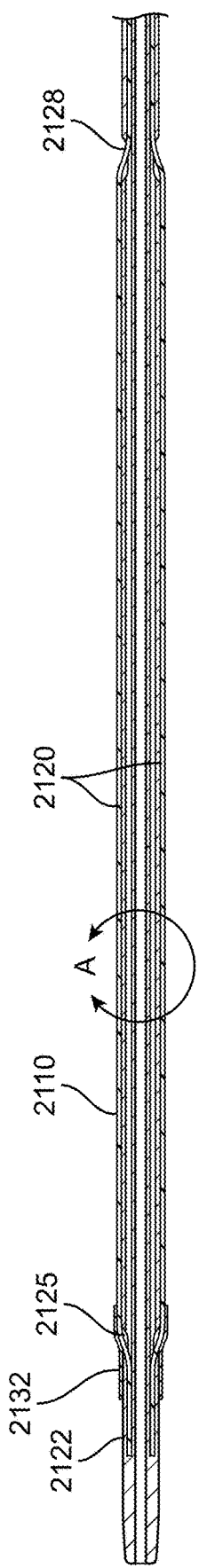

Referring now to FIG. 21E, a section view of the distal portion of the device with mechanical abrasion elements 2120 is shown. The apertures are not shown in this view. The device comprises the catheter shaft 2122. The mechanical abrasion element lumens 2134 and catheter lumen 2124 are shown within the catheter shaft 2122.

The mechanical abrasion elements 2120 are shown extending along a length of the catheter shaft 2122. The mechanical abrasion elements 2120 can be generally equally spaced around the circumference of the catheter shaft.

In one aspect, the mechanical abrasion structure includes two mechanical abrasion elements as shown. However, alternative embodiments of the mechanical abrasion structure may include a different number of mechanical abrasion elements. For example, 1, 3, 4, 5, or more mechanical abrasion elements can be utilized. In one aspect, the multiple mechanical abrasion elements are provided so as to be evenly spaced about the circumference of the balloon or may be positioned in selected portions about the circumference without regard to spacing.

The mechanical abrasion elements 2120 enter the catheter shaft through apertures 2125 on the shaft, near the distal end of the shaft. Inside the catheter shaft, the mechanical abrasion elements extend distally, ending a distance away from the distal end of the shaft. The mechanical abrasion elements can be fixed to the catheter shaft near the distal end by and/or near where they enter the catheter shaft by, for example, a fixed collar. In some embodiments, the fixed collar can comprise heat shrink. The mechanical abrasion elements may also be retained within the catheter by having a length of a dedicated lumen so that the maximum extension of the end of the element based on balloon inflation will remain within the lumen. Other configurations are also possible depending upon the specific characteristics of the balloon treatment device.

Proximal to the balloon, the mechanical abrasion elements enter the catheter shaft through apertures 2128 into dedicated lumens.

Figure 21F:
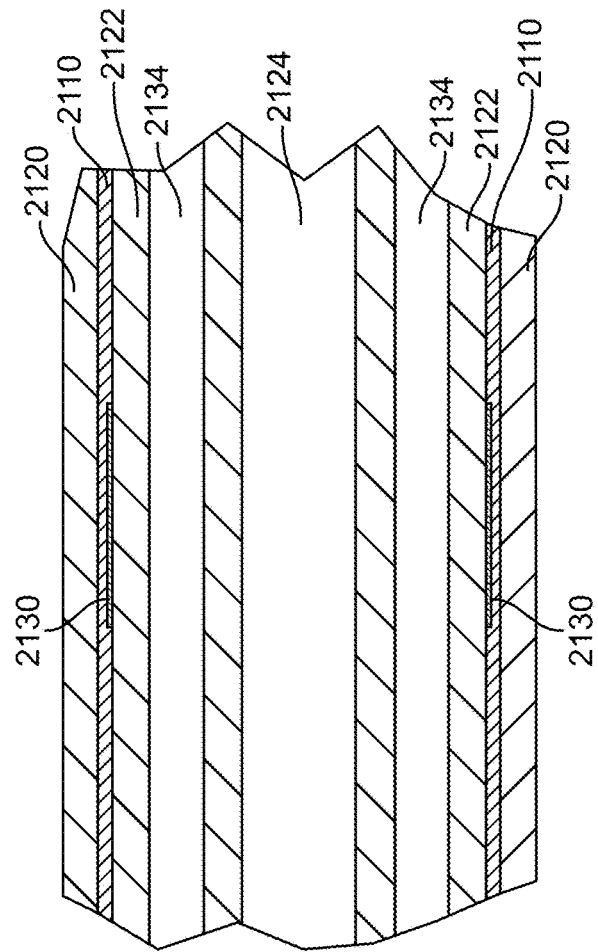

Moving now to FIG. 21F, a detailed section view of area A from FIG. 21E is shown. In FIG. 21E, the mechanical abrasion element lumens 2134, and catheter lumen 2124 are shown within the catheter shaft 2122. The balloon 2110 is shown positioned around the catheter shaft 2122. The mechanical abrasion elements are not shown in this figure.

Radiopaque marker elements 2130 are shown on the catheter shaft 2122. The radiopaque marker elements can be positioned at or near the proximal and distal ends of the balloon. Other configurations are also possible (e.g., a predetermined distance from the distal and proximal ends of the balloon). These marker elements can help to confirm positioning of the balloon during a procedure using the balloon therapy device. Suitable material for the marker is detectable under x-ray, fluoroscopy and the like, and includes, but is not limited to, platinum, gold, tantalum, zirconium and other materials having radiopaque properties.

Figure 21G:
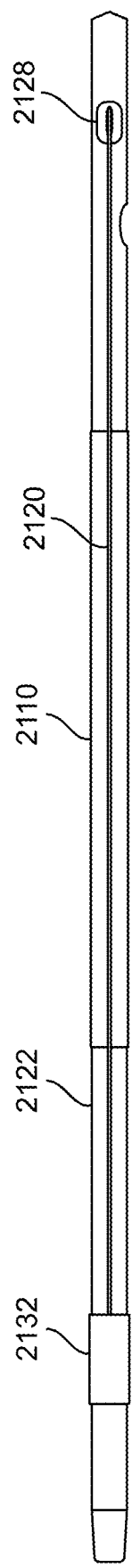
Figure 21H:
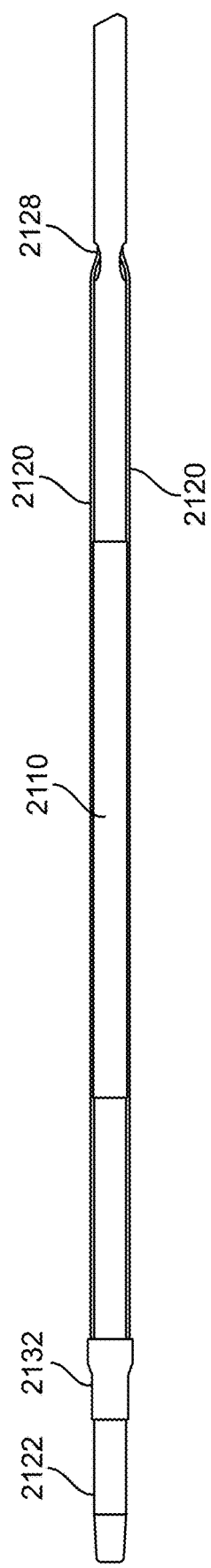

Referring now to FIGS. 21G and 21H, a side and a top view, respectively, of the balloon therapy device 2100 are shown. FIGS. 21G and 21H show the catheter shaft 2122, balloon 2110, and a mechanical abrasion element 2120, and aperture 2128. FIG. 21G also shows collar 2132 positioned at a distal portion of the catheter shaft 2122. The collar 2132 can fix a distal portion or end of the mechanical abrasion elements to the catheter shaft 2122.

In some embodiments, the collar comprises a polymer (e.g., PTFE). Other biocompatible fluoropolymers and plastics may be used.

The collar can be heat shrunk to fix to catheter shaft 2122 and mechanical abrasion elements 2120. Other configurations are also possible.

Figure 21I:
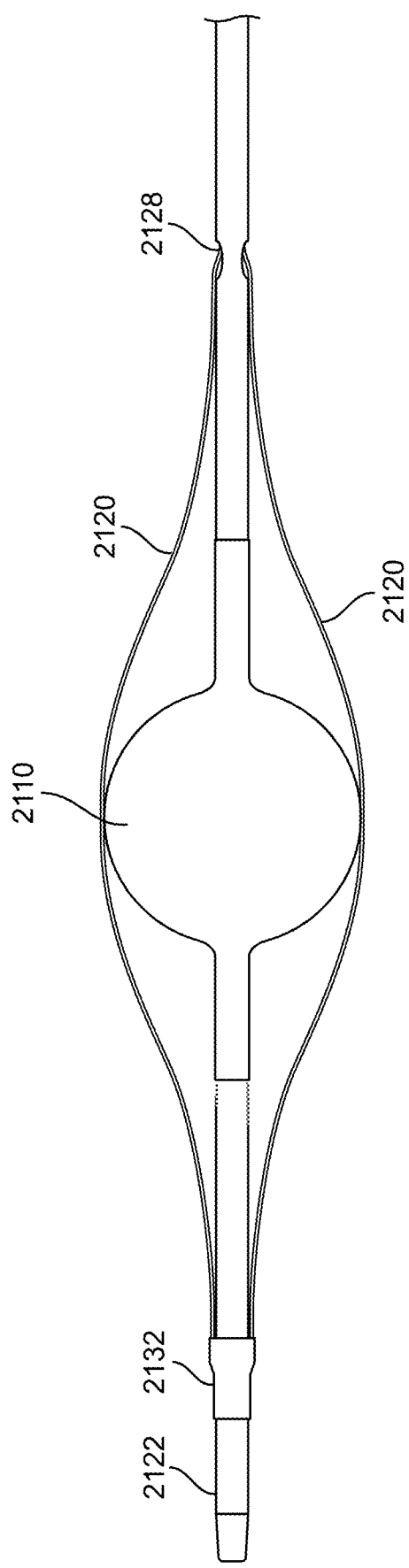
Figure 21J:
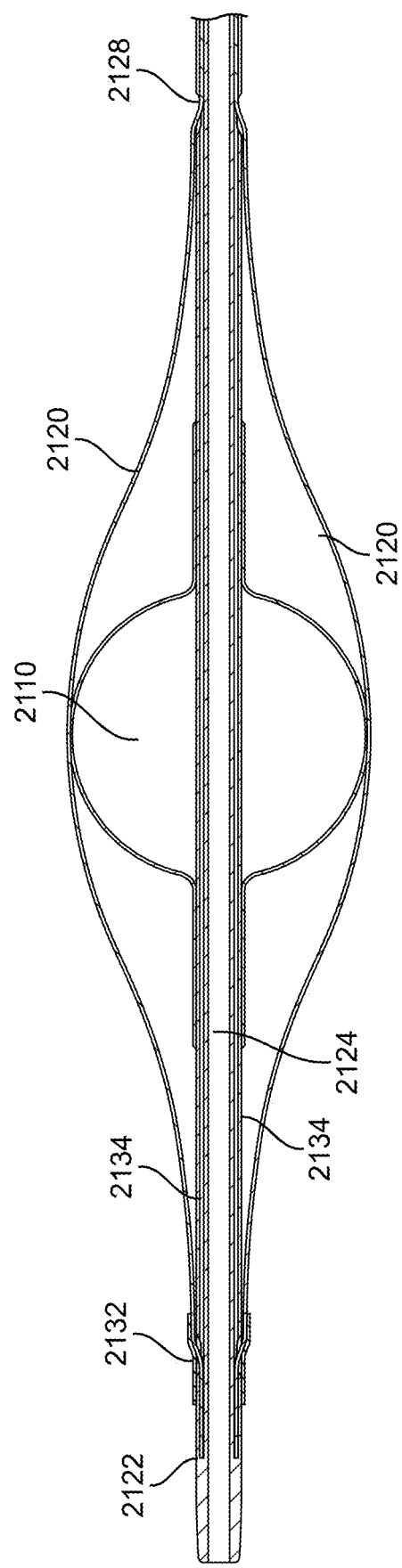

FIGS. 21I and 21J show a top view and a top section view, respectively, of the balloon therapy device 2100, when the balloon 2110 is in an expanded configuration. Shown in FIG. 21I are the catheter shaft 2122, balloon 2110, and a mechanical abrasion element 2120, and aperture 2128.

FIG. 21J also shows the catheter shaft 2122, balloon 2110, and a mechanical abrasion element 2120, and aperture 2128. Additionally, FIG. 21J shows the mechanical abrasion element lumens 2134 and catheter lumen 2124 within the catheter shaft 2122.

As the balloon 2110 expands, the portion of the mechanical abrasion elements 2120 positioned around the balloon 2110 moves or extends with the surface of the balloon, away from the catheter shaft 2122. The balloon increases in surface area as it expands. To accommodate the expanding surface area of the balloon, a portion of the mechanical abrasion elements 2120 positioned within the catheter shaft 2122, proximal to the balloon 2110, slides distally with respect to the catheter shaft, increasing the length of the mechanical abrasion element 2120 positioned outside of the catheter shaft.

When the balloon 2110 contracts, reducing its surface area, the portion of the mechanical abrasion element that moved from within the catheter shaft to outside the catheter shaft slides back into the catheter shaft through the aperture 2128. The portion of the mechanical abrasion element that moved or extended away from the catheter shaft along with the surface of the balloon, moves back towards the catheter shaft along with the surface of the balloon.

In some embodiments, the mechanical abrasion elements comprise mechanical properties allowing them to return back into the catheter shaft through aperture 2128 upon deflation of the balloon. For example, shape memory materials, such as nitinol, can allow the mechanical abrasion elements to return upon deflation of the balloon. In an additional aspect, some mechanical abrasion elements may be formed from shape memory materials having shape set properties to return into the elongate straightened condition as when the balloon is deflated or stowed.

Because the mechanical abrasion elements are fixed at the distal ends, expansion of the balloon causes the movable end, the proximal end of the mechanical abrasion element, to slide distally towards the balloon. In other embodiments, mechanical abrasion elements may be fixed relative to the proximal end and slide relative to the distal end.

Figure 21K:
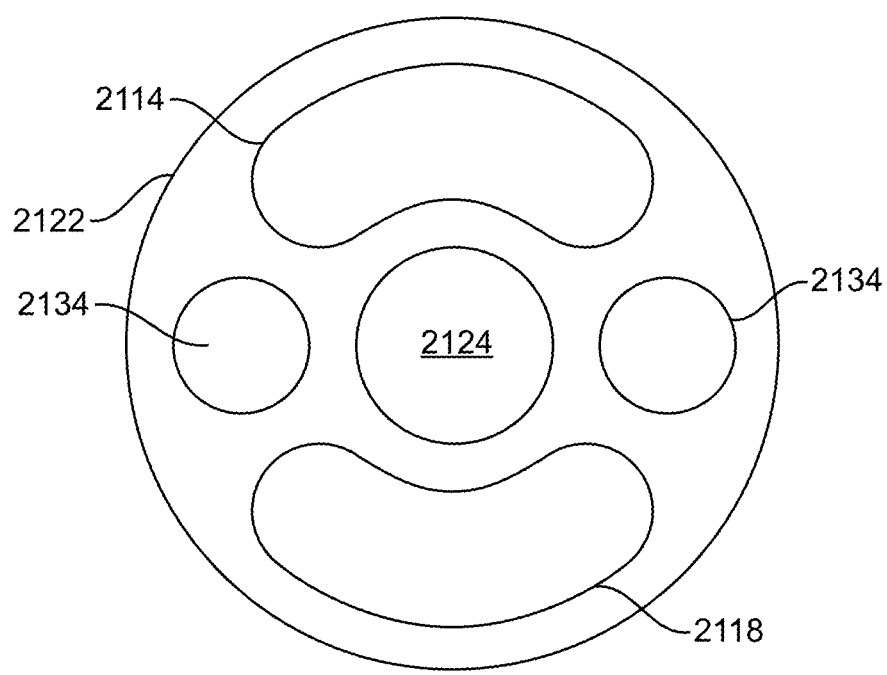

Referring now to FIG. 21K, a cross section of the catheter shaft 2122 is shown. In this view, a cross section of the inflation lumen 114, fluid lumen 118, mechanical abrasion element lumens 2134, and catheter lumen 2124 are shown.

The inflation lumen 114 and the fluid lumen 118 are shown as having partially annular cross sections. It will be appreciated that other configurations are also contemplated (e.g., rounded, ovular, rectangular, etc.).

In some embodiments, the fluid lumen and the inflation lumen have a same cross-sectional shape. In some embodiments, the fluid lumen and the inflation lumen have different cross-sectional shapes.

In some embodiments, the inflation lumen comprises a cross-sectional area of about 0.1-0.32 mm$^2$ (or about 0.12-0.30 mm$^2$, or about 0.15-0.28 mm$^2$, or about 0.20-0.24 mm$^2$, or about 0.22 mm$^2$, etc.).

In some embodiments, the fluid lumen comprises a cross-sectional area of about 0.1-0.32 mm$^2$ (or about 0.12-0.30 mm$^2$, or about 0.15-0.28 mm$^2$, or about 0.20-0.24 mm$^2$, or about 0.22 mm$^2$, etc.).

The catheter lumen 2124 is shown as having a circular cross-sectional shape, but other shapes are also contemplated.

The mechanical abrasion element lumens are shown as having circular cross sections, but other configurations are also contemplated (e.g., as described with respect to FIGS. 10I-L). For example, the mechanical abrasion element can have a rectangular or slit shaped cross section. In some embodiments, the cross-sectional shape of the lumen can be sized and selected based on the cross-sectional shape of the mechanical abrasion element. For example, lumens comprising a slit or rectangular cross section can be used with flat or ribbon shaped mechanical abrasion elements. Optionally, mechanical abrasion elements may have ends of a cross-sectional shape for sliding within the lumen and a second cross-sectional shape for engaging with the vessel wall. In one aspect, a mechanical abrasion element may have round cross-sections at the ends with a different cross-sectional shape for tissue engagement in a mid-portion. Still further, in an area where the mechanical abrasion element is bonded to the catheter, the element may have a flattened cross-section with a curvature to match the curvature of the shaft. The cross-section may then transition to a tissue engagement cross-section and finally to a lumen shaped cross-section.

In some embodiments, the catheter lumen 2124 is sized to allow passage of guide wires sized at 0.014", 0.018", and 0.035". The catheter lumen can comprise a diameter of amount 0.2-0.8 mm, or about 0.25-0.75 mm, or about 0.3-0.8 mm, or about 0.4-0.6 mm or about mm, etc.

In some embodiments, the mechanical abrasion element lumens comprise a diameter of about 0.1-0.3 mm or about 0.2 mm, etc.

In some embodiments, the end of the mechanical abrasion element that is configured to translate axially comprises a lubricious coating to reduce friction and ensure that the mechanical abrasion element can move readily. In some embodiments, the mechanical abrasion element lumen comprises a lubricious coating. In some embodiments, both the mechanical abrasion element lumen and the mechanical abrasion element end comprise a lubricious coating.

In some embodiments, the mechanical abrasion element comprises a wire. The wire can comprise a round cross section. Other configurations (e.g., flat wire) are also contemplated.

In some embodiments, the mechanical abrasion element comprises a diameter of about 0.1-0.6 mm (or about 0.05-0.015, 0.1-0.2, 0.15-0.25, 0.3-0.4, 0.35-0.45, 0.5-0.6, mm, etc.).

In some embodiments, the mechanical abrasion element aperture is large enough to allow the mechanical abrasion element to easily slide in and out of the aperture. For example, the mechanical abrasion element aperture can comprise a diameter about 0.1-0.5 mm greater than the mechanical abrasion element (or about 0.1-0.4, or about 0.1-0.3 or about 0.1.-0.2, or about 0.2-etc.).

In some embodiments, the mechanical abrasion element aperture can be perpendicular to a longitudinal axis of the catheter shaft. In some embodiments, the mechanical abrasion element aperture can be angled relative to the catheter shaft, to aid in egress and ingress of the mechanical abrasion element.

The mechanical abrasion apertures can be spaced about 5-30 mm (or about 10-30, about 10-20, about 10, about 15, about 20 mm, etc.) from the balloon on the proximal side of the balloon and the distal side of the balloon. In some embodiments, the proximal mechanical abrasion aperture is spaced the same distance from the balloon as the distal mechanical abrasion aperture.

The mechanical abrasion element can comprise a length of about 100-200 mm (or about 110-190 mm, or about 120-170 mm, or about 130-160 mm, or about 135-165 mm, or about 140-160 mm, or about 150 mm, etc.).

The mechanical abrasion element can comprise nitinol. Other materials are also contemplated (e.g., stainless steel). In some embodiments, the nitinol mechanical abrasion element may be shape-set to employ a shape memory transitional range at or near body temperature or at temperature within the blood flow of the patient (i.e., 37 C or 98.6 F). In one embodiment, the nitinol elements are shape-set to a position alongside the balloon when the balloon is in the deflated or stowed state. In this way, initial inflation of the balloon with first overcome the nitinol shape set force, which can be adjusted using any conventional shape set technique. As such, after completion of the occlusion step after the delivery of the closure agen the nitinol elements will provide a return force as the move back to the body temperature shape set state. Additionally or optionally, this same technique could be employed to have the amount of nitinol shape set return force to be sufficient to not only aid in balloon deflation but also to provide return force sufficient to drive the ends of the mechanical abrasion elements along their dedicated catheter lumen, in those embodiments having mechanical abrasion elements with one or both translating ends. It is to be appreciated that alternative shape setting forms may be employed to adapt additional characteristics, level of engagement or position of engagement or performance of all or part of the length of a nitinol mechanical abrasion element. Still further, the shape setting technique may be applied to all or a portion of the mechanical abrasion element in either continuous or discontinuous segments so as to further adapt the performance of the nitinol shape transition to enhance the performance of the balloon treatment device.

In some embodiments, the catheter is a 4 F catheter. Other sizes (e.g., 5 F, 6 F, 7 F, etc.) are also possible.

In some embodiments, the catheter comprises a length of about 60-120 cm.

The catheter can comprise polyurethane, PEBAX, polyethylene, nylon, polycarbonate, other thermoplastics, etc.

In some embodiments, the balloon comprises a compliant material. The balloon can comprise latex, TPE, polyurethane, other thermoplastics, etc.

It will be appreciated that the description of the device components provided above can apply to all embodiments described herein, unless described otherwise. Any embodiment described herein can comprise any combination of features (e.g., dimensions, materials, etc.). described above.

Figure 23A:
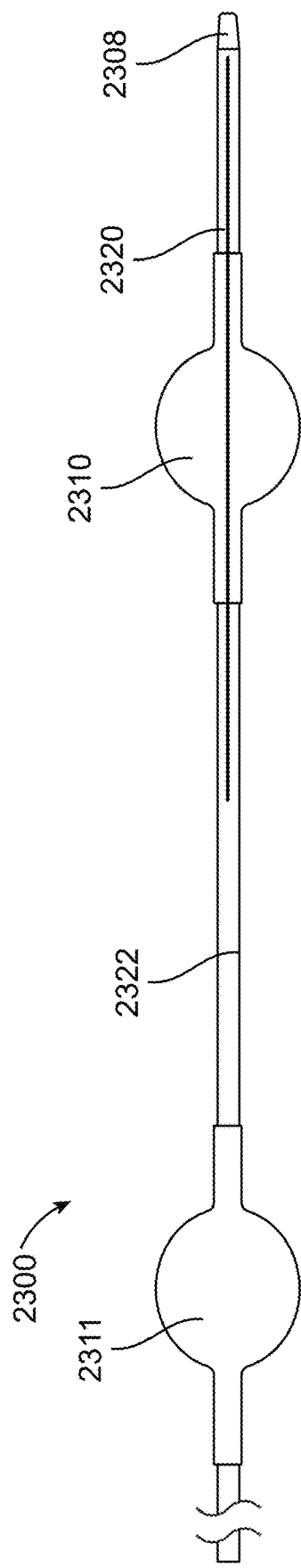
FIGS. 23A-D show various views of an embodiment of a two-balloon therapy device.
Figure 23B:
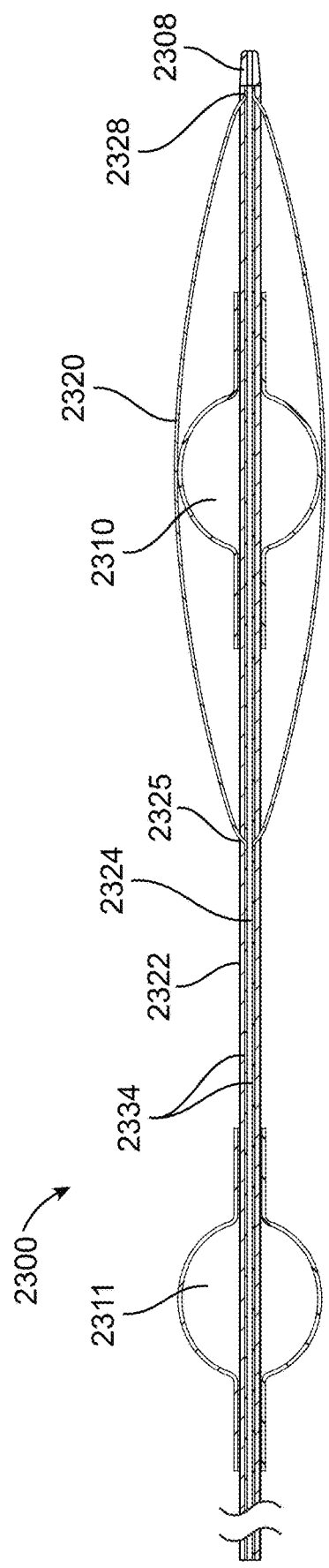
Figure 23C:
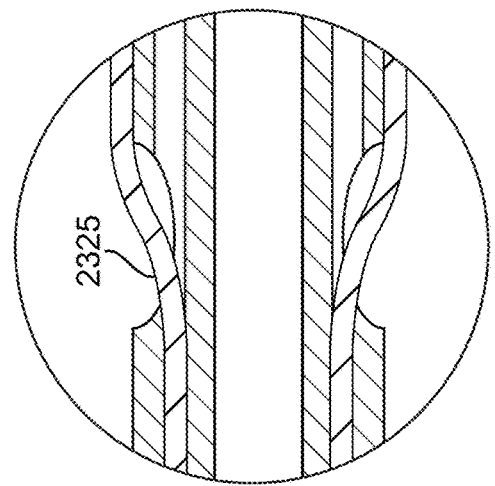

FIGS. 23A-23C show a side view, a top section view and a side section view, respectively, of an embodiment of a balloon therapy device 2300 comprising a distal balloon 2310 and a proximal balloon 2311. The device 2300 comprises a catheter shaft 2322 around which the balloons 2310, 2311 are arranged. Unless described otherwise, the device 2300 can comprise features like those described with respect to other devices herein (e.g., device 2200, device 2100, etc.).

One or more mechanical abrasion elements 2306 extend along the catheter shaft 2322. Unless described otherwise, the mechanical abrasion elements 2306 are similar to mechanical abrasion elements described elsewhere herein (e.g., mechanical abrasion elements 2120).

Figure 26:
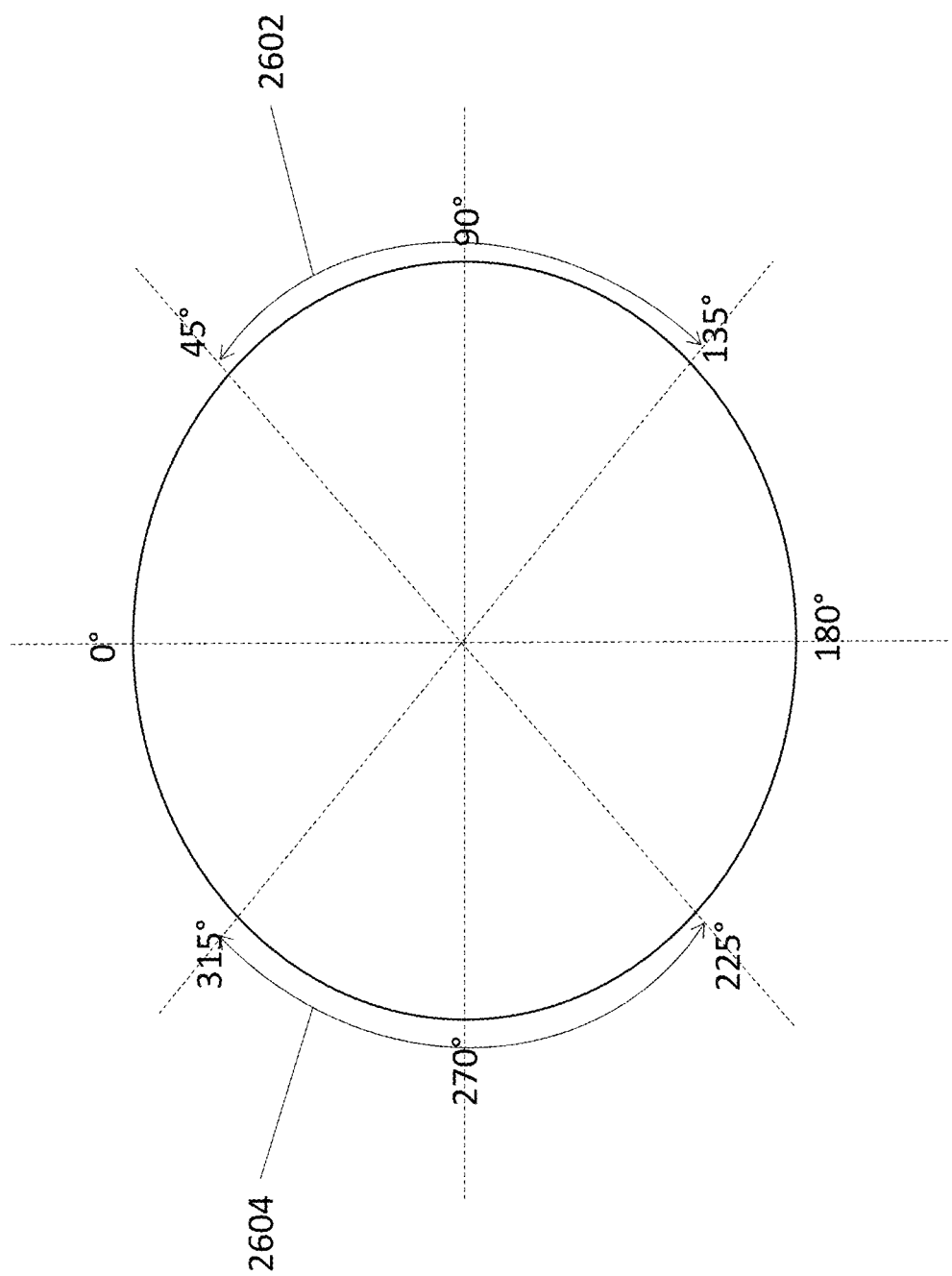
FIG. 26 shows a section view of possible relative circumferential positions of a first and second mechanical abrasion element around a catheter shaft.

The mechanical abrasion elements 2320 can be generally equally spaced around the circumference of the catheter shaft. For example, in a device with two mechanical abrasion elements, a first mechanical abrasion element can be positioned around the catheter shaft at a circumferential position of about 45-135° and a second mechanical abrasion element can be positioned around the catheter shaft at a circumferential position of about 225-315°. FIG. 26 shows a section view of catheter shaft showing a first portion 2602 of the circumference of the catheter shaft corresponding to a possible position for a first mechanical abrasion element and a second portion 2604 of the circumference of the catheter corresponding to a possible position for the second mechanical abrasion element. It will be appreciated that these portions may be rotated about the catheter shaft, as long as their relative positions to one another correspond to the first and second portions. Other positions for the mechanical abrasion elements are also contemplated.

Two mechanical abrasion elements are shown; however, a different number is also contemplated. For example, 1, 3, 4, 5, or more mechanical abrasion elements can be utilized.

The mechanical abrasion element lumens 2334 extending along catheter shaft are shown in FIG. 23B. The catheter lumen 2324 is also shown extending through the center of the catheter. Other configurations are also possible.

The mechanical abrasion elements 2320 enter the catheter shaft through apertures 2328 on the shaft, near the distal end of the shaft. Inside the catheter shaft, the mechanical abrasion elements extend distally, ending a distance away from the distal end of the shaft. The distance can be about 3-8 mm (or about 4-7 mm, 5-6 mm, 1-10 mm, about 5 mm, about 5.5 mm, about 6 mm, etc.). The mechanical abrasion elements can be fixed to the catheter shaft near the distal end by and/or near where they enter the catheter shaft (e.g., using a fixed collar). Other configurations are also possible. For example, the mechanical abrasion elements can be fixed to the catheter shaft using adhesive bonding. Other methods of bonding (e.g., thermal bonding, RF welding, ultrasonic bonding, etc.) are also contemplated.

From their distal end, the mechanical abrasion elements 2330 extend proximally over the distal balloon 2310 and enter the catheter shaft through apertures 2325. Through the apertures, the mechanical abrasion elements 2330 enter mechanical abrasion element lumens extending within the catheter shaft. The mechanical abrasion element lumens can be angled, as described in more detail with respect to FIG.

28A. As the balloon 2310 expands, the portion of the mechanical abrasion elements 2320 positioned around the balloon 2310 moves or extends with the surface of the balloon, away from the catheter shaft 2322. The balloon increases in surface area as it expands. To accommodate the expanding surface area of the balloon, a portion of the mechanical abrasion elements 2320 positioned within the catheter shaft 2322 slides distally with respect to the catheter shaft, increasing the length of the mechanical abrasion element 2120 positioned outside of the catheter shaft.

When the balloon 2310 contracts, reducing its surface area, the portion of the mechanical abrasion element that moved from within the catheter shaft to outside the catheter shaft slides back into the catheter shaft through the aperture. The portion of the mechanical abrasion element that moved or extended away from the catheter shaft along with the surface of the balloon, moves back towards the catheter shaft along with the surface of the balloon.

The proximal and distal balloons 2310, 2311 can comprise radiopaque marker elements (e.g., near their distal and proximal ends). Other configurations are also possible (e.g., a predetermined distance from the distal and proximal ends of the balloon). These marker elements can help to confirm positioning of the balloon during a procedure using the balloon therapy device. Suitable material for the marker is detectable under x-ray, fluoroscopy and the like, and includes, but is not limited to, platinum, gold, tantalum, zirconium and other materials having radiopaque properties.

FIG. 23C shows an enlarged view of the mechanical abrasion element 2320 entering mechanical abrasion element lumen 2334 through aperture 2325. In this embodiment, the mechanical abrasion element lumen 2334 is not angled, and instead the mechanical abrasion element aperture 2325 comprises a greater width.

Figure 23D:
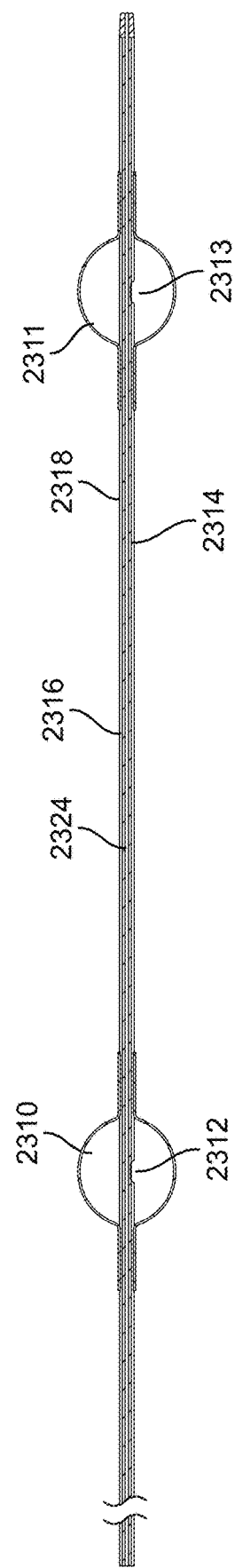

Moving to FIG. 23D, a side section view of the device 2300 is shown. This view shows the catheter lumen 2324. Also shown are the distal balloon inflation hole 2312 and the proximal balloon inflation hole 2313 in fluid communication with the inflation lumen 2314. In some embodiments comprising more than one balloon, one or more balloons can comprise separate inflation lumens. The inflation lumen 2313 is shown as extending past the balloon inflation hole 2312 in FIG. 23D. In some embodiments, the inflation lumen does not extend past the balloon inflation hole.

Additionally, FIG. 23D shows the fluid aperture 2316. The fluid aperture can be used for aspiration and injection. The fluid aperture 2316 is in fluid communication with the fluid lumen 2318. The fluid lumen 2318 is also in fluid communication with the fluid port (not shown). The fluid lumen is shown extending past the fluid aperture 2316. In some embodiments, the fluid lumen 2318 does not extend past the fluid aperture 2316.

The distance between the proximal and distal balloon can be about 10 to 30 cm (or about 1-40 cm, or about 5-40 cm, or about 5-30 cm, or about 5-35 cm, etc.). The spacing between the balloons is selected to correspond to a desired isolated treatment length.

While only one balloon, the distal balloon 2310, is shown comprising mechanical abrasion elements, in some embodiments, both balloons comprise mechanical abrasion elements arranged around them. In some embodiments, only the proximal balloon comprises mechanical abrasion elements arranged around it.

While the embodiments described herein show the distal end of the mechanical abrasion elements as being fixed and the proximal end being able to translate, it will be appreciated that, in some embodiments, the proximal end of the mechanical abrasion elements if fixed and the distal end is able to translate to accommodate expansion and contraction of the balloon.

The device 2300 comprises an atraumatic distal tip portion 2308. The distal tip can taper towards its end, providing a blunt, atraumatic leading end of the device 2300.

In some embodiments, the device comprises only a balloon, without mechanical abrasion elements. Advancing a balloon in contact with the vessel wall, with or without abrasive structures on the balloon, can induce endothelial injury leading to a healing response and/or venospasm. The healing response and/or venospasm may contract the vessel/reduce the volume of the vessel around the catheter shaft, reducing the volume to be aspirated.

In some embodiments, the balloon of a balloon-based therapy device is utilized in one of three states: deflated state, partially inflated mechanical treatment state and fully inflated state which is also used as a vessel occlusion state.

A balloon will be placed in the deflated state during storage, prior to insertion, during insertion until reaching a proximal end of a treatment zone and before removal from a treatment zone and the patient anatomy after delivery of the closure agent.

A balloon will be placed in a partially inflated or mechanical treatment state when the balloon is positioned at a proximal end of the treatment zone in order to cause sufficient contact between the balloon and an inner wall of the lumen undergoing treatment. The amount of partial inflation volume for sufficient contact to enable mechanical treatment will vary based on a number of factors such as the type of mechanical treatment device, balloon size, element or structure being used, the size and condition of the lumen and elasticity of the lumen and other clinical considerations. Additionally, there is also a balance between sufficient engagement between the balloon outer wall and mechanical abrasion element or elements and the lumen wall and the ability to advance the balloon along the treatment zone from the proximal end to the distal end. If the partial inflation volume is too low, then there will not be sufficient mechanical engagement and desired level of abrasion. If the partial inflation volume is too high, then the user will be unable to advance the balloon along the treatment zone, induce too much mechanical abrasion or not be able to advance the balloon along the lumen. In other words, the volume of the balloon in the partially inflated state is such that apposition between the lumen wall and the balloon/mechanical abrasion elements, device or structure is maintained while allowing the balloon to be readily advanced along the treatment zone. The volume of the balloon in the partially inflated state is greater than the deflated state and less than the fully inflated or occlusion state.

The partially inflated or mechanical abrasion volume is such as to provide sufficient apposition between a structure of the balloon treatment device and a wall of the vessel within the treatment zone sufficient to damage the vessel wall and evoke a healing response from the patient. As a result, the process of hemostasis along with vasoconstriction and platelet activation adhesion and activation begins along with release of clotting factors among other receptors and mediators including fibrin and the beginning of the clotting cascade. While desiring not to be bound by theory, it is believed that active aspiration (i.e., active intravascular removal of vessel fluids as opposed to passive drainage by elevating limbs or using massage or bandages) provides a more conducive environment for treatment using the methods described herein. Actively removing fluids from the treatment site and immediately injecting the treatment agent is believed to provide a superior environment for interaction between the vessel wall in the treatment zone and the closure agent. This superior environment is based, at least in part, on the more reliable and complete evacuation of blook from the treatment zone. Blood can deactivate a foam-based treatment agent (e.g., polidocanol). Thus, reliable and complete evacuation of blood can enable the complete effect of the delivered treatment agent. The amount of mechanical abrasion pressure (e.g., force of abrasion elements against the vein wall). will vary based on a number of factors such as vessel wall patency, surrounding tissues and structures and other clinical considerations. In one aspect, an indication of sufficient mechanical abrasion pressure is that a mechanical abrasion structure provided by the balloon therapy device will disrupt or injure the endothelium but not cause vessel perforation.

The third balloon state is the fully inflated or the occlusion state. The balloon is placed in the fully inflated state when the balloon reaches the distal end of the treatment zone. The occlusion volume or fully inflated state will vary depending upon the patient anatomy and the condition of the lumen as described above. The level of fully inflated pressure is also sufficient to maintain an isolation of the treatment zone from other parts of the lumen so that active aspiration and agent injection remain mostly in the treatment zone, proximal to the fully inflated balloon.

In some embodiments, the balloon comprises a compliant balloon. The compliance of a balloon device can be defined by the diameter increase that results from a predetermined increase in inflation pressure. Semi-compliant balloons respond to an increase in inflation pressure by initially increasing in diameter in areas that lie more proximally or distally to the area of the highest resistance, thus taking on a characteristic dumbbell shape during the gradual pressure increase. Non-compliant balloons expand uniformly over their longitudinal axis and generally cannot be expanded past a predetermined maximum diameter. The radial force exhibited by semi compliant and non-compliant balloons in, for example, a stenotic target area is higher than the one exhibited by compliant balloons, a finding reported within the context of percutaneous coronary interventions.

As the compliant balloon is inflated, it will expand to contact the vessel wall. As it continues to expand from the point of vessel wall contact, the compliant balloon can increase in volume while deforming to the shape of the vein, causing the balloon to acquire a longitudinal shape, the balloon contacting the vessel wall over a greater length of the balloon. The increased frictional force caused by the greater surface area of the balloon in contact with the vessel wall can make the balloon increasingly hard to slide within the vessel, and also enhance the balloon's occlusion of the vessel and stabilize the balloon's position within the vessel. The compliance of the balloon can help minimize the trauma to the vein wall.

The compliance of the balloons used in the devices described herein differentiates them from scoring or cutting balloons having wires surrounding the balloon (e.g., Philips Angiosculpt Evo) as such balloons comprise semi-compliant or noncompliant balloons designed to apply a higher force to stenotic lesions. The purpose of those devices is to impart a significant amount of force and change the shape of the surrounding anatomy. This purpose is very different from the minimal injury caused by the devices described herein.

The noncompliant or semi-compliant balloons used in scoring or cutting devices are configured to be inflated to pressures of 5-30 atm. These pressures are much higher than the pressures of the compliant balloons used with the devices described herein. Such compliant balloons may be inflated using volume to drive expansion of the balloon shape for the particular functionality such as abrasion element engagement along a closure zone or vessel occlusion prior to an aspiration step or during a closure agent dwell time. While desiring not to be bound by theory, it is believed that the inventive balloon therapy devices described herein operate within a pressure range of 1 atm or less.

The properties of noncompliant or semi-compliant balloons allow them to be inflated uniformly to apply a constant radial expansion force along their outer surface. If portions of the balloon were to exert pressure against, for example, a stenotic lesion, before other portions of the balloon, the compressing portion of the balloon may dislodge or shift portions of the stenotic lesion towards non-compressed portions of the vessel, increasing thrombosis risk. In contrast, the balloons of the devices described herein do not uniformly contact the vessel wall. Instead, the surface area undergoing vessel wall contact increases as the balloon volume increases.

Cutting and/or scoring devices also differ from the inventive balloon therapy device embodiments described herein by the way wire elements are attached to the device. The devices described herein have mechanical abrasion element lumens with apertures spaced away from the balloon. The lumens and apertures spaced away from the balloon allow the mechanical abrasion element to return to their original position within the lumen upon deflation of the balloon. In contrast, cutting and/or scoring balloon devices generally have the wires attached to the catheter shaft close to or immediately on either side of the balloon.

Referring now to FIG. 22, an embodiment of an inflated balloon of a balloon therapy device as described herein is shown. FIG. 22 shows the device shaft 2202. Arrow 2204 extends towards the proximal end. Arrow 2206 extends towards the distal end. The mechanical abrasion element 2208 is shown around the balloon 2210 and in contact with the vein wall 2212. As shown in FIG. 22, as the balloon is inflated, it expands radially and axially, eventually forming a generally cylindrical shape, with an oblong cross section. This shape can be a result of the compliant nature of the balloon. Once it expands to make contact with the venous wall, it conforms to the wall. increased inflation will not cause the balloon to expand the vessel, but will instead continue to expand the balloon in such a way that it continues to conform to the constraints of the vessel wall. In this way, increased inflation of the balloon increases the surface area of the balloon in contact with the vessel wall. This increased surface area of contact provides a greater frictional force holding the balloon in place along the vessel wall. The length of the balloon in engagement with the vessel wall is shown as $l_e$.

In some embodiments, mechanical abrasion elements extend along the device and over the balloon, as described herein. Mechanical abrasion elements extending over the balloon can provide several advantages. A first is that the mechanical abrasion elements can improve trackability of a balloon therapy device. A compliant balloon catheter can exhibit jerky motion as a partially inflated balloon is advanced through the vasculature making vessel wall contact. The catheter often fails to advance smoothly and continuously and requires additional operator force to advance and does so in a jerky or stepwise manner. The mechanical abrasion elements extending along the catheter shaft reinforce the catheter, improving its column strength. This increased strength makes the device more trackable when being advanced with a partially inflated balloon and while making vessel wall contact. Improved trackability allows for the catheter to advance smoothly and continuously. The catheter has enclosed mechanical abrasion elements which are exposed over the balloon mounted portion of the catheter. These mechanical abrasion elements running along the shaft of the catheter reinforce the catheter, (increase the catheter's column strength) making it more trackable when being advanced with the balloon partially inflated and in contact with the vessel wall. This makes for a more predictable and smooth operator experience and a more uniform mechanical impact on the inner lining of the vessel wall.

The mechanical abrasion elements also increase the visibility of the device under, for example, ultrasound visualization, making it simpler for the operator to identify contact with the vessel wall when the balloon is partially inflated. Better visualization helps to ensure adequate wall contact and make the device easier to use.

The mechanical abrasion elements also provide consistent endothelial interaction to ensure sufficient ablative contact, regardless of balloon inflation volume. This consistent endothelial interaction creates a consistent degree of mechanical injury, ensuing a more consistent and desired outcome.

Figure 13:
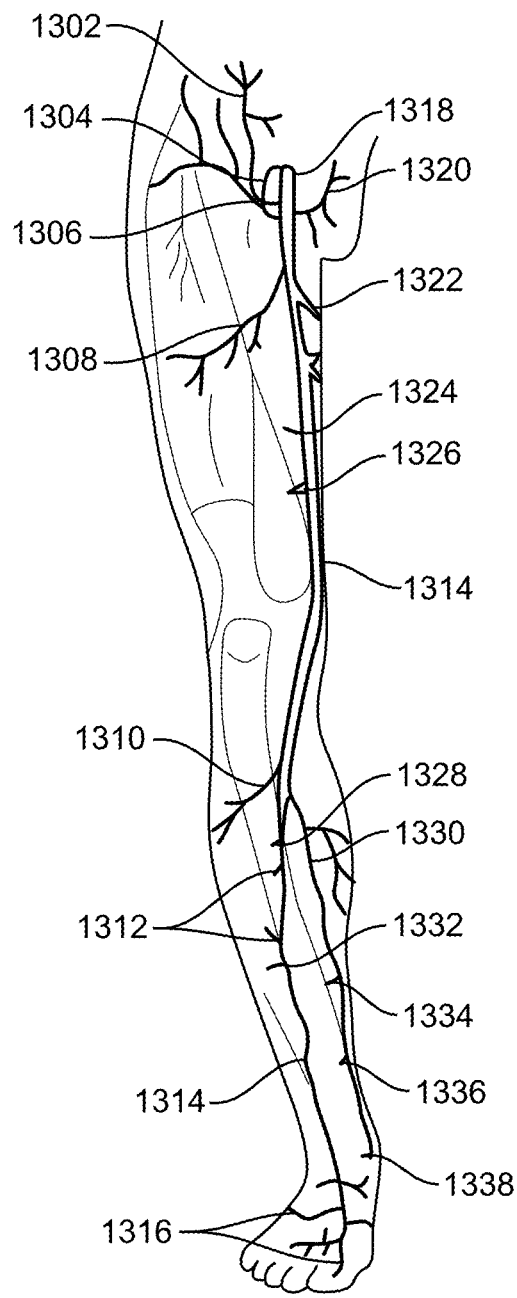
FIGS. 13 and 14 illustrate exemplary venous vasculature in the lower limbs and pelvis that may be targeted for treatment using the devices and methods described herein.
Figure 14:
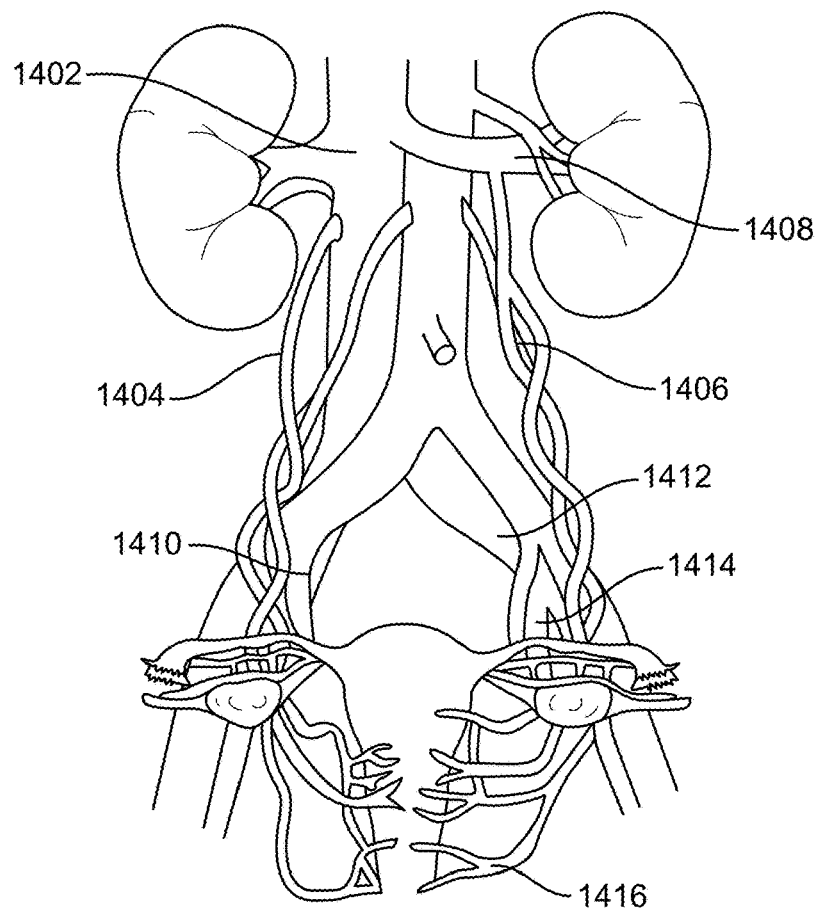

FIGS. 13 and 14 illustrate exemplary venous vasculature in the lower limbs and pelvis that may be targeted for treatment using the devices and methods described herein. FIG. 13 shows the superficial epigastric vein 1302, the common femoral artery 1304, the superior circumflex iliac vein 1306, the lateral accessory saphenous vein 1308, the anterior tributary of the greater saphenous vein 1310, the proximal paratibial perforators 1312, the greater saphenous vein 1314, the medial perforators of the foot 1316, the common femoral vein 1318, the superficial external pudendal vein 1320, the medial accessory saphenous vein 1322, the Hunter's perforator 1324, the Dodd's perforator 1326, the Boyd's perforator 1328, the posterior arch vein 1330, the 24 cm perforator 1332, the Cockett III perforator 1334, the Cockett II perforator 1336, and the Cockett I perforator 1338.

FIG. 14 shows the inferior vena cava 1402, the right ovarian vein 1404, the left ovarian vein 1406, the left renal vein 1408, the right common iliac 1410, the left common iliac 1412, the internal iliac vein 1414, and the uterine venous plexus 1416.

Figures 15A, 15B:
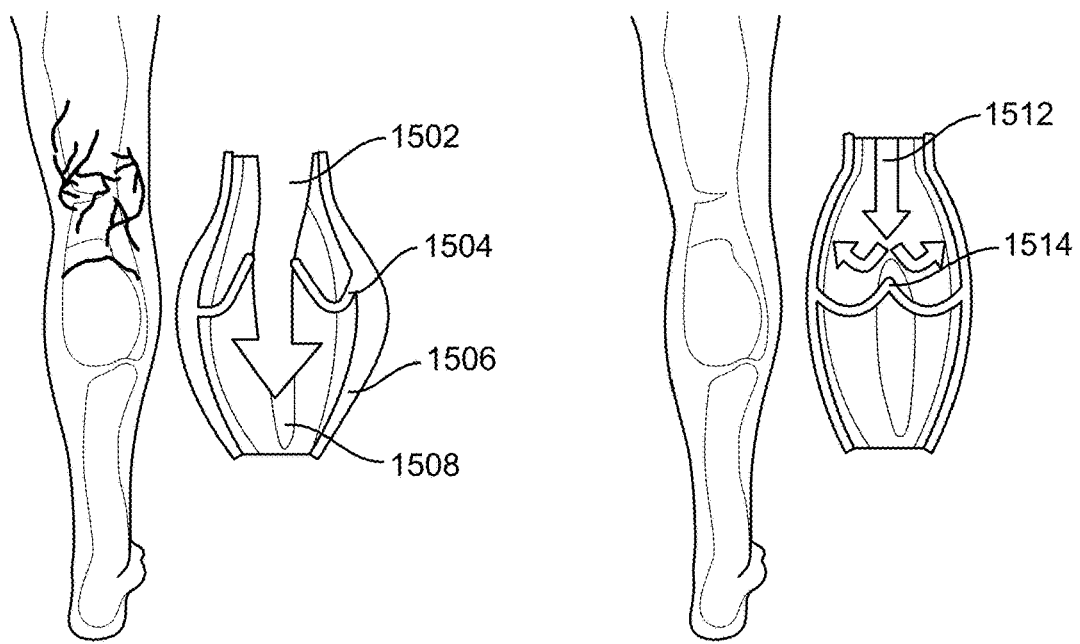
FIGS. 15A and 15B, respectively, 01 illustrate venous blood flow in healthy veins and varicose veins.

FIGS. 15A and 15B illustrate, respectively, venous blood flow in healthy veins and varicose veins. In FIG. 15B, healthy veins are shown. The arrow 1512 indicates blood flow. Also shown is a properly functioning valve 1514. In FIG. 15A, varicose veins are shown. The arrow 1502 indicates blood flow. A damaged valve 1504 is shown in the blood flow path. This damaged valve 1504 lead to a damaged and bulging vein wall 1506 and blood 1508 collecting in the vein. FIG. 15A makes clear how the distended and damaged walls of varicose veins likely form difficult to drain pockets of blood and fluid. Advantageously, the active aspiration step removes this blood and other fluids to prevent dilution of closure agent when injected.

Figure 27B:
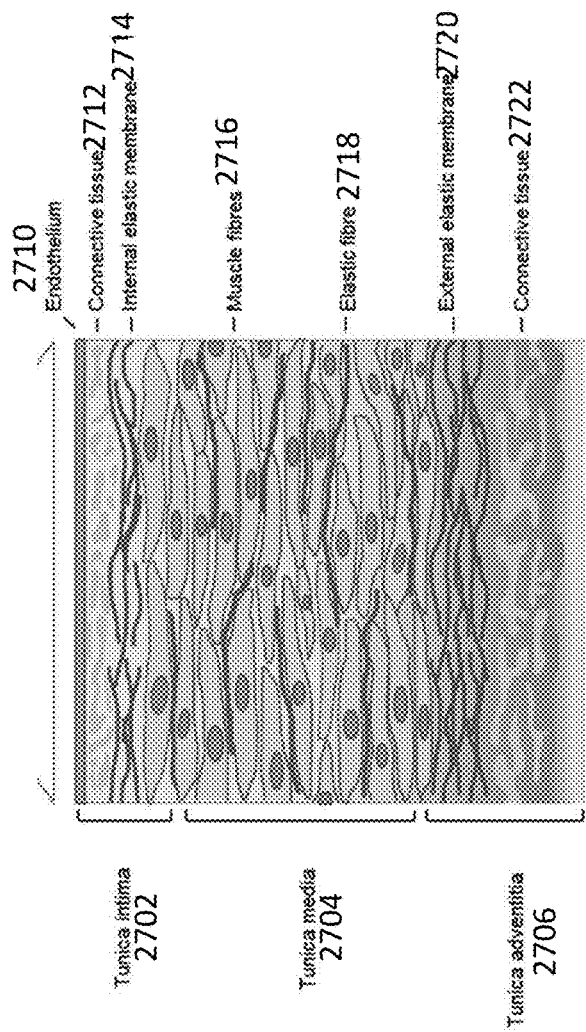
FIGS. 27A and 27B show exemplary venous wall anatomy.
Figure 27A:
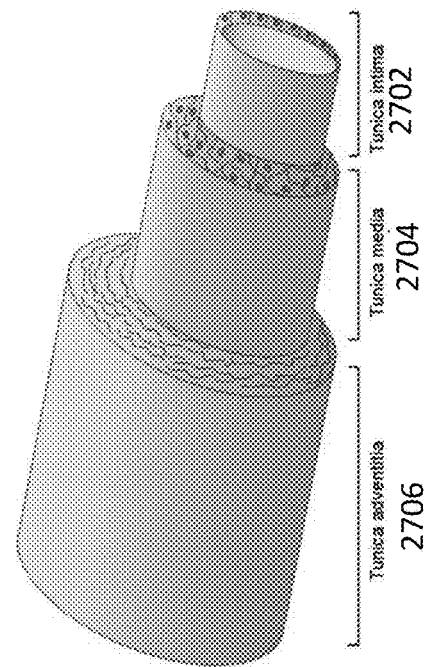

FIGS. 27A and 27B illustrate the anatomy of a vein. As shown in FIG. 27A, the vein wall comprises an inner layer, the tunica intima 2702, an intermediate layer, the tunica media 2704, and the outer layer, the tunica adventitia 2706. Moving to FIG. 27B, the tunica intima comprises the endothelium 2710, connective tissue 2712, and internal elastic membrane 2714. The tunica media comprises muscle fibers 2716, elastic fiber 2718. The tunica adventitia comprises an external elastic membrane 2720 and connective tissue 2722.

Advancing the at least partially inflated balloon through the closure zone does not perforate the vein and only causes minimal injury to the vein. In most embodiments, the combination of compliant balloon inflation and mechanical abrasion element engagement is optimized to result in only a very limited amount of damage to the vein wall, mostly nearly limited to the removal of all, most or some of the cells in the endothelial layer of the vein within the closure zone. The level of engagement produced by embodiments of the present invention stand in stark contrast to the more aggressive tissue engagement elements coupled to non-compliant balloons operating at pressures high above 1 atm. While desiring not to be bound by theory, it is believed that the various compliant or semi-compliant balloon treatment device embodiments described herein would be unable to address the clinical conditions anticipated by conventional non-compliant balloon therapy systems that are adapted and configured for deployment of vascular stents, engagement of an occluded or partially occluded vessel walls for the purpose of restoring vascularization by mechanical interactions with sufficient force and engagement to result in breaking, cutting or cracking calcified lesions causing the partial or complete occlusion. Because of the different operational requirements of the inventive elastomeric balloon embodiments herein, materials such as polyurethane or silicone or other materials that allow the inflation volumes described herein during mechanical abrasion element engagement as well as vein occlusion steps. In some configurations, the balloon may be expanded from 100% to up to 800% which is particularly useful given the variation in vein diameter that may be encountered within a closure zone or to achieve vessel occlusion given the elasticity of a vein wall. These and other design features of the various embodiments described herein stand in direct contrast to semi-compliant or mid-pressure balloon therapy systems and non-compliant or high-pressure balloon therapy systems. Semi-compliant (mid-pressure) balloons are commonly made of Pebax or higher durometer polyurethanes to still delivery much higher pressure than compliant balloons but with some degree of compliance that is not provided by the non-compliant balloon systems. Non-compliant (high-pressure) balloons are commonly made from polyester or nylon and are used in balloon treatment systems to expand to a specific, predefined diameter and exert high pressure when deployed.

As described herein, advancing the at least partially inflated balloon through the closure zone causes endothelial damage. In some embodiments, the degree of endothelial injury is a portion of the endothelium, for example, about half of the endothelial cells are lost. Other degrees of endothelial injury are also possible (e.g., ¼ of the endothelial cells are lost, ¾ of the endothelial cells are lost, etc.).

In some embodiments, the injury caused by the balloon therapy device is limited to the tunica intima. In some embodiments, the injury caused by the balloon therapy device is limited to the endothelium. In some embodiments, the injury caused by the balloon therapy device is limited to the endothelium and the connective tissue of the tunica intima. Other depths of injury are also contemplated.

In various embodiments, the balloon therapy device may be used for instillation of various medications into the isolated segment of vessel (i.e., sclerosant, chemotherapeutic agent, stem cells). The sclerosant may include sodium tetradecyl sulfate, polidocanol, or ethanolamine oleate, in some embodiments.

The side holes may be any shape including, but not limited to, oval, round, rectangular, or any other shape known in the art and as detailed elsewhere herein, for example as shown in FIGS. 10I-10L. The side holes are approximately spaced equally apart. In other embodiments, the side holes may be intermittently spaced apart or follow other patterns or regular or irregular arrays based on clinical need. The various embodiments may also be adapted for use of the balloon catheter with an over-the-wire design. Additionally or optionally, the balloon may be filed with saline or contrast depending on clinical need.

Optionally, the balloon may also include features, texturing, or a surface treatment on a portion of the balloon that will contact the vessel wall when the balloon is expanded. Examples include a zone of raised individual features (e.g., like those shown in FIGS. 10A-H) of any suitable shape and size for desired level of engagement with the tissue wall, a continuous or intermittent raised feature such as helical or spiral wrap, one or more or a series of continues or intermittent rings or hoops, portions of the surface that are roughened or bead blasted or otherwise treated to cause desired level of mechanical abrasion of the tissue, or combinations and modifications thereof. These and other modified alternative embodiments, may use one or a combination of tissue engagement features and positions that may enhance or modify the manner of preparing the treatment zone, creating desired vasospasm response or the desired amount of tissue mechanical abrasion to enhance closure agent effectiveness, if desired.

In an additional embodiment, the single balloon is provided with at least two elongate structures or mechanical engagement structures that are attached distally to the catheter at a location distal to the balloon.

Proximally, the elongated structures can be coupled to a slider on the catheter shaft proximal to the balloon. The elongate structures run along the length of the balloon. When the balloon is expanded, the elongate structures move along with the balloon and the slider moves closer to the balloon. When the balloon is deflated, the slider moves proximally and the elongate structures return to the stowed condition along the balloon outer surface.

The elongate mechanical abrasion elements or components of are positioned within sockets on a collar on the catheter shaft proximal to the balloon. When the balloon is expanded, the elongate structures move along with the balloon and the proximal end of the elongated structures move within the socket towards the balloon.

In some embodiments, the elongated structures enter elongate structure lumens provided within the catheter shaft through an aperture proximal to the balloon. When the balloon is expanded, the elongate structures move radially outwardly along with the balloon and a proximal portion of the elongate structures move distally within the elongate structure lumens proximal to the balloon. When the balloon is deflated, a proximal portion of the elongate structures move proximally within the elongate structure lumens.

Elongate mechanical abrasion elements or components of a mechanical abrasion structure may be metal or polymer or other suitable biocompatible material. The elongate structures or mechanical engagement structures may have any or a range of different cross sectional shape such as round, oval, rectangular, multi-sided, polygonal or hybrid or compound shapes. The structures are appropriately sized based on the vessel to be treated and the size of the balloon used. Exemplary diameters of mechanical engagement structures range from 0.1 mm, 0.2 mm, 0.3 mm, 0.4 mm, 0.5 mm or other sizes depending on clinical application and desired vessel wall interaction.

Additionally or optionally, the elongate structure may have a cross section shape in one portion that is curved to conform to the balloon outer surface and curvature. Another portion may have a cross section shape for adjusting the amount of engagement between the elongate structure and the adjacent wall. The elongate structure could be formed of a braid. The elongate structure may vary along its length. One region, such as where a partially inflated balloon would make contact with a vessel wall, may be adapted to provide aggressive engagement with the adjacent wall. In some embodiments, a sheath may be provided over the balloon and elongate structures. Relative movement between the sheath and the balloon and elongate structures may be used to allow the balloon to inflate and engage the elongate structure with the adjacent vessel structure, occlusion or wall.

The two balloon structures described above could be modified to use the elongate structure with the slider attached to the shaft proximal to the proximal balloon. In additional alternatives, the portion of the elongate elements between the balloons could be modified for additional functionality so that the two balloons provide an isolated treatment section while the elongate structures may be used to perform active engagement with the structures within the isolated treatment zone.

Figure 28A:
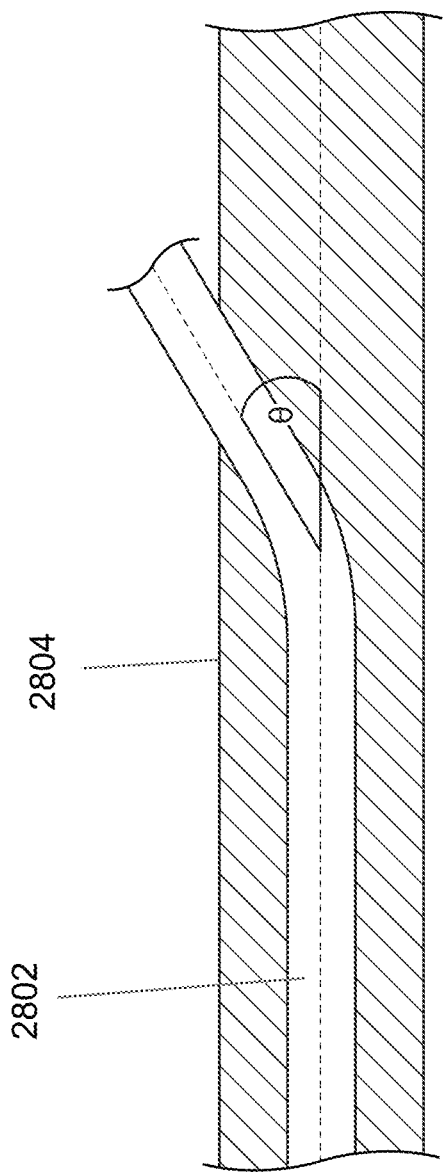
FIGS. 28A and 28B show embodiments of mechanical abrasion element lumens.

Referring now to FIG. 28A, an embodiment of an angled mechanical abrasion element lumen 2802 is shown. At or near its distal end, the mechanical abrasion element lumen 2801 angles towards the catheter shaft outer surface at a takeoff angle θ. The takeoff angle θ can vary from about 5-60°. For example, the takeoff angle θ can be 10, 15, 20, 25, 30, 35, 40, 45, 50, 55, or 60°. An angled mechanical abrasion element lumen provides a defined angle as the mechanical abrasion element transitions from the mechanical abrasion element lumen outwardly beyond the catheter shaft outer surface. An angled mechanical abrasion element lumen also provides a defined angle as the mechanical abrasion element transitions from the catheter shaft outer surface to the mechanical abrasion element lumen. An embodiment of a balloon therapy device with an angled mechanical abrasion element is shown in FIG. 23B.

Figure 28B:
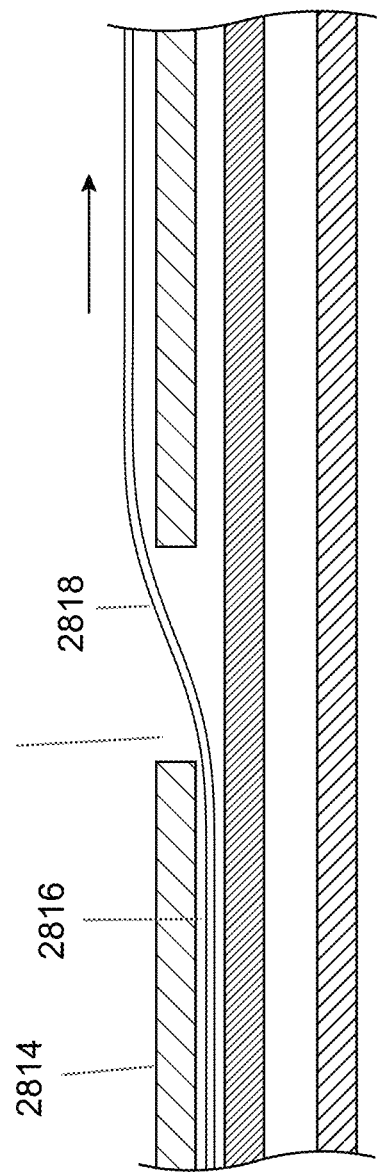

Moving to FIG. 28B, another embodiment of a balloon therapy device is shown. The device comprises an aperture 2812 formed in the catheter outer wall 2814 to be in communication with the mechanical abrasion element lumen 2816 so the mechanical abrasion element 2818 transitions across the aperture 2812 and forms a curved shape to allow a smooth transition from the mechanical abrasion element lumen 2816 to the outer catheter surface 2814. It is to be appreciated that other aperture dimensions and shapes may be used, as described elsewhere herein, for example as described with respect to FIGS. 3(*a*)-3(*e*).

Referring now to FIGS. 29A-31, embodiments of a balloon therapy device are shown. The devices comprise mechanical abrasion elements extending along the catheter shaft and balloon surface with both the proximal end and the distal end fixed relative to the catheter shaft. The mechanical abrasion elements can be configured to stretch and relax to accommodate balloon inflation and deflation.

In some embodiment, the mechanical abrasion elements extend within mechanical abrasion element lumens within the catheter shaft, as described above with respect to, for example, FIGS. 21A-K, 23A-B, and 28A-B. In some embodiments in which the mechanical abrasion elements extend within and emerge from lumens, the mechanical abrasion elements are fixed to the catheter shaft at or near the aperture where they enter/exit the mechanical abrasion element lumen, as shown in FIGS. 29A-29F. In some embodiments in which the mechanical abrasion elements extend within and emerge from lumens, the mechanical abrasion elements are fixed to the catheter shaft at another point, such as at a location within the catheter shaft (e.g., in the lumen).

Figure 29A:
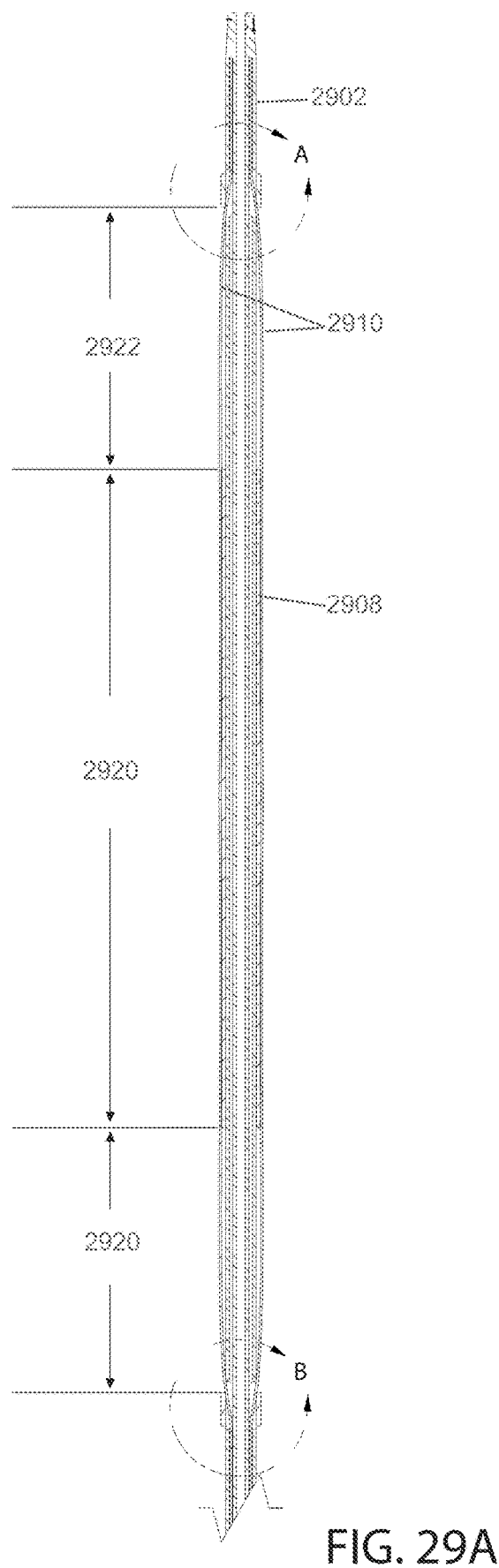
FIGS. 29A-29F show various views of an embodiment of a balloon therapy device.

Referring now to FIG. 29A, an embodiment of a balloon therapy device 2900 is shown. The device 2900 comprises mechanical abrasion element lumens (shown best in FIGS. 29B, C, E, and F) extending along the catheter shaft 2902. Similar to the devices shown in FIGS. 21A-K, 23A-B, and 28A-B, mechanical abrasion elements emerge from their lumens within the catheter shaft to extend along an outer surface of the balloon and a portion of the catheter shaft on either side of the balloon.

Figure 29B:
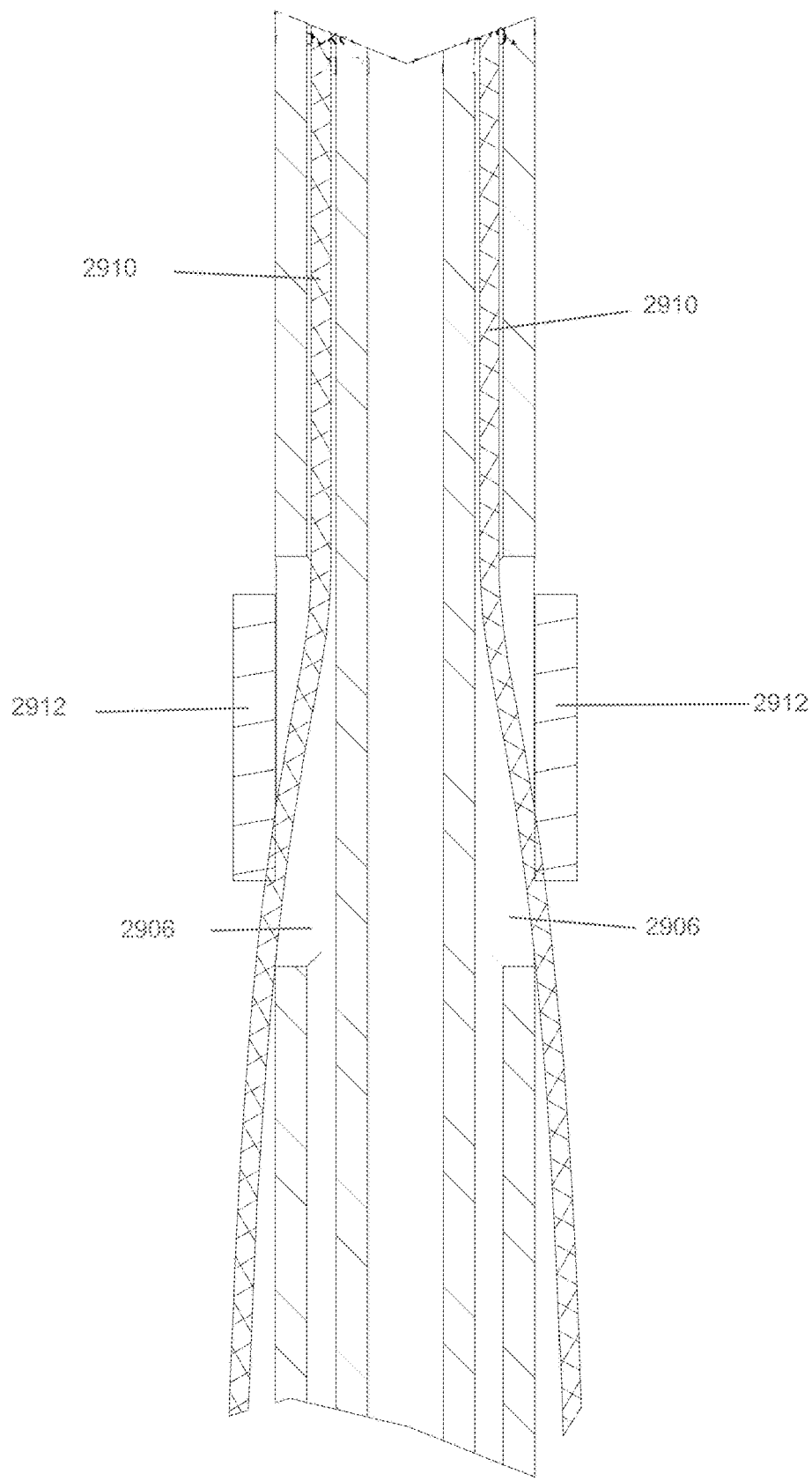
Figure 29C:
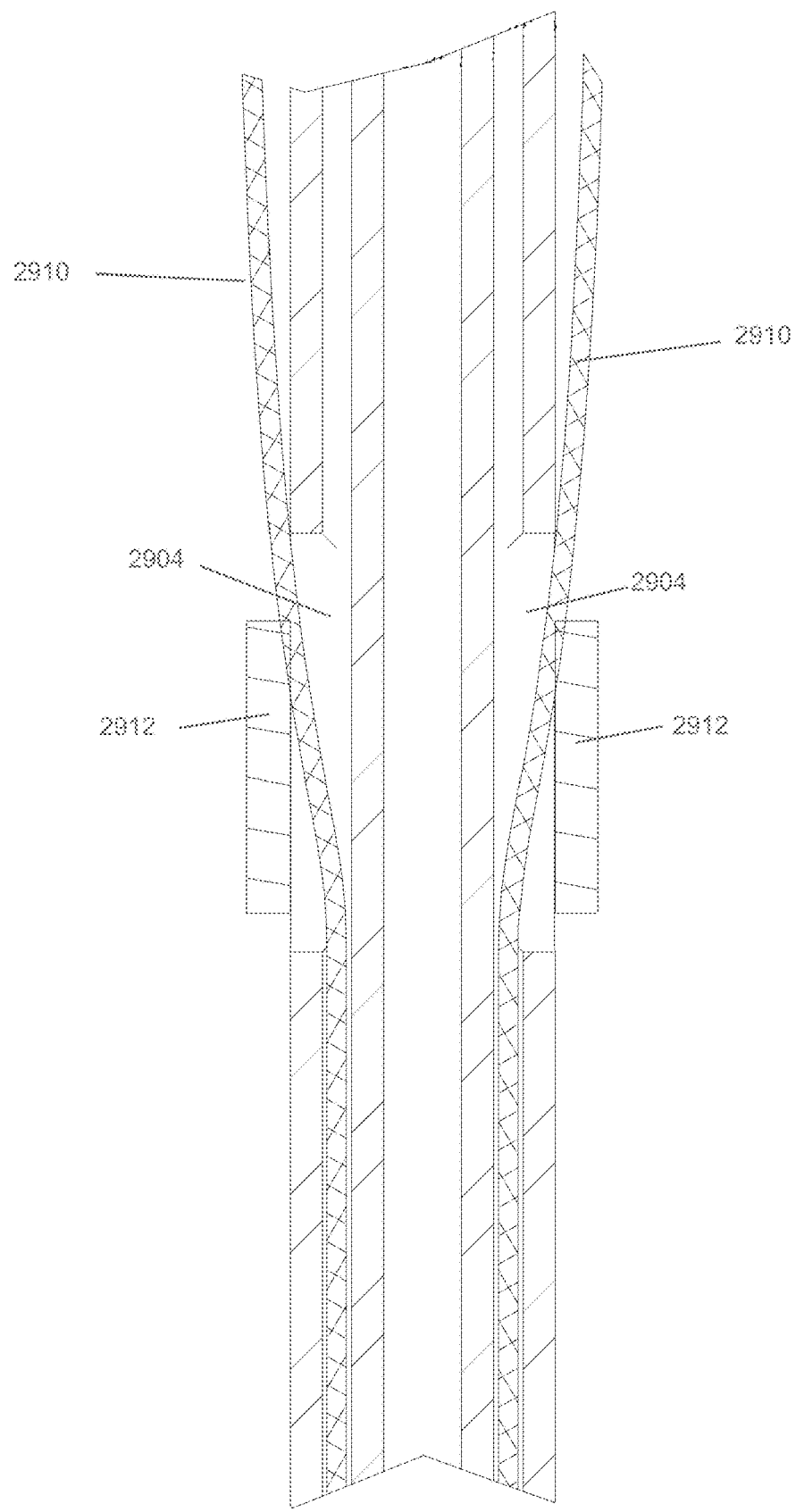

Moving to FIGS. 29B and 29C, enlarged views of section A (29B) and section B (29C) are shown. Each mechanical abrasion element transitions from inside the catheter shaft to outside the catheter shaft at an aperture 2904 proximal to the balloon 2908, and again at an aperture 2906 distal to the balloon 2908. The mechanical abrasion elements are fixed at component 2912. The fixation can be performed mechanically (e.g., using heatshrink 2912) or chemically (e.g., using adhesive bonding with a collar 2912, using adhesive bonding without a collar, etc.).

Figure 29D:
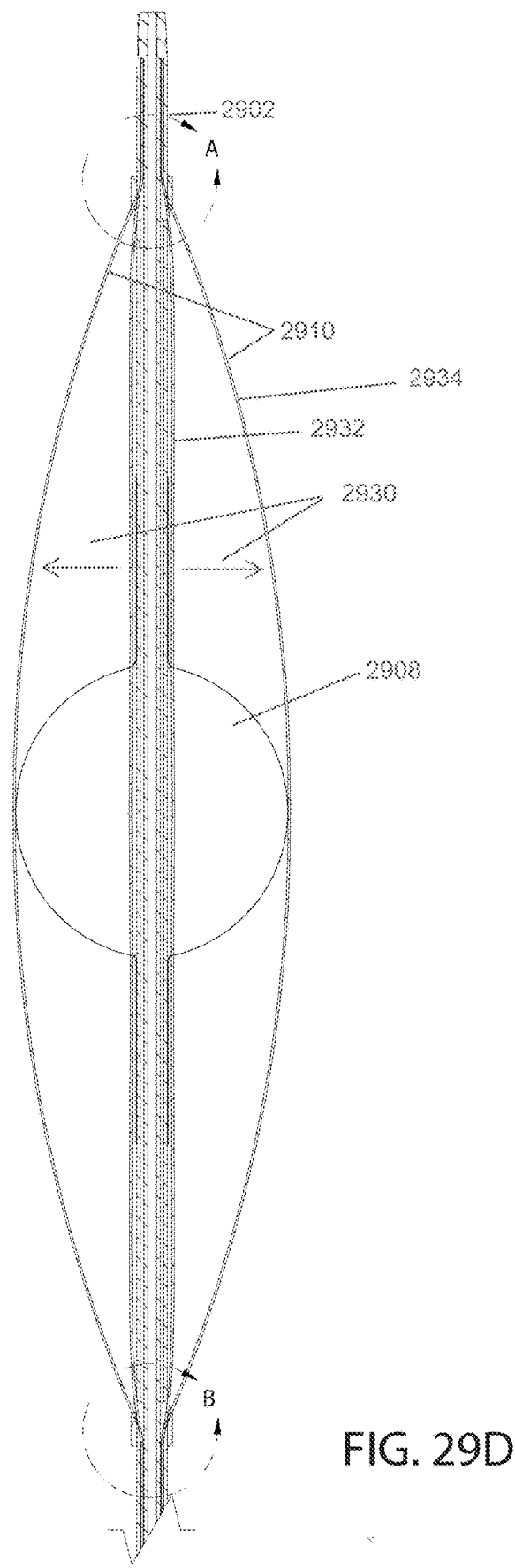

FIG. 29D shows the device 2900 with arrows 2930 indicating the deflection of the mechanical abrasion elements from a deflated balloon position 2932 to an inflated balloon position 2934. The mechanical abrasion elements deflect away from the catheter shaft upon inflation of the balloon. When the balloon is deflated, the mechanical abrasion elements deflect back towards the catheter shaft. Because the mechanical abrasion elements 2910 are fixed proximal and distal to the balloon, the mechanical abrasion elements can stretch to facilitate their deflection.

Figure 29E:
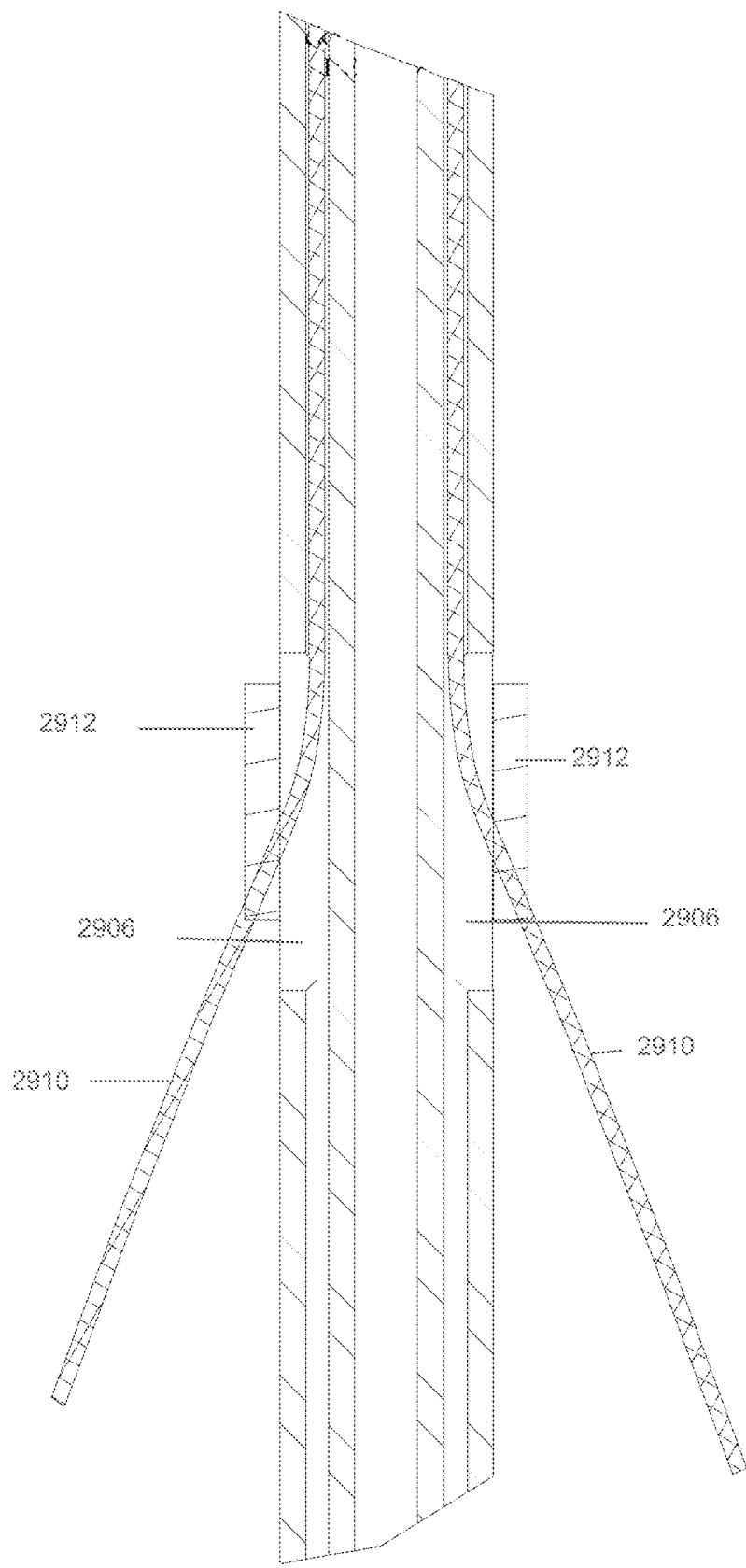
Figure 29F:
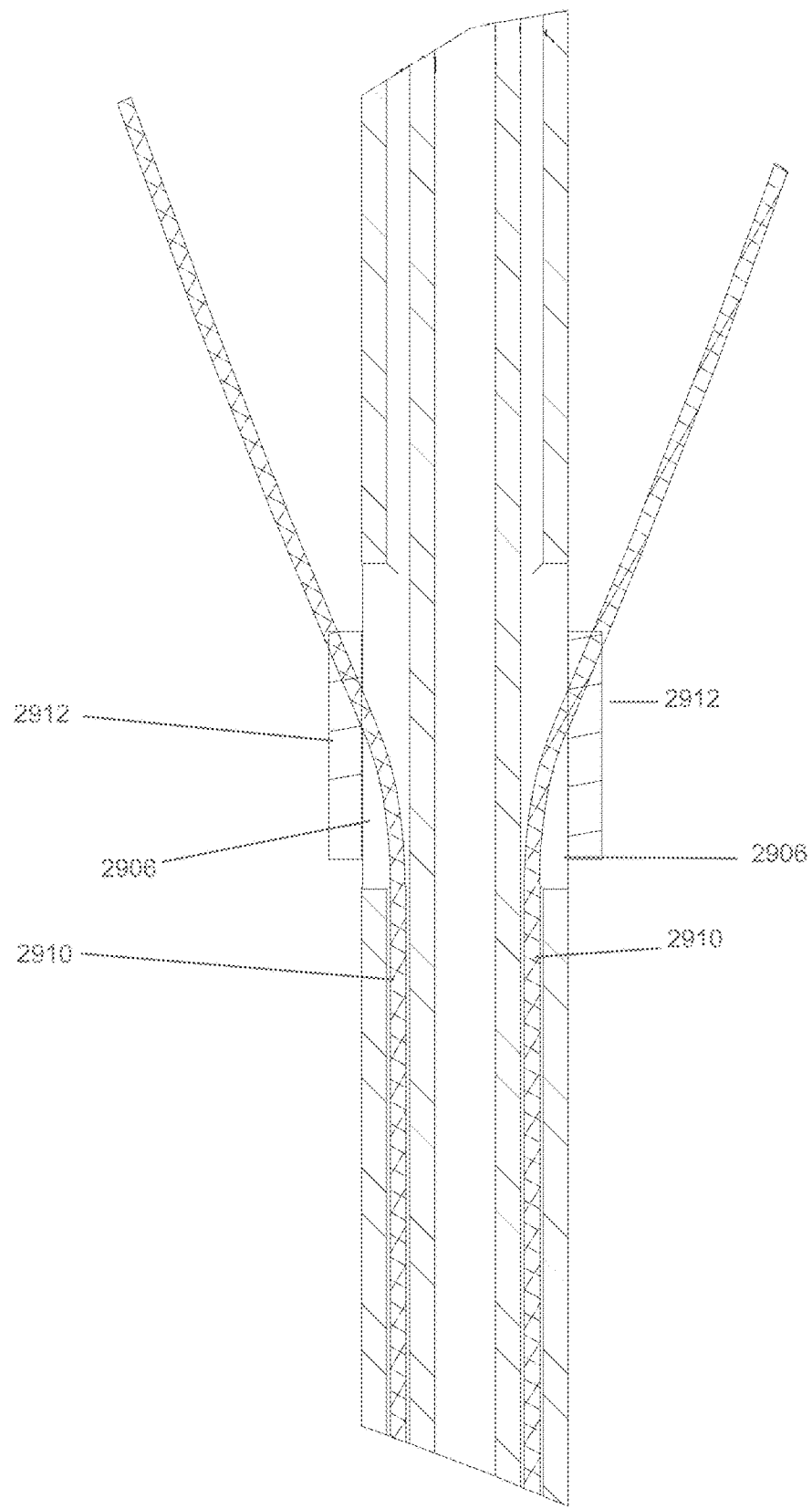

FIGS. 29E and 29F show enlarged views of section A (FIG. 29E), at the distal aperture 2904 and B (FIG. 29F) at the proximal aperture 2906 with the mechanical abrasion element only in the inflated balloon position. Fixation component 2912 fixes the mechanical abrasion element 2910 at the mechanical abrasion element apertures 2906, 2904. While FIGS. 29E and 29F show the mechanical abrasion element 2910 deflecting under a portion of the fixation component 2912, it will be appreciated that, in some embodiments, the mechanical abrasion element is fixed along an entire length of the fixation component 2912.

In some embodiments, the distance 2922 between the distal fixation component 2912 and the balloon is about 7-30 mm (or about 12-25 mm, or about 15-22 mm, etc.). In some embodiments, the distance 2920 between proximal fixation component 2912 and the balloon is about 5-22 mm (or about 7-20 mm, or about 10-17 mm, etc.).

In some embodiments, a length 2920 of the balloon is about 16-30 mm (or about 18-28 mm, or about 20-26 mm, etc.).

In some embodiments a total length of the mechanical abrasion element is about 100-190 mm (or about 110-180 mm, or about 120-170 mm, or about 130-160 mm).

In some embodiments, a length of the mechanical abrasion elements between fixation points is about 30-90 mm, or about 35-85 mm, or about 40-00 mm, or about 45-75 mm.

The mechanical abrasion element can have a circular cross section. Other configurations (e.g., slit or ribbon shaped, ovular, etc.) are contemplated.

A diameter or width of the mechanical abrasion element can be about 0.08-0.20 mm (or about 0.1-0.18 mm, 0.12-0.16 mm, etc.).

Figure 30B:
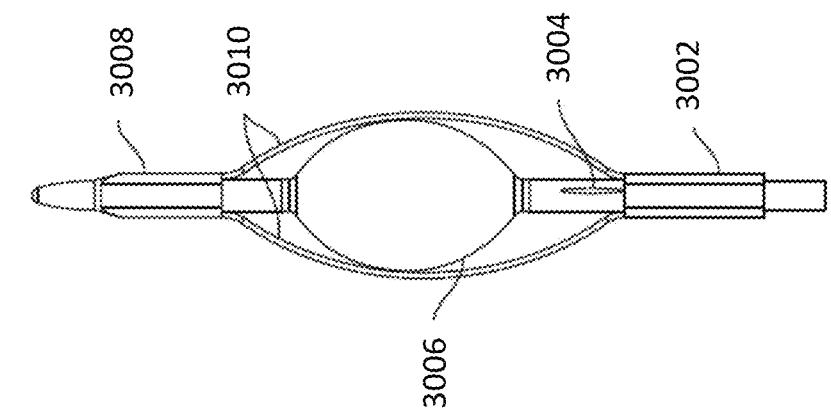
FIGS. 30A and 30B show top views of another embodiment of a balloon therapy device.
Figure 30A:
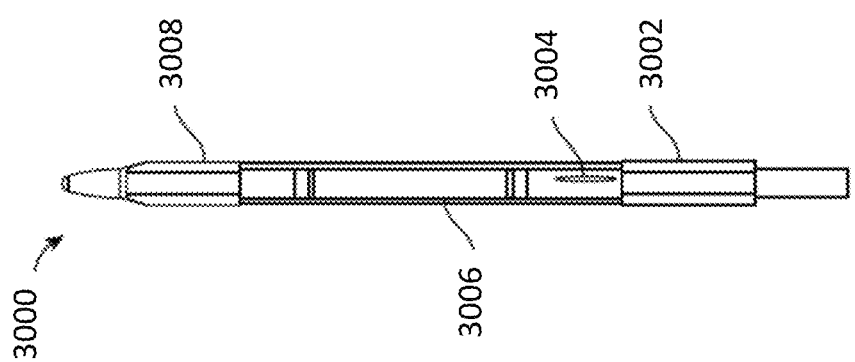

In some embodiments, as shown in FIGS. 30A and 30B the mechanical abrasion elements only extend externally to the catheter shaft and are fixed externally to the catheter shaft. FIGS. 30A and 30B show a top view of an embodiment of a balloon therapy device 3000 with the balloon deflated and the mechanical abrasion elements in a stowed configuration (FIG. 30A) and with the balloon inflated and the mechanical abrasion elements in an outwardly deflected configuration. The device 3000 comprises components similar to those describe with other embodiments herein, including a fluid aperture 3004 and a balloon 3006. The device 3000 comprises mechanical abrasion elements 3110 having ends that are fixed to an outer portion of the catheter shaft. The fixation can be performed mechanically (e.g., using heatshrink) or chemically (e.g., using adhesive bonding).

In some embodiments, as shown in FIGS. 30A and 30B, a collar can be used to fix or facilitate the fixation of the mechanical abrasion element relative to the catheter shaft. The device 3000 comprises a distal collar 3008 fixing the distal end of the mechanical abrasion elements 3110 to the catheter shaft and a proximal collar 3002 fixing the proximal ends of the mechanical abrasion elements 3010 to the catheter shaft. The mechanical abrasion elements can be fixed to an external surface of the catheter shaft and then covered by a collar. In other embodiments with a collar, the mechanical abrasion elements can be fixed to the collar, which can be fixed or attached to the external surface of the catheter shaft.

It will be appreciated that, in some embodiments, one end of the mechanical abrasion element can be external to the catheter shaft, as shown, for example, in FIGS. 30A and B, and the other end of the mechanical abrasion element can extend within a mechanical abrasion element lumen, as shown, for example in FIGS. 29A-29F.

As described herein, the fixation of the mechanical abrasion elements is different from the fixation used for the cutting or scoring element in cutting or scoring balloons. In those devices, because of the very high pressures used to uniformly inflate a non-compliant balloon and compress surrounding structures, a fixation stronger than mechanical or adhesive bonding is required. Many devices are instead formed as integral devices for placement over a non-compliant balloon instead of cutting or scoring elements attached to a balloon using mechanical or adhesive bonding.

The mechanical properties of the mechanical abrasion element can allow them to stretch to deflect and accommodate the inflation of the balloon and then return to their original shape extending along the catheter shaft. In some embodiments, the mechanical abrasion element is configured to stretch to about 30% of its length without permanent deformation.

In some embodiments, the mechanical abrasion element comprises Nitinol. Other materials are also contemplated.

For example, a shape memory material, such as nitinol can be deformed by the movement of the balloon but then return to its shape.

In some embodiments, the mechanical abrasion element can be shape set to aid in the mechanical abrasion elements return from a deflected, radially outwardly deflected position. For example, in some embodiments, the mechanical abrasion elements are shape set to extend along the catheter shaft. Inflation of the balloon will push them out of their shape set position. Upon deflation, the mechanical abrasion elements will tend to want to return to their shape set position extending along the catheter shaft.

In some embodiments, the mechanical abrasion element can be shape set to bow inwards towards the balloon, as shown in FIGS. 31A and 31B. FIG. 31A shows an embodiment of a balloon therapy device comprising a balloon 3106, fluid aperture, and mechanical abrasion elements 3110 fixed by a distal collar 3108 and a proximal collar 3102. FIG. 31B shows an embodiment of a balloon therapy device 3140 comprising a balloon 3146 and mechanical abrasion elements 3142 extending from mechanical abrasion element lumens and fixed by distal collar 3148 and configured to slide (e.g., e.g., back along the dedicated lumen as shown in FIG. 31B, within a sliding collar, within sockets of a collar) at their proximal end.

Inflation of the balloon pushes the mechanical abrasion elements out of their shape set configuration. In some embodiments, the mechanical abrasion element can be shape set such that, at room temperature (e.g., less than about 26° C., the mechanical abrasion elements extend along the catheter shaft in a generally straight configuration. At body temperature, the mechanical abrasion elements bow in towards the balloon, as shown in FIG. 31A. It will be appreciated that the mechanical abrasion elements 3110 of FIG. 31A do not sit flush against the catheter shaft so that bowing in at body temperature is visible. In contrast, the mechanical abrasion elements of FIG. 31B sit flush against the catheter shaft, so though the mechanical abrasion elements are biased inwards at body temperature, they do not visibly bow in towards the catheter shaft at body temperature.

After the procedure is completed and the balloon is allowed to deflate from the occlusion state, the shape set element will want to push back to the closed position, thereby causing the restoring force to deflect the mechanical abrasion element inward towards the catheter. In the embodiment of FIG. 31B, the restoring force helps to urge the free end of the mechanical abrasion element to slide proximally (e.g., back along the dedicated lumen as shown in FIG. 31B, within a sliding collar, within sockets of a collar).

In various alternative embodiments, a mechanical abrasion structure may include an arrangement of one or more mechanical abrasion elements about at least one balloon of a balloon therapy device. The one or more mechanical abrasion elements are adapted and configured to move variously axially or radially relative to the catheter shaft in response to changes in a balloon state of a directly adjacent balloon. Changes in a balloon state include, for example, changing from a deflated state to a partially inflated state, to an incrementally inflated state or incrementally deflated state, or to an inflated state corresponding to an occlusion condition and then in the corresponding states in a transition back to a deflated state.

In general, each mechanical abrasion element has a distal end, a tissue engagement portion and a proximal end. In some embodiments, the distal end of each of the mechanical engagement elements is fixed relative to a catheter shaft while the proximal end is free to slide relative to the longitudinal axis of the catheter shaft. In some embodiments, a mechanical abrasion element proximal end is secured into a sliding collar. In some embodiments, a mechanical abrasion element proximal end is sized and configured to slide within a dedicated lumen that is within or adjacent to the catheter outer sidewall.

In some embodiments, the distal and proximal ends of each mechanical abrasion element are fixed relative to the catheter. In certain such embodiments, the mechanical abrasion element stretches in response to balloon inflation, and relaxes in response to balloon deflation.

In some embodiments, the tissue engagement portion of a mechanical abrasion element may additionally include an inner surface adapted and configured to correspond to a curvature of the balloon so as to facilitate movement of the mechanical abrasion element in response to balloon volume and shape change. In other alternative embodiments, an outer surface of the tissue engagement portion of a mechanical abrasion element may be modified, adapted or variously configured to cause a controllable level of damage to at least one layer or a portion of one layer of a wall of the diseased vein and at least one incompetent valve within a closure zone.

Figure 16:
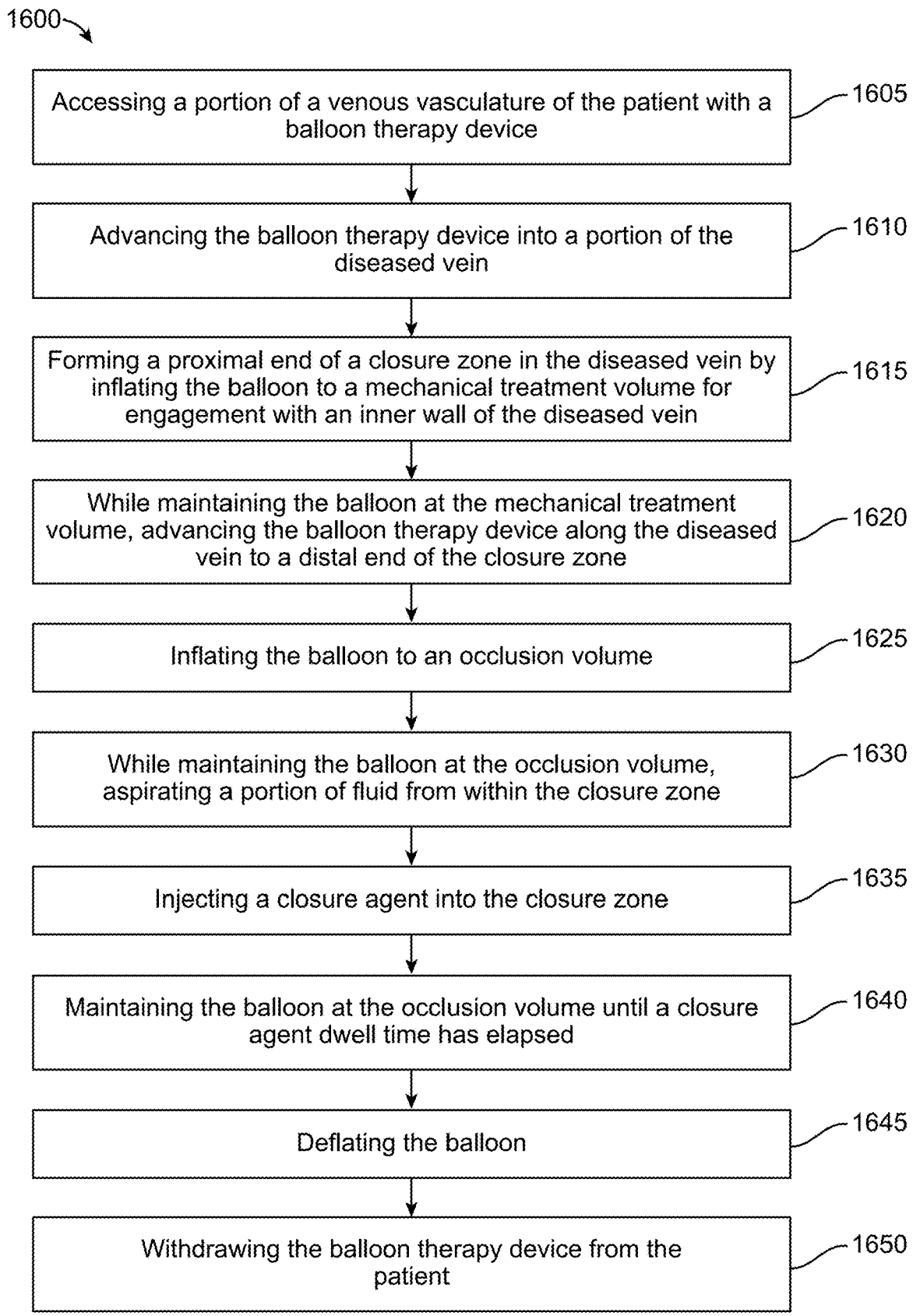
FIG. 16 is a flow chart of an exemplary balloon mechanical therapy treatment method 1600 carried out in steps 1605-1650.

FIG. 16 is a flow chart of an exemplary balloon mechanical therapy treatment method 1600 carried out in steps 1605-1650. In step 1605, the method comprises accessing a portion of a venous vasculature of a patient with a balloon therapy device. In some embodiments, the device can be advanced over a guidewire.

In step 1610, the method comprises advancing the balloon therapy device into a portion of the diseased vein.

In step 1615, the method comprises forming a proximal end of a closure zone in the diseased vein by inflating the balloon to a mechanical treatment volume for engagement with an inner wall of the diseased vein.

In some embodiments, inflating the balloon to a mechanical treatment volume comprises visualizing the balloon using imaging (e.g., ultrasound guidance) and inflating it until it contact the vein wall. At that point, the clinician can stop inflating or inflate about an additional 0.25-0.5 cc. Additional inflation may be needed to accommodate changes in vessel diameter along the length of the closure zone.

Inflating the balloon can comprise attaching a syringe to the inflation port and inflating the balloon with a fluid, such as saline, contrast or air. The inflation level can be adjusted throughout the method, using the syringe.

In step 1620, the method comprises advancing the balloon therapy device along the diseased vein to a distal end of the closure zone while maintaining the balloon at the mechanical treatment volume.

In step 1625 the method comprises inflating the balloon to an occlusion volume.

The occlusion volume can vary based on, for example, the balloon size and vessel size. In some embodiments, the occlusion volume is about 2-3 cc.

The method comprises aspirating a portion of fluid from within the closure zone while maintaining the balloon at the occlusion volume at step 1630.

In step 1635, a closure agent is injected into the closure zone.

At step 1640, the method comprises maintaining the balloon at the occlusion volume until a closure agent dwell time has elapsed.

In some embodiments, the dwell time comprises about 2-5 minutes. The dwell time may be as long as 10 minutes and may vary based on the recommended uses of a particular closure agent.

The method comprises deflating the balloon at step 1645.

Deflating the balloon can comprise using the syringe to remove fluid from the balloon. In some embodiments, deflating the balloon comprises completely deflating the balloon. In some embodiments, deflating the balloon comprises mostly deflating the balloon (e.g., greater than about 90% of its volume).

The method comprises withdrawing the balloon therapy from the patient at step 1650.

It will be appreciated that the method 1600 can include any other variation or additions as described herein.

Figure 17:
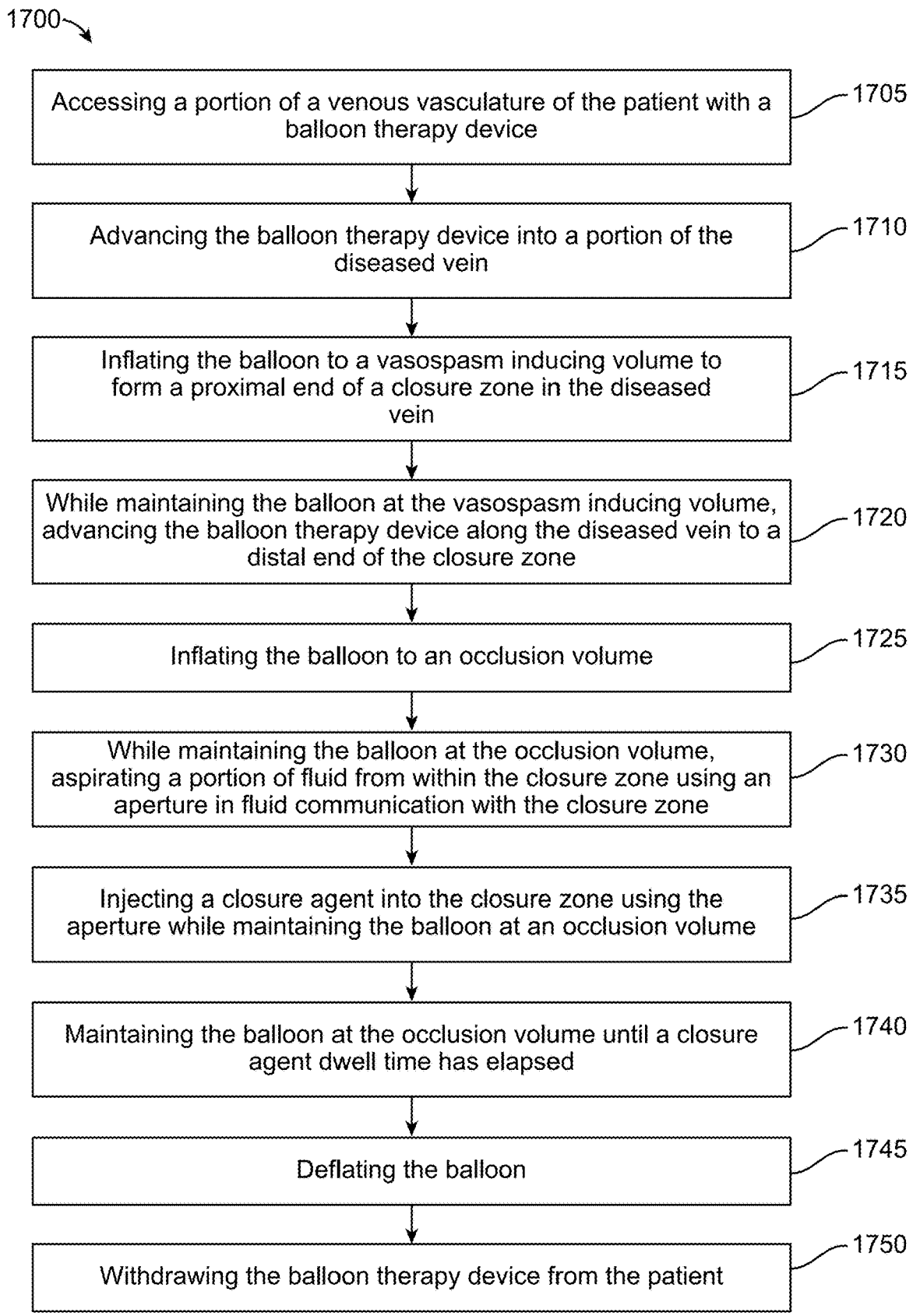
FIG. 17 is a flow chart of an exemplary balloon therapy treatment method 1700 inducing vasospasm/endothelium injury and carried out in steps 1705-1750.

FIG. 17 is a flow chart of an exemplary balloon therapy treatment method 1700 inducing vasospasm/endothelial injury and carried out in steps 1705-1750. Unless described otherwise, the steps can be similar to those described with respect to FIG. 16.

At step 1705, the method comprises accessing a portion of a venous vasculature of the patient with a balloon therapy device. The method can comprise advancing the device over a guidewire.

The method comprises advancing the balloon therapy device into a portion of the diseased vein at step 1710.

At step 1715, the method comprises inflating the balloon to a venospasm inducing volume to form a proximal end of a closure zone in the diseased vein.

In some embodiments, inflating the balloon to a venospasm inducing volume comprises visualizing the balloon using imaging (e.g., ultrasound guidance) and inflating it until it contacts the vein wall. At that point, the clinician can stop inflating or inflate about an additional 0.25-0.5 cc. Additional inflation may be needed to accommodate changes in vessel diameter along the length of the closure zone.

Inflating the balloon can comprise attaching a syringe to the inflation port and inflating the balloon with a fluid, such as saline. The inflation level can be adjusted throughout the method, using the syringe.

At step 1720, the method comprises advancing the balloon therapy device along the diseased vein to a distal end of the closure zone. In some embodiments, the method comprises engaging mechanical abrasion elements with the vessel wall while advancing the balloon therapy device along the diseased vein.

At step 1725, the method comprises inflating the balloon to an occlusion volume.

The occlusion volume can vary based on, for example, the balloon size and vessel size. In some embodiments, the occlusion volume is about 2-3 cc.

The method comprises aspirating a portion of fluid from within the closure zone using an aperture in fluid communication with the closure zone at step 1730.

In some embodiments, the method comprises aspirating all of the fluid from within the closure zone. in some embodiments, the method comprises most (e.g., greater than 50%, greater than 60%, greater than 70%, greater than 80%, greater than 90%, etc.) of the fluid from within the closure zone.

At step 1735, the method comprises injecting a closure agent into the closure zone using the aperture while maintaining the balloon at an occlusion volume.

The method comprises maintaining the balloon at the occlusion volume until a closure agent dwell time has elapsed.

At step 1745, the method comprises deflating the balloon.

Deflating the balloon can comprise using the syringe to remove fluid from the balloon. In some embodiments, deflating the balloon comprises completely deflating the balloon. In some embodiments, deflating the balloon comprises mostly deflating the balloon (e.g., greater than about 90% of its volume).

At step 1750, the method comprises withdrawing the balloon therapy device from the patient.

Figure 18:
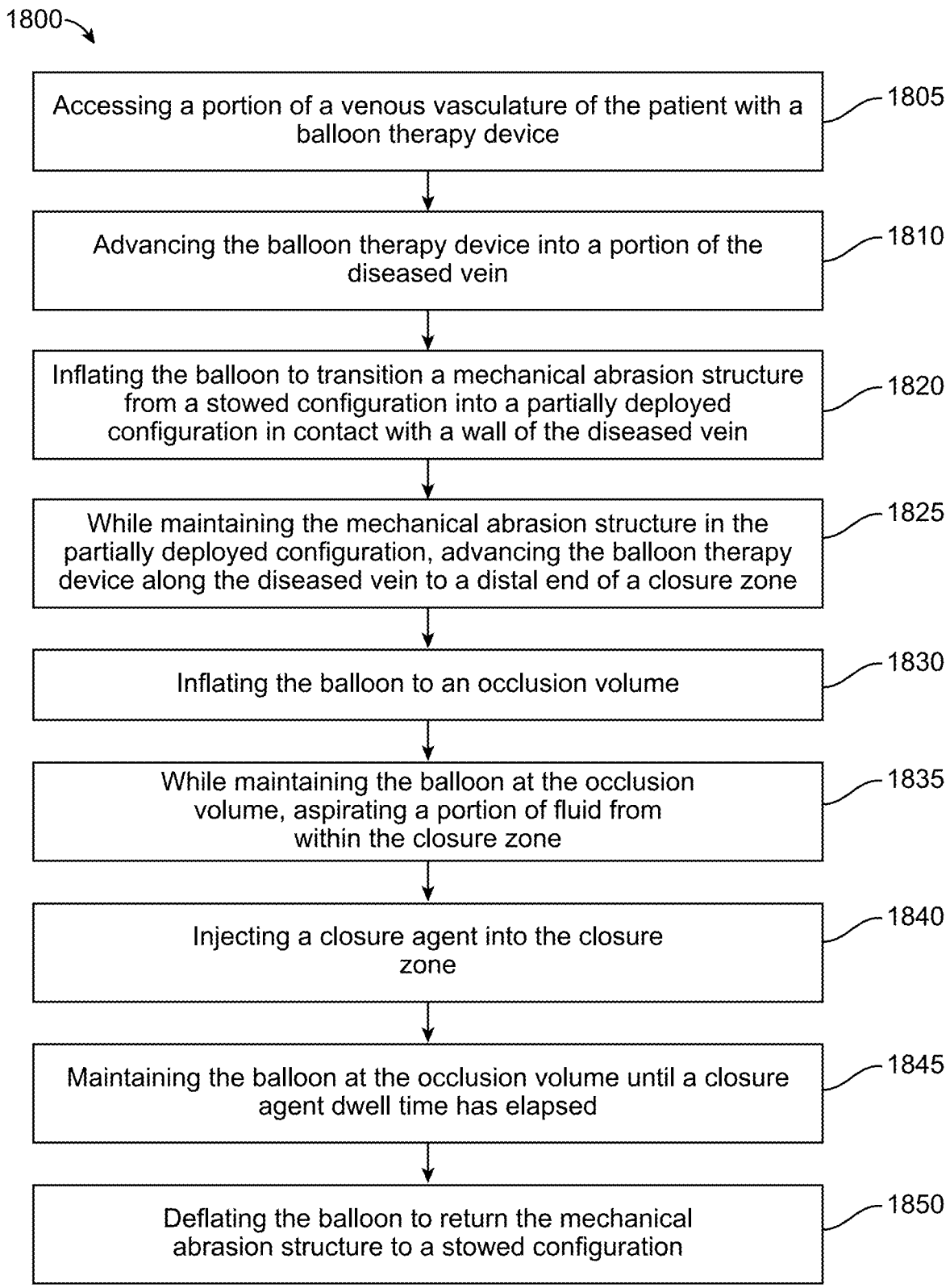
FIG. 18 is a flow chart of an exemplary balloon therapy treatment method 1800 employing a mechanical abrasion structure and carried out in steps 1805-1850.

FIG. 18 is a flow chart of an exemplary balloon therapy treatment method 1800 employing a mechanical abrasion structure and carried out in steps 1805-1850. Unless described otherwise, the method can comprise similar steps to those carried out and described with respect to FIGS. 16 and 17.

The method comprises accessing a portion of a venous vasculature of the patient with a balloon therapy device at step 1805. The method can comprise advancing the device over a guidewire.

At step 1810, the method comprises advancing the balloon therapy device into a portion of the diseased vein.

At step 1820, the method comprises inflating the balloon to transition a mechanical abrasion structure from a stowed configuration into a partially deployed configuration in contact with a wall of the diseased vein.

In some embodiments, inflating the balloon to transition a mechanical abrasion structure from a stowed configuration into a partially deployed configuration comprises visualizing the balloon using imaging (e.g., ultrasound guidance) and inflating it until it contacts the vein wall. At that point, the clinician can stop inflating or inflate about an additional 0.25-0.5 cc. Additional inflation may be needed to accommodate changes in vessel diameter along the length of the closure zone.

Inflating the balloon can comprise attaching a syringe to the inflation port and inflating the balloon with a fluid, such as saline. The inflation level can be adjusted throughout the method, using the syringe.

The method comprises advancing the balloon therapy device along the diseased vein to a distal end of a closure zone while maintaining the mechanical abrasion structure in the partially deployed configuration at step 1825. It will be appreciated that this advancement with the mechanical abrasion elements at least partially deployed may induce venospasm within at least a portion of the closure zone.

At step 1830, the method comprises inflating the balloon to an occlusion volume.

The occlusion volume can vary based on, for example, the balloon size and vessel size. In some embodiments, the occlusion volume is about 2-3 cc.

The method comprises aspirating a portion of fluid from within the closure zone at step 1835.

In some embodiments, the method comprises aspirating all of the fluid from within the closure zone. In some embodiments, the method comprises most (e.g., greater than 50%, greater than 60%, greater than 70%, greater than 80%, greater than 90%, etc.) of the fluid from within the closure zone.

At step 1840, the method comprises injecting a closure agent into the closure zone.

The method comprises maintaining the balloon at the occlusion volume until a closure agent dwell time has elapsed at step 1845.

In some embodiments, the dwell time is about 2-5 minutes.

At step 1850, the method comprises deflating the balloon to return the mechanical abrasion structure to a stowed configuration.

Deflating the balloon can comprise using the syringe to remove fluid from the balloon. In some embodiments, deflating the balloon comprises completely deflating the balloon. In some embodiments, deflating the balloon comprises mostly deflating the balloon (e.g., greater than about 90% of its volume).

The method can further comprise withdrawing the device.

Figure 19:
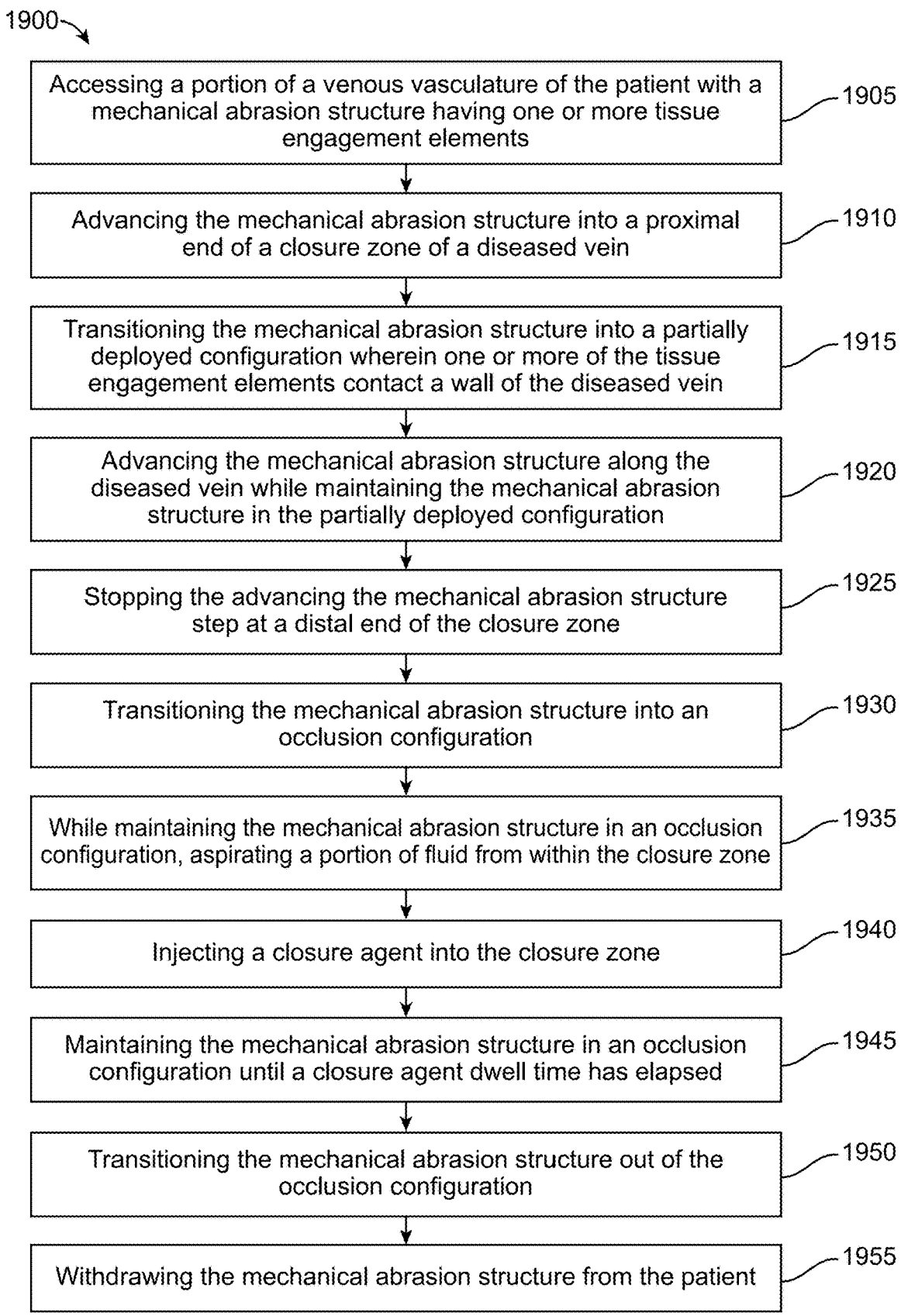
FIG. 19 is a flow chart of an exemplary balloon therapy treatment method 1900 employing a mechanical abrasion structure and one or more tissue engagement elements carried out in steps 1905-1955.

FIG. 19 is a flow chart of an exemplary balloon therapy treatment method 1900 employing a mechanical abrasion structure and one or more tissue engagement elements carried out in steps 1905-1955. Unless described otherwise, FIG. 19 can comprise steps similar to those described with respect to FIGS. 16-18.

At step 1905, the method comprises accessing a portion of a venous vasculature of the patient with a mechanical abrasion structure having one or more tissue engagement elements.

The method can comprise advancing the device over a guidewire.

At step 1910, the method comprises advancing the mechanical abrasion structure into a proximal end of a closure zone of a diseased vein.

The method comprises transitioning the mechanical abrasion structure into a partially deployed configuration wherein one or more of the tissue engagement elements contacts a wall of the diseased vein at step 1915.

In some embodiments, inflating the balloon to transition a mechanical abrasion structure into a partially deployed configuration comprises visualizing the balloon using imaging (e.g., ultrasound guidance) and inflating it until it contacts the vein wall. At that point, the clinician can stop inflating or inflate about an additional 0.25-0.5 cc. Additional inflation may be needed to accommodate changes in vessel diameter along the length of the closure zone.

At step 1920, the method comprises advancing the mechanical abrasion structure along the diseased vein while maintaining the mechanical abrasion structure in the partially deployed configuration. It will be appreciated that this advancement with the mechanical abrasion elements at least partially deployed may induce venospasm and/or collapse within at least a portion of the closure zone.

The method can comprise stopping the advancing of the mechanical abrasion structure step at a distal end of the closure zone.

At step 1930, the method comprises transitioning the mechanical abrasion structure into an occlusion configuration.

In some embodiments, transitioning the mechanical abrasion structure into an occlusion configuration comprises inflating a balloon to an occlusion volume and moving the mechanical abrasion structure towards the venous walls.

The occlusion volume can vary based on, for example, the balloon size and vessel size. In some embodiments, the occlusion volume is about 2-3 cc.

The method comprises aspirating a portion of fluid from within the closure zone while maintaining the mechanical abrasion structure in an occlusion configuration, at step 1935.

In some embodiments, the method comprises aspirating all of the fluid from within the closure zone. In some embodiments, the method comprises most (e.g., greater than 50%, greater than 60%, greater than 70%, greater than 80%, greater than 90%, etc.) of the fluid from within the closure zone.

At step 1940, the method comprises injecting a closure agent into the closure zone.

The method comprises maintaining the mechanical abrasion structure in an occlusion configuration until a closure agent dwell time has elapsed, at step 1945.

In some embodiments, the closure agent dwell time is about 2-5 minutes.

At step 1950, the method comprises transitioning the mechanical abrasion structure out of the occlusion configuration.

In some embodiments, transitioning the mechanical abrasion structure out of the occlusion configuration comprises at least partially deflating a balloon on the device, thereby moving the mechanical abrasion structure away from the venous wall.

Deflating the balloon can comprise using the syringe to remove fluid from the balloon. In some embodiments, deflating the balloon comprises completely deflating the balloon. In some embodiments, deflating the balloon comprises mostly deflating the balloon (e.g., greater than about 90% of its volume).

The method comprises withdrawing the mechanical abrasion structure from the patient at step 1955.

FIG. 20 is a flow chart of an exemplary two balloon therapy treatment method 2000 carried out in steps 2005-2050. Unless described otherwise, the method 2000 can comprise steps similar to those described with respect to FIGS. 16-19.

The method comprises advancing a guidewire into a portion of the diseased vein, at step 2005.

At step 2010, the method comprises advancing a dual balloon therapy device having a first balloon and a second balloon over the guidewire until the distal end of the distal balloon is positioned at a proximal end of a closure zone of the diseased vein.

The method comprises partially inflating the first balloon and the second balloon to a mechanical treatment volume in contact with an interior wall of the diseased vein, at step 2015. This amount will vary depending on the patient, vein size and other factors but will typically range between 0.25 to 0.5 cc. Sufficient contact may be based on tactile feedback based on catheter movement or by confirming with imaging as discussed below.

In some embodiments, inflating the balloons to a mechanical treatment volume comprises visualizing the balloon using imaging (e.g., ultrasound guidance) and inflating it until it contacts the vein wall. At that point, the clinician can stop inflating or inflate about an additional 0.25-0.5 cc. Additional inflation may be needed to accommodate changes in vessel diameter along the length of the closure zone.

The method comprises advancing the first and the second balloon along the diseased vein until the distal end of the closure zone is reached, at step 2020.

In some embodiments, advancing the first and the second balloon along the diseased vein causes venospasm and/or collapse.

The method comprises inflating the first and the second balloons to an occlusion volume, at step 2025.

The occlusion volume can vary based on, for example, the balloon size and vessel size. In some embodiments, the occlusion volume is about 2-3 cc.

At step 2030, the method comprises aspirating a fluid from the closure zone while maintaining the first and the second balloons at an occlusion volume. Aspirating a fluid from the closure zone can comprise aspirating fluid through an aperture on the device.

In some embodiments, the method comprises aspirating all of the fluid from within the closure zone. In some embodiments, the method comprises most (e.g., greater than 50%, greater than 60%, greater than 70%, greater than 80%, greater than 90%, etc.) of the fluid from within the closure zone.

The method can comprise injecting a closure agent into the closure zone in a space between the proximal end of the first balloon and the distal end of the second balloon at step 2035.

At step 2040, the method comprises maintaining the first balloon and the second balloon at the occlusion pressure until a closure agent dwell time has elapsed.

In some embodiments, the closure agent dwell time is about 2-5 minutes.

In some embodiments, the method comprises aspirating all of the fluid from within the closure zone. In some embodiments, the method comprises most (e.g., greater than 50%, greater than 60%, greater than 70%, greater than 80%, greater than 90%, etc.) of the fluid from within the closure zone.

The method comprises at least partially deflating the first balloon and the second balloon at step 2045.

At least partially deflating the balloons can comprise using the syringe to remove fluid from the balloons. In some embodiments, deflating the balloons comprises completely deflating the balloons. In some embodiments, deflating the balloon comprises mostly deflating the balloons (e.g., greater than about 90% of its volume).

At step 2050, the method can comprise withdrawing the dual balloon therapy device from the patient, in some embodiments.

Figure 24:
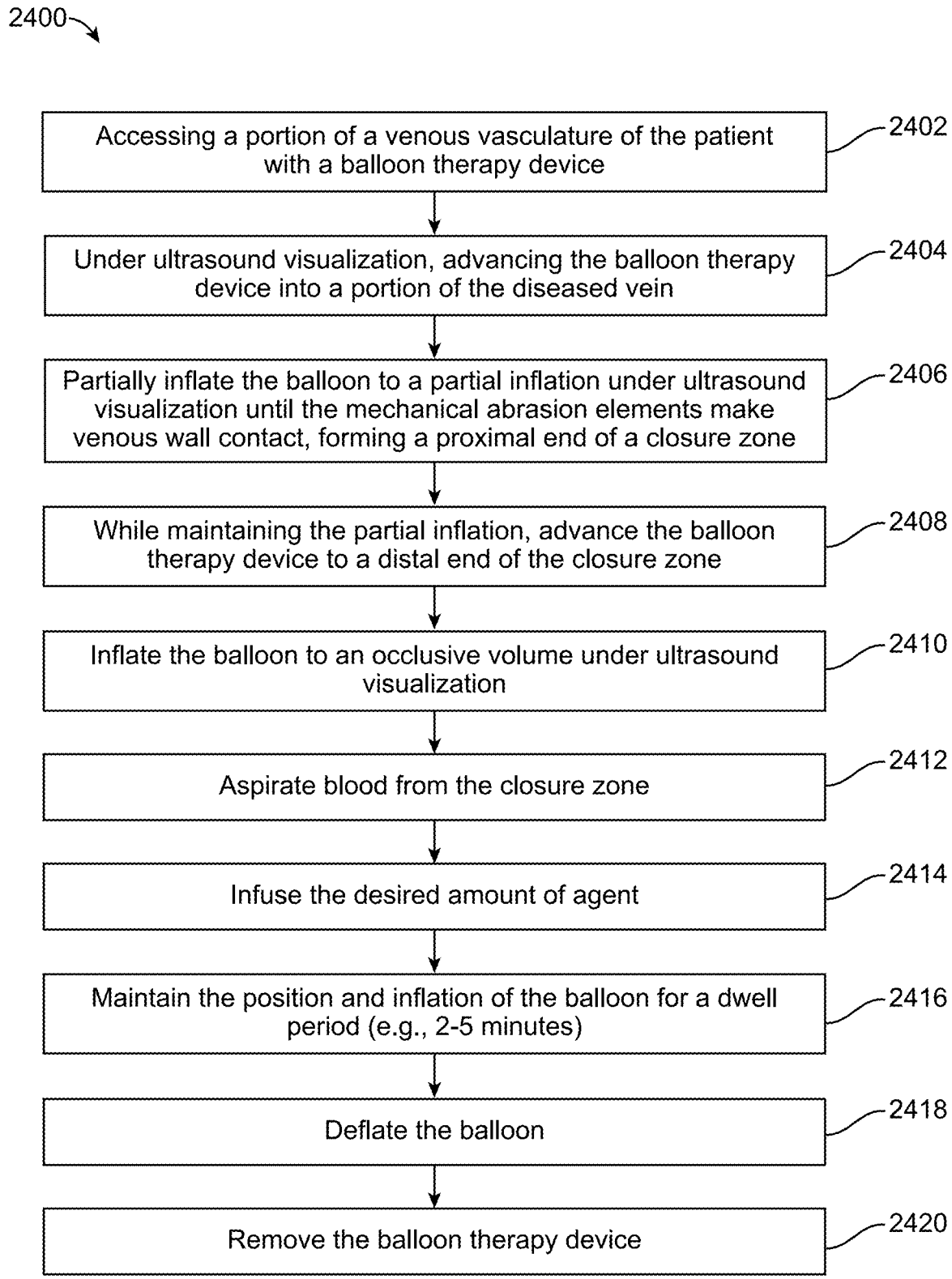
FIG. 24 is a flow chart of an exemplary balloon therapy treatment method 2400 employing a mechanical abrasion structure and carried out in steps 2402-2420.

FIG. 24 is a flow chart showing a balloon therapy treatment method 2400 employing a mechanical abrasion element carried out in steps 2402-2420.

At step 2402, the method comprises accessing a portion of a venous vasculature of the patient with a balloon therapy device.

The method comprises advancing the balloon therapy device into a portion of the diseased vein under ultrasound visualization at step 2404.

At step 2406, the method comprises partially inflating the balloon to a partial inflation under ultrasound visualization until the mechanical abrasion elements make venous wall contact, forming a proximal end of a closure zone.

Inflating until the mechanical abrasion elements make venous wall contact can comprise inflating until or just past (e.g., 0.25-0.5 cc additional) the point at which the clinician sees venous wall contact using ultrasound visualization.

The method comprises advancing the balloon therapy device to a distal end of the closure zone while maintaining the partial inflation at step 2408.

At step 2410, the method comprises inflating the balloon to an occlusive volume under ultrasound visualization.

The occlusive volume can vary based on, for example, the balloon size and vessel size. In some embodiments, the occlusion volume is about 2-3 cc.

The method comprises aspirating blood from the closure zone at step 2412.

In some embodiments, the method comprises aspirating all of the fluid from within the closure zone. In some embodiments, the method comprises most (e.g., greater than 50%, greater than 60%, greater than 70%, greater than 80%, greater than 90%, etc.) of the fluid from within the closure zone.

At step 2414, the method comprises infusing the desired amount of agent.

The method comprises maintaining the position and inflation of the balloon for a dwell period at step 2416. In some embodiments, the dwell period is about 2-5 minutes. Other dwell periods are also possible (e.g., 1-6 minutes, 2-4 minutes, 3-5 minutes, 3-4 minutes, 3 minutes, 4 minutes, etc.).

At step 2418, the method comprises deflating the balloon.

Deflating the balloon can comprise using the syringe to remove fluid from the balloon. In some embodiments, deflating the balloon comprises completely deflating the balloon. In some embodiments, deflating the balloon comprises mostly deflating the balloon (e.g., greater than about 90% of its volume).

The method comprises removing the balloon therapy device at step 2420.

In one alternative, the proximal balloon is not inflated until the distal balloon has reached the distal end of the closure zone. In an additional alternative embodiment, the second balloon is not inflated to an occlusion pressure until just before performing the active aspiration step 2030. In some embodiments, the hub is modified to include a separate inflation and deflation port in communication with the second balloon to allow from independent inflation. (See FIG. 12B)

In some alternative embodiments, one or more aspects of the inventive balloon based closure device and method may be modified to include one or more aspects, details or variations such as described in U.S. Pat. Nos. 3,625,793, 4,983,166, 5,087,244, 6,264,633, 5,919,163, US Patent Application Publication US 2003/0120256, US Patent Application Publication US 2005/0033227, US Patent Application Publication US 2005/0059931, and U.S. Pat. No. 5,676,962, the disclosure of each of which is incorporated herein by reference in its entirety.

While desiring not to be bound by theory, it is believed that one or a combination of mechanical engagement with the vessel wall within a portion of the closure zone including any of contacting, abrasion or penetration into or through some portion of an endothelial layer within a closure zone caused by interaction with a portion of a balloon therapy device embodiment described herein alone or in combination with aspiration alone or in combination with any level of vasospasm induced/endothelium injury in the vessel is likely to produce a localized reduced treatment volume. Advantageously, such a reduced volume along with aspiration of fluids from within the closure zone enables beneficial clinical results in less time while utilizing substantially less surgeon compounded closure agent or chemical closure agent or pharmacologically active or prescription strength closure agent. As a result, there is also provided a kit for performing balloon based closure therapy comprising a balloon based closure device as described herein along with a closure agent cannister having a volume of 2 cc, 3 cc, 4 cc, 5 cc, 10 cc, or more. In additional embodiments, the closure agent cannister contains sufficient closure agent for a single treatment and the cannister has a volume of less than 5 cc.

EXAMPLES

A device comprising a catheter comprising a distal balloon was used to perform a procedure in two animal subjects. The catheter comprises a 6 FR diameter. The device comprises mechanical abrasion elements extending over the distal balloon. The mechanical abrasion elements were fixed to the catheter by a collar distal to the balloon. The mechanical abrasion elements were fixed at their proximal end to collar configured to slide relative to the catheter. A device with two mechanical abrasion elements and a device with four mechanical abrasion elements were utilized.

The device was advanced from the right internal jugular vein to the treatment area in the distal iliac vein. The balloon was inflated with contrast under fluoroscopic guidance in the distal iliac vein. Contrast was infused, demonstrating juxtaposition of the balloon with the vein wall, and the device was retracted through the length of the respective bilateral iliac veins of both subjects.

The procedure was successful. Pathology analysis of explanted veins confirmed endothelial injury in the treated vein segments and showed no evidence of vessel perforation.

The tables below show the results from the histopathological analysis. Briefly, the external iliac veins were exposed, examined, and photographed. The veins were then flushed with saline to clear blood followed by 10% neutral buffered formalin to start fixation of the endothelium and intima. The veins were then explanted en bloc and pinned in fixed position to a corkboard backing.

For histology processing each treated vein segment was serially trimmed at approximately 3-5 mm intervals and placed sequentially in proximal to distal orientation in tissue processing cassettes for routine processing into paraffin and H&E staining (performed at VDx Preclinical, Davis, CA).

The following features were assessed and graded semi-quantitatively (0=absent, 1=minimal, 2=mild, 3=moderate, 4=severe): endothelial loss, hemorrhage, and inflammation (severity and type).

TABLE 5

Animal Subject 1-Right and Left Iliac Vein Treatment Site Scoring

| Slide | Section | Endothelial Loss | Hemorrhage | Inflammation | Inflammation Type | Comment |
|---|---|---|---|---|---|---|
| R1 | 1 | 4 | 0 | 0 | NA | NA |
|  | 2 | 4 | 0 | 0 | NA | NA |
|  | 3 | 4 | 0 | 0 | NA | NA |
| R2 | 1 | 4 | 0 | 0 | NA | NA |
|  | 2 | 4 | 0 | 0 | NA | NA |
|  | 3 | 4 | 0 | 0 | NA | NA |
| R3 | 1 | 3 | 0 | 0 | NA | NA |
|  | 2 | 4 | 0 | 0 | NA | NA |
|  | 3 | 4 | 0 | 0 | NA | NA |
|  | 4 | 4 | 0 | 0 | NA | NA |
| R4 | 1 | 1 | 0 | 0 | NA | NA |
|  | 2 | 1 | 0 | 0 | NA | NA |
| L1 | 1 | 4 | 0 | 0 | NA | NA |
|  | 2 | 4 | 0 | 0 | NA | NA |
|  | 3 | 4 | 0 | 0 | NA | NA |
| L2 | 1 | 4 | 0 | 0 | NA | NA |
|  | 2 | 4 | 0 | 0 | NA | NA |
|  | 3 | 4 | 0 | 0 | NA | NA |
| L3 | 1 | 2 | 0 | 0 | NA | NA |
|  | 2 | 2 | 0 | 0 | NA | NA |
|  | 3 | 2 | 0 | 0 | NA | NA |
| L4 | 1 | 2 | 0 | 0 | NA | NA |
|  | 2 | 2 | 0 | 0 | NA | NA |

TABLE 6

Animal Subject 2-Right and Left Iliac Vein Treatment Site Scoring

| Slide | Section | Endothelial Loss | Hemorrhage | Inflammation | Inflammation Type | Comment |
|---|---|---|---|---|---|---|
| R1 | 1 | 3 | 0 | 0 | NA | NA |
|  | 2 | 4 | 0 | 0 | NA | NA |
|  | 3 | 4 | 0 | 0 | NA | NA |
| R2 | 1 | 4 | 0 | 0 | NA | NA |
|  | 2 | 4 | 0 | 0 | NA | NA |
|  | 3 | 4 | 0 | 0 | NA | NA |
| R3 | 1 | 4 | 0 | 0 | NA | NA |
|  | 2 | 4 | 0 | 0 | NA | NA |
|  | 3 | 4 | 0 | 0 | NA | NA |
| R4 | 1 | 2* | 0 | 0 | NA | *Partial section, tangential artifact |
|  | 2 | 4 | 0 | 0 | NA | NA |
|  | 3 | 4 | 0 | 0 | NA | NA |
| R5 | 1 | 4 | 0 | 0 | NA | NA |
| L1 | 1 | 4 | 0 | 0 | NA | NA |
|  | 2 | 4 | 0 | 0 | NA | NA |
|  | 3 | 4 | 0 | 0 | NA | NA |
| L2 | 1 | 3 | 0 | 0 | NA | NA |
|  | 2 | 4 | 0 | 0 | NA | NA |
|  | 3 | 4 | 0 | 0 | NA | NA |
| L3 | 1 | 4 | 1 | 0 | NA | NA |
|  | 2 | 4 | 0 | 0 | NA | NA |
|  | 3 | 2* | 0 | 0 | NA | *Partial section, tangential artifact |
| L4 | 1 | 1 | 0 | 0 | NA | NA |

Figure 25A:
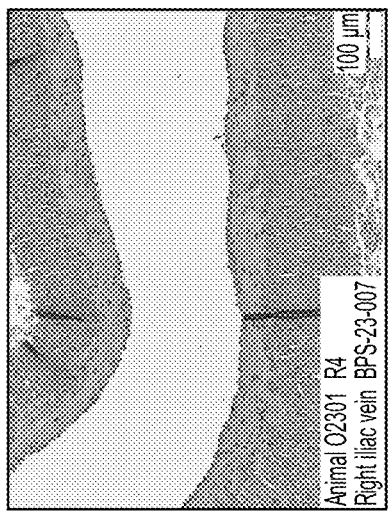
FIGS. 25A-G show various microscopic views of venous segments from treated animal subjects.
Figure 25B:
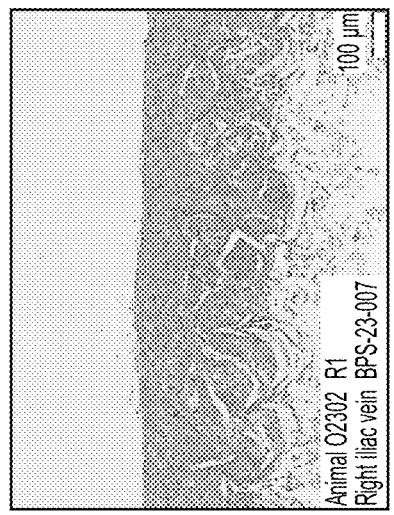
Figure 25C:
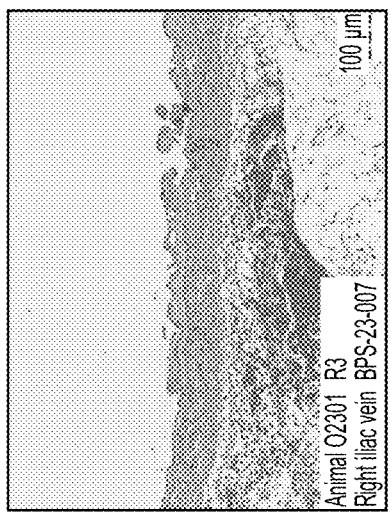
Figure 25D:
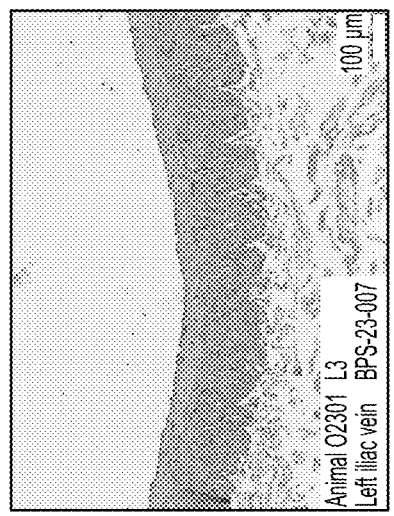
Figure 25E:
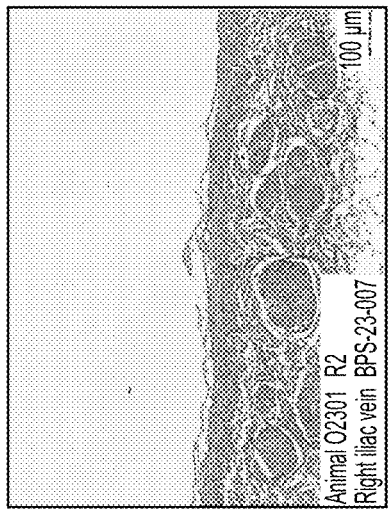

FIGS. 25A-E show highly magnified microscopic views of the explanted veins of the two subjects. FIG. 25A show a high magnification representation of the intimal surface of a first area of a treated portion of the right iliac vein of first subject. This view shows micro fibrillation and endothelial loss. FIG. 25B shows a high magnification representation of the intimal surface of a second area of a treated portion of the right iliac vein of first subject. For comparison, FIG. 25C shows a magnified microscopic view of an untreated portion of the right iliac vein of the subject. This view shows the presence of endothelial cells on the intima. FIG. 25D shows a high magnification representation of the intimal surface of a first area of a treated portion of the left iliac vein of first subject. This view shows micro fibrillation and endothelial loss. FIG. 25E shows a high magnification representation of the intimal surface of a second area of a treated portion of the right iliac vein of first subject. This view shows the intima with a patchy loss of endothelial cells.

Figure 25F:
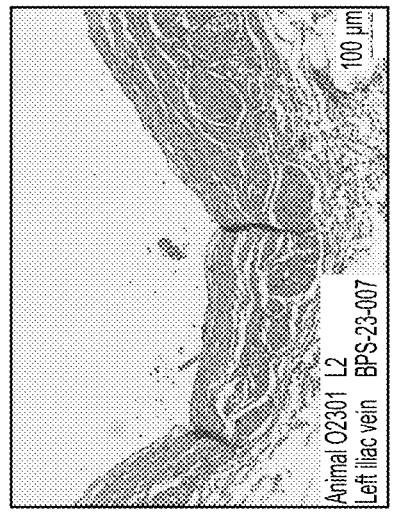
Figure 25G:
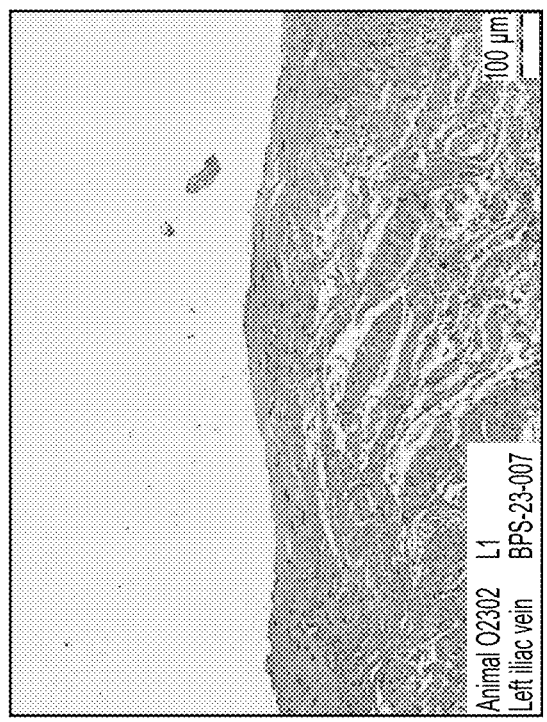

FIG. 25F shows a high magnification representation of a treated portion of the right iliac vein of the second subject. This view shows micro fibrillation/disruption and endothelial loss. FIG. 25G shows a high magnification representation of a treated portion of the left iliac vein of the second subject. This view shows endothelial loss and a microscopic foci of minimal compression injury in the wall of the vein (outline).

The above examples demonstrate the viability of using the devices described herein to cause venous wall injury and abrasion, for example, to treat varicose veins without the use of heat. Visualization during the procedure and pathology of the treated veins confirmed that the methods disclosed herein were successful in causing vein ablation.

Advantageously, some embodiments of the balloon therapy systems described herein specifically accommodate for the elongation of compliant balloons by adjusting the length of free or unattached mechanical abrasion element between each of the proximal and the distal end of the balloon. There is one portion of a mechanical abrasion element that runs directly along the balloon in the deflated state. That portion of the mechanical abrasion element will deflect immediately as the balloon is inflated. Next, as the balloon continues to inflate, additional lengths of the mechanical abrasion element extending proximally and distally from the proximal and distal ends of the balloon will also defect radially away from the catheter body. Because of the elongation of the balloon, the length of mechanical abrasion element that will be positioned between the balloon outer surface and the inner vessel wall will increase. As a result, the various spacing of the proximal and distal ends of the mechanical abrasion elements allows the amount of tissue engagement to be adjusted in use or by prior design configuration. In one specific aspect, the balloon treatment device has a mechanical treatment element configured as two wires and each of the two wired has a section configured to deflect radially outwardly alongside the balloon. This section will vary with the length of the balloon. In various embodiments, the balloon may have a length between 20 mm to 26 mm. In one specific embodiment, the length of the section of a mechanical abrasion element along the balloon is at least 20 mm. Still further, in order to take advantage of the elongation effect common to compliant balloons, the spacing from the proximal or distal end of the balloon to a point where an end portion of a mechanical abrasion element is coupled to the catheter shaft may also vary and be adjusted to further modify the performance of a balloon therapy device. Put another way, the amount of free abrasion element may be lifted off of the catheter body and urged into contact with the adjacent vessel wall. Additionally, there will also be a length of a mechanical abrasion element that may be radially separated from the catheter wall but not in contact with the vessel wall. In some embodiments the distance of separation from the proximal to distal ends of the balloons to the mechanical abrasion element coupling point may be the same or different on each of the proximal and distal ends. As used herein, coupled to the catheter shaft includes any of the attachment points between a mechanical abrasion element and the catheter shaft such as the use of an externally mounted collar, attachment to or along the surface of the catheter wall or at an opening of a dedicated lumen within the catheter wall used to house an end of a mechanical abrasion element. Accordingly, in some embodiments, the mechanical abrasion elements may be configured as two elements each having a wire form factor. A distal end of each of the two wires is coupled to the catheter shaft at a distance from 7 mm to 20 mm from a distal end of the balloon and a proximal end of each of the two wires is coupled to the catheter shaft at a distance from 12 mm to 25 mm from a proximal end of the balloon.

Although an embodiment has been described with reference to specific example embodiments, it will be evident that various modifications and changes may be made to these embodiments without departing from the scope of the present disclosure. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Various aspects of the disclosure have been described above. It should be apparent that the teachings herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, an apparatus may be implemented or a method may be practiced using any number of the aspects set forth herein. In addition, such an apparatus may be implemented or such a method may be practiced using other structure, functionality, or structure and functionality in addition to or other than one or more of the aspects set forth herein.

While the invention has been described in connection with various aspects, it will be understood that the embodiments disclosed herein are capable of further modifications. This application is intended to cover any variations, uses or adaptation of the invention following, in general, the principles of the invention, and including such departures from the present disclosure as come within the known and customary practice within the art to which the invention pertains.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for closing a portion of a diseased vein in a patient, comprising:
   accessing a portion of a venous vasculature of the patient with a balloon therapy device having a balloon:
   advancing the balloon therapy device into a portion of the diseased vein;
   forming a proximal end of a closure zone in the diseased vein by partially inflating the balloon to a mechanical treatment volume for engagement with an inner wall of the diseased vein;
   while maintaining the balloon at the mechanical treatment volume, advancing the balloon therapy device along the diseased vein to a distal end of the closure zone;
   inflating the balloon to occlude the diseased vein;
   while occluding the diseased vein, aspirating a portion of fluid from within the closure zone;
   injecting a closure agent into the closure zone; and
   maintaining occlusion in the diseased vein until a closure agent dwell time has elapsed.

2. The method of claim 1, further comprising:
   deflating the balloon; and
   withdrawing the balloon therapy device from the patient.

3. The method of claim 1, wherein advancing the balloon therapy device along the diseased vein to the distal end of the closure zone comprises injuring an endothelial layer and/or loss of endothelial cells of the diseased vein along the closure zone.

4. The method of claim 3, wherein injuring the endothelial layer is substantially performed by at least one mechanical abrasion element of a mechanical abrasion assembly.

5. The method of claim 1, further comprising visualizing the balloon therapy device using an ultrasound probe.

6. The method of claim 1, wherein after the step of injecting the closure agent into the closure zone, performing a step of applying a force from outside of the closure zone to distribute the closure agent along the closure zone.

7. The method of claim 6, wherein the step of applying force from outside of the closure zone is performed using an ultrasound probe and under ultrasound imaging.

8. The method of claim 6, wherein the step of applying a force from outside of the closure zone distributes the closure agent towards the proximal end of the closure zone and across at least one incompetent vein.

9. The method of claim 1, wherein after the step of inflating the balloon to the mechanical treatment volume at least one mechanical abrasion element is positioned between a surface of the balloon and a surface of the diseased vein.

10. A method for closing a portion of a diseased vein in a patient, comprising:
    accessing a portion of a venous vasculature of the patient with a balloon therapy device having a balloon:
    advancing the balloon therapy device into a portion of the diseased vein;
    forming a proximal end of a closure zone in the diseased vein by partially inflating the balloon to a mechanical treatment volume for engagement with an inner wall of the diseased vein, wherein when the balloon is filled to the mechanical treatment volume within the diseased vein a length of the balloon along the diseased vein is greater than a width of the balloon across the diseased vein;
    while maintaining the balloon at the mechanical treatment volume, advancing the balloon therapy device along the diseased vein to a distal end of the closure zone;
    inflating the balloon to an occlusion volume causing the balloon to occlude the diseased vein at the distal end of the closure zone;
    while maintaining the balloon at the occlusion volume, aspirating a portion of fluid from within the closure zone;
    injecting a closure agent into the closure zone; and
    maintaining the balloon at the occlusion volume until a closure agent dwell time has elapsed.

11. The method of claim 10, further comprising
    deflating the balloon; and
    withdrawing the balloon therapy device from the patient.

12. The method of claim 10, wherein advancing the balloon therapy device along the diseased vein to the distal end of the closure zone comprises injuring only a portion of an endothelium of the diseased vein along the closure zone.

13. The method of claim 10, further comprising visualizing the balloon therapy device using ultrasound while applying a force outside of the diseased vein to distribute the closure agent along the closure zone.

14. A method for closing a portion of a diseased vein in a patient, comprising:
    accessing a portion of a venous vasculature of the patient with a balloon therapy device, having a balloon that is compliant;
    advancing the balloon therapy device into a portion of the diseased vein;
    inflating the balloon into a cylindrical shape at a proximal end of a closure zone to transition a mechanical abrasion structure from a stowed configuration into a partially deployed configuration in contact with a wall of the diseased vein;
    while maintaining the mechanical abrasion structure in the partially deployed configuration, advancing the balloon therapy device along the diseased vein to a distal end of the closure zone;
    inflating the balloon to occlude the diseased vein while aspirating a portion of fluid from within the closure zone;
    injecting a closure agent into the closure zone after aspirating the portion of the fluid within the closure zone; and
    continuing to occlude the diseased vein with the balloon until a closure agent dwell time has elapsed.

15. The method of claim 14, further comprising
    deflating the balloon to return the mechanical abrasion structure to a stowed configuration; and
    withdrawing the balloon therapy device from the patient.

16. The method of claim 15, wherein an elapsed time from performing the step of advancing the balloon therapy device into the portion of the diseased vein to completing the step of withdrawing the balloon therapy device from the patient is less than 10 minutes.

17. The method of claim 14, further comprising visualizing a portion of the mechanical abrasion structure using ultrasound.

18. The method of claim 14, further comprising visualizing the balloon therapy device using ultrasound while performing the step of inflating the balloon to transition the mechanical abrasion structure from the stowed configuration into the partially deployed configuration in contact with the wall of the diseased vein.

19. The method of claim 14, wherein when the mechanical abrasion structure is in the partially deployed configuration one or more tissue engagement elements contact a wall of the diseased vein.

20. The method of claim 14, wherein the closure agent dwell time is from 2-5 minutes.

21. The method of claim 14, wherein advancing the balloon therapy device along the diseased vein to the distal end of the closure zone comprises injuring an endothelial layer and/or loss of endothelial cells of the diseased vein along the closure zone.

22. The method of claim 14, wherein the step of aspirating the portion of fluid from within the closure zone is performed using an aperture proximal to the balloon.

23. The method of claim 22, wherein the step of injecting the closure agent into the closure zone is performed using the aperture.

24. The method of claim 14, further comprising, coupling a syringe to a connector at a proximal end of the balloon therapy device outside of a patient vasculature before performing the aspiration step.

25. The method of claim 24, further comprising performing the injecting the closure agent step using the connector.

26. The method of claim 14, wherein the closure zone is within a vein in a leg of the patient.

27. The method of claim 14, further comprising: using an imaging modality to confirm the position of a distal portion of the balloon therapy device before the step of inflating the balloon into the cylindrical shape at the proximal end of the closure zone, advancing the balloon therapy device along the diseased vein to the distal end of the closure zone, inflating the balloon to occlude the diseased vein while aspirating the portion of fluid from within the closure zone, or injecting the closure agent into the closure zone after aspirating the portion of the fluid within the closure zone.

28. The method of claim 14, wherein an aperture in a catheter shaft proximal to the treatment balloon is in communication with a lumen that extends to the proximal end of the balloon therapy device, further wherein the aspiration step and the injection step are performed using the aperture and the lumen.

29. The method of claim 14, wherein inflating the balloon to transition the mechanical abrasion structure from the stowed configuration into the partially deployed configuration comprises moving a portion of at least one mechanical abrasion element of the mechanical abrasion structure proximally along a dedicated mechanical abrasion element lumen of the balloon therapy device.

30. The method of claim 14, wherein advancing the balloon therapy device along the diseased vein to the distal end of the closure zone comprises advancing the balloon therapy device past at least one incompetent valve in the diseased vein.

* * * * *